(12) United States Patent
Mun et al.

(10) Patent No.: US 11,557,729 B2
(45) Date of Patent: Jan. 17, 2023

(54) COMPOUND FOR ORGANIC ELECTRONIC ELEMENT, ORGANIC ELECTRONIC DEVICE USING SAME, AND ELECTRONIC DEVICE THEREOF

(71) Applicant: DUK SAN NEOLUX CO., LTD., Cheonan-si (KR)

(72) Inventors: Soung Yun Mun, Cheonan-si (KR); Min Ji Jo, Incheon (KR); Sun Hee Lee, Hwaseong-si (KR); Nam Geol Lee, Seoul (KR); Hyung Dong Lee, Ulsan (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 285 days.

(21) Appl. No.: 16/317,137

(22) PCT Filed: Jul. 4, 2017

(86) PCT No.: PCT/KR2017/007086
§ 371 (c)(1),
(2) Date: Jan. 11, 2019

(87) PCT Pub. No.: WO2018/012781
PCT Pub. Date: Jan. 18, 2018

(65) Prior Publication Data
US 2019/0300535 A1    Oct. 3, 2019

(30) Foreign Application Priority Data

Jul. 14, 2016  (KR) .................. 10-2016-0089346
Jul. 3, 2017   (KR) .................. 10-2017-0084144

(51) Int. Cl.
C07D 487/04  (2006.01)
C07D 519/00  (2006.01)
(Continued)

(52) U.S. Cl.
CPC ........ *H01L 51/0061* (2013.01); *C07D 487/04* (2013.01); *C07D 491/048* (2013.01);
(Continued)

(58) Field of Classification Search
None
See application file for complete search history.

(56) References Cited

U.S. PATENT DOCUMENTS

| 5,843,607 A | 12/1998 | Hu et al. |
| 2010/0187977 A1 | 7/2010 | Kai et al. |
| 2014/0326987 A1 | 11/2014 | Park et al. |

FOREIGN PATENT DOCUMENTS

| JP | 11-162650 A | 6/1999 |
| JP | 2002-241661 A | 8/2002 |

(Continued)

OTHER PUBLICATIONS

Machine English translation of Eom et al. (KR 10-2014-0111719). Mar. 2, 2021.*

(Continued)

*Primary Examiner* — Jay Yang
(74) *Attorney, Agent, or Firm* — Vorys, Sater, Seymour and Pease LLP; Mih Suhn Koh

(57) ABSTRACT

Provided are an organic electronic element and an electronic device thereof, the organic electronic element being capable of achieving high light-emitting efficiency and a low driving voltage, and can also greatly improve the lifespan of the element by using a compound of the present invention as a phosphorescent host material.

12 Claims, 1 Drawing Sheet

(51) Int. Cl.
  *C07D 495/04* (2006.01)
  *C07D 491/048* (2006.01)
  *H01L 51/00* (2006.01)
  *H01L 51/50* (2006.01)
  *H01L 51/52* (2006.01)
  *H01L 27/32* (2006.01)
  *H01L 51/56* (2006.01)

(52) U.S. Cl.
  CPC ......... *C07D 495/04* (2013.01); *C07D 519/00* (2013.01); *H01L 51/006* (2013.01); *H01L 51/0054* (2013.01); *H01L 51/0059* (2013.01); *H01L 51/0067* (2013.01); *H01L 51/0071* (2013.01); *H01L 51/0072* (2013.01); *H01L 27/3244* (2013.01); *H01L 51/001* (2013.01); *H01L 51/0058* (2013.01); *H01L 51/0073* (2013.01); *H01L 51/0074* (2013.01); *H01L 51/5004* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 51/5278* (2013.01); *H01L 51/56* (2013.01); *H01L 2251/301* (2013.01); *H01L 2251/308* (2013.01); *H01L 2251/5384* (2013.01); *H01L 2251/552* (2013.01); *H01L 2251/558* (2013.01)

(56) References Cited

FOREIGN PATENT DOCUMENTS

| KR | 10-2008-0085000 A | 9/2008 |
| KR | 10-2009-0057711 A | 6/2009 |
| KR | 10-2011-0018340 A | 2/2011 |
| KR | 10-2014-0111719 A | 9/2014 |
| WO | WO-2013/081315 A1 * | 6/2013 |
| WO | WO-2014/142467 A1 * | 9/2014 |

OTHER PUBLICATIONS

Chinese Office Action dated Jul. 30, 2021, for corresponding CN Application No. 201780043717.6, 13 pages.
Chemical Abstract compound, STN express: RN 1628071-78-2 (Entered STN: Oct. 6, 2014).
Chemical Abstract compound, STN express: RN 1628069-92-0 (Entered STN: Oct. 6, 2014).
Chemical Abstract compound, STN express: RN 1628072-22-9 (Entered STN: Oct. 6, 2014).

* cited by examiner

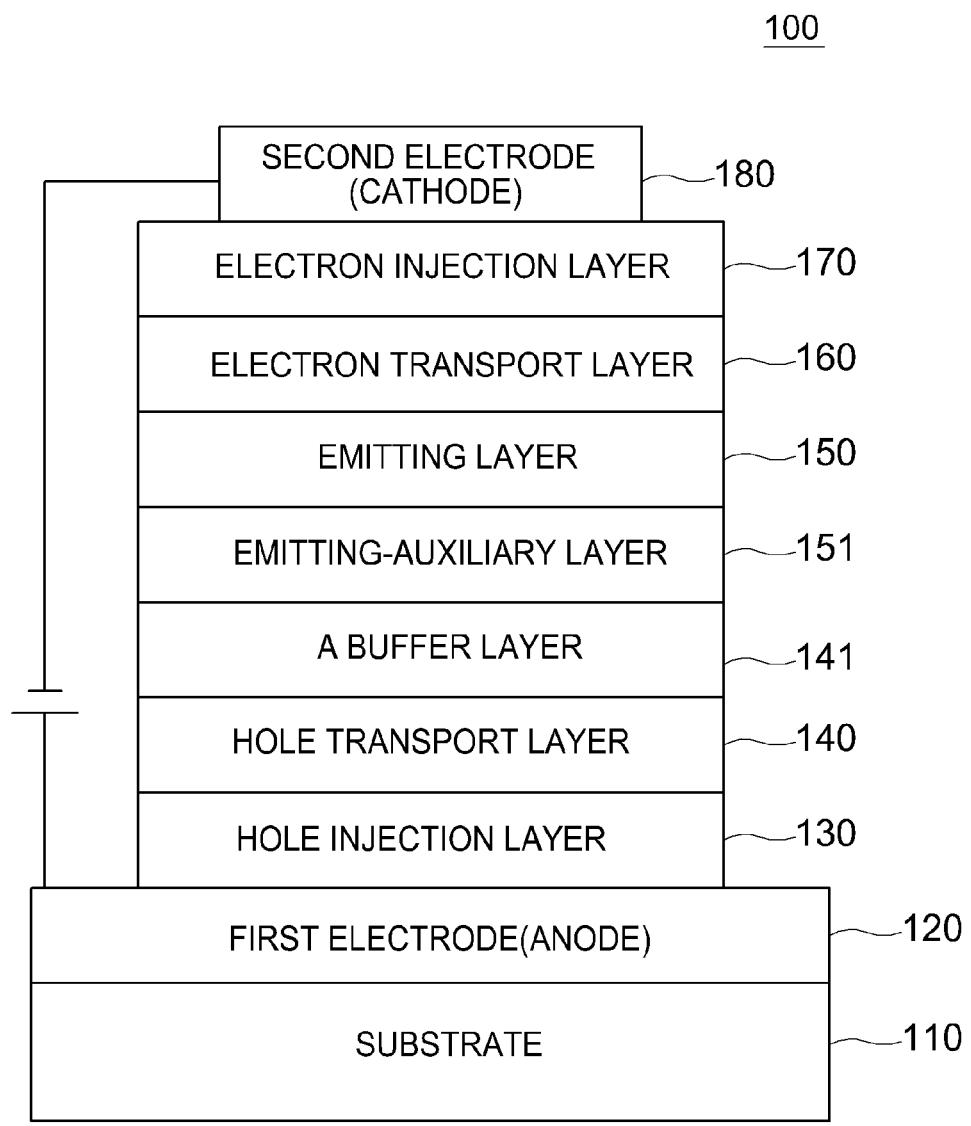

COMPOUND FOR ORGANIC ELECTRONIC ELEMENT, ORGANIC ELECTRONIC DEVICE USING SAME, AND ELECTRONIC DEVICE THEREOF

BACKGROUND

Technical Field

The present invention relates to compound for organic electronic element, organic electronic element using the same, and an electronic device thereof.

Background Art

In general, organic light emitting phenomenon refers to a phenomenon that converts electronic energy into light energy by using an organic material.

An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function.

In the case of a polycyclic compound containing a heteroatom, the difference in properties according to the material structure is so large that it is applied to various layers as a material of an organic electronic element. In particular, it has characteristics of different band gaps (HOMO, LUMO), electronical characteristics, chemical properties, and physical properties depending on the number of rings, fused positions and the type and arrangement of heteroatoms, therefore application development for layers of various organic electronic elements using the same has been progressed.

As a representative example thereof, in the following Patent Documents 1 to 4, the performance of the 5-membered cyclic compound in the polycyclic compound has been reported depending on the hetero type, arrangement, substituent type, fused position, and the like.
[Patent Document 1]: U.S. Pat. No. 5,843,607
[Patent Document 2]: Japanese Laid-Open Patent Publication No. 1999-162650
[Patent Document 3]: Korean Published Patent Application No. 2008-0085000
[Patent Document 4]: US Patent Publication No. 2010-0187977
[Patent Document 5]: Korean Published Patent Application No. 2011-0018340
[Patent Document 6]: Korean Published Patent Application No. 2009-0057711

Patent Documents 1 and 2 disclose an embodiment in which the indolecarbazole core in which the hetero atom in the 5-membered cyclic compound is composed only of nitrogen (N) is used, and an aryl group substituted or unsubstituted in N of indolocarbazole is used. However, in the prior invention 1, there exists only a simple aryl group substituted or unsubstituted with an alkyl group, an amino group, an alkoxy group, or the like as a substituent, so that the effect of the substituents of the polycyclic compounds was very poor to prove, and only the use as a hole transport material is described, and the use thereof as a phosphorescent host material is not described.

Patent Documents 3 and 4 disclose a compound in which pyridine, pyrimidine, triazine or the like containing an aryl group and N, respectively, were substituted for an indolecarbazole core having a hetero atom N in the same 5-membered cyclic compound as in the above Patent Documents 1 and 2, however only the use examples for phosphorescent green host materials are described, and the performance for other heterocyclic compounds substituted for indolecarbazole core is not described.

In Patent Documents 5, Nitrogen (N), oxygen (O), sulfur (S), carbon and the like are described as heteroatom in the 5-membered cyclic compound, however there are only examples using the same heteroatom in the performance measurement data, the performance characteristics of a 5-membered cyclic compound containing a different heteroatom could not be confirmed.

Therefore, the patent document does not disclose solutions to low charge carrier mobility and low oxidation stability of a 5-membered cyclic compound containing same heteroatom.

When the 5-membered cyclic compound molecules are generally laminated, as the adjacent π-electrons increase, they have a strong electronical interaction, and this is closely related to the charge carrier mobility, particularly, the same 5-membered cyclic compound of N—N type has an edge-to-face morphology as an order of arrangement of molecules when molecules are laminated, otherwise a different 5-membered cyclic compound with different heteroatoms has an antiparallel cofacial π-stacking structure in which the packing structure of the molecules is opposite to each other, so that the arrangement order of the molecules becomes face-to-face morphology. It is reported that the steric effect of the substituent substituted on the asymmetrically arranged hetero atom N as the cause of this laminated structure causes relatively high carrier mobility and high oxidation stability (*Org. Lett.* 2008, 10, 1199).

In Patent Document 6, an example of using as a fluorescent host material for various polycyclic compounds having 7 or more membered cyclic compounds has been reported.

As described above, the fused positions, the number of rings, the arrangement of heteroatoms, and characteristic change by type of the polycyclic compounds have not yet been sufficiently developed.

Particularly, in a phosphorescent organic electronic element using a phosphorescent dopant material, the LUMO and HOMO levels of the host material have a great influence on the efficiency and life span of the organic electronic element, this is because the charge balance control in the emitting layer, the quenching of the dopant, and the reduction in efficiency and life span due to light emission at the interface of the hole transport layer can be prevented, depending on whether electron and hole injection in the emitting layer can be efficiently controlled.

For fluorescent and phosphorescent host materials, recently we have been studying the increase of efficiency and life span of organic electronic elements using TADF (thermal activated delayed fluorescent), exciplex, etc., particularly, and many studies have been carried out to identify the energy transfer method from the host material to the dopant material.

Although there are various methods for identifying the energy transfer in the emitting layer for TADF (thermally activated delayed fluorescent) and exciplex, it can be easily confirmed by the PL lifetime (TRIP) measurement method.

The TRIP (Time Resolved Transient PL) measurement method is a method of observing a decay time over time after irradiating the host thin film with a pulsed light source, and therefore it is possible to identify the energy transfer method by observing the energy transfer and the lag time. The TRTP measurement can distinguish between fluorescence and phosphorescence, an energy transfer method in a mixed host material, an exciplex energy transfer method, and a TADF energy transfer method.

There are various factors affecting the efficiency and life span depending on the manner in which the energy is transferred from the host material to the dopant material, and the energy transfer method differs depending on the material, so that the development of stable and efficient host material for organic electronic element has not yet been sufficiently developed. Therefore, development of new materials is continuously required, and especially development of a host material for an emitting layer is urgently required.

DETAILED DESCRIPTION OF THE INVENTION

Summary

The present invention relates to a compound capable of improving charge balance adjustment, efficiency and lifetime in an emitting layer by controlling the energy level of a host material of a phosphorescent emitting organic electric element including a phosphorescent dopant, and an organic electric element using the same and an electronic device thereof.

Technical Solution

By containing a specific host as a main component for controlling the efficient hole injection in the emitting layer of the phosphorescence emitting organic electronic element, the present invention provides a compound capable of improving charge balance adjustment, efficiency and lifetime in the emitting layer, and an organic electric element including the same.

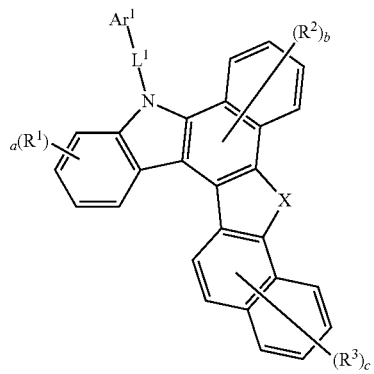

In another aspect, the present invention also provides an organic electronic element using the compound represented by the above Formulas and an electronic device thereof.

Effects of the Invention

By using the mixture according to the present invention as a phosphorescent host material, it is possible to achieve a high luminous efficiency and a low driving voltage of an organic electric element, and the life span of the device can be greatly improved.

BRIEF DESCRIPTION OF THE DRAWINGS

The FIGURE is an illustration of an organic electroluminescent device according to the present invention.

| | |
|---|---|
| 100: organic electric element, | 110: substrate |
| 120: the first electrode(anode), | 130: the hole injection layer |
| 140: the hole transport layer, | 141: a buffer layer |
| 150: the emitting layer, | 151: the emitting auxiliary layer |
| 160: the electron transport layer, | 170: the electron injection layer |
| 180: the second electrode(cathode) | |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "linked" to another component, the component may be directly connected or connected to the other component, but another component may be "connected", "coupled" or "linked" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, includes an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxyl group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and includes at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring containing $SO_2$ instead of carbon consisting of cycle. For example, "heterocyclic group" includes compound below.

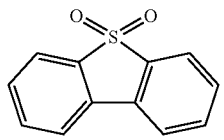

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these. Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

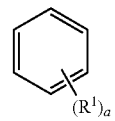

Wherein, when a is an integer of zero, the substituent $R^1$ is absent, and when a is an integer of 1, the sole substituent $R^1$ is linked to any one of the carbon constituting the benzene ring, and when a is an integer of 2 or 3, they are respectively combined as follows, wherein $R^1$ may be the same or different from each other. When a is an integer from 4 to 6, it is bonded to the carbon of the benzene ring in a similar manner, while the labeling of the hydrogen bonded to the carbon forming the benzene ring is omitted.

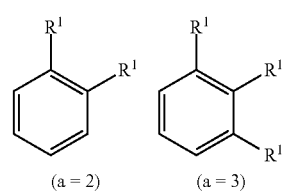

Unless otherwise expressly stated, the terms "ortho", "meta", and "para" used in the present invention refer to the substitution positions of all substituents, and the ortho position indicates the position of the substituent immediately adjacent to the compound, for example, when benzene is used, it means 1 or 2 position, and the meta position is the next substitution position of the neighbor substitution position, when benzene as an example stands for 1 or 3 position, and the para position is the next substitution position of the meta position, which means 1 and 4 position when benzene is taken as an example. A more detailed example of the substitution position is as follows, and it can be confirmed that the ortho-, and meta-position are substituted by non-linear type and para-positions are substituted by linear type.

[Example of Ortho-Position]

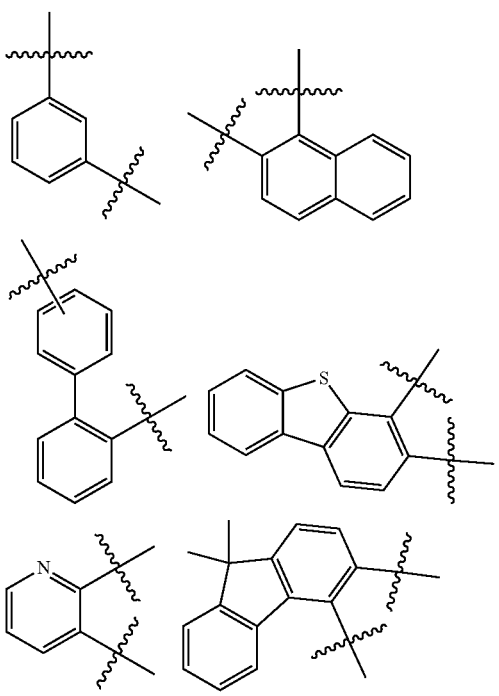

[Example of Meta-Position]

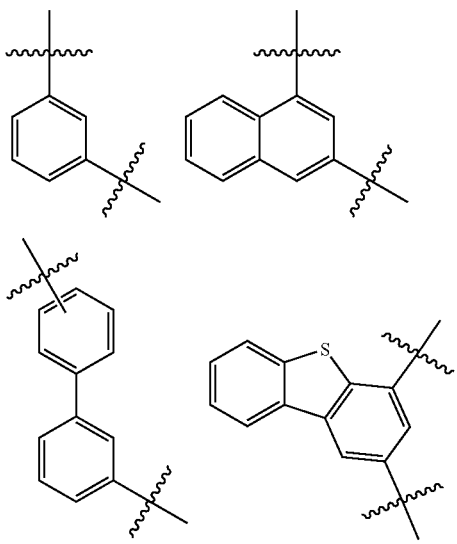

-continued

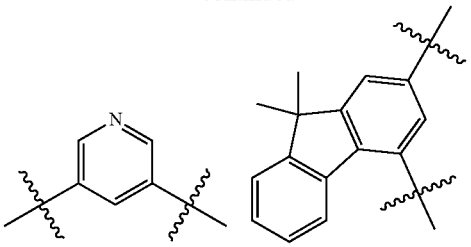

[Example of Para-Position]

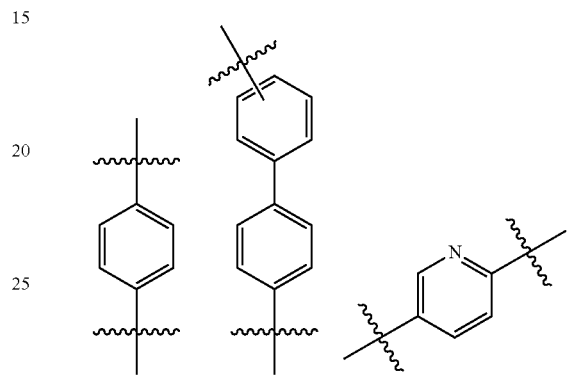

Hereinafter, a compound according to an aspect of the present invention and an organic electric element comprising the same will be described.

The present invention provides a compound represented by Formula 1.

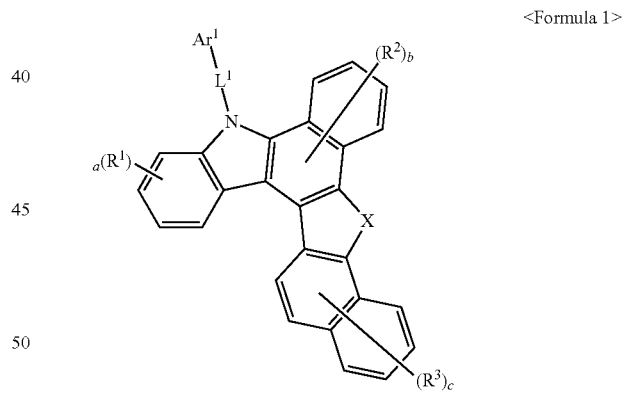

<Formula 1>

{in Formula 1,
1) X is N-$L^2$-$Ar^2$, O or S,
2) $Ar^1$ and $Ar^2$ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R^a$)($R^b$);
3) a and b are an integer of 0 to 4, and c is an integer of 0 to 6,
4) $R^1$, $R^2$ and $R^3$ are the same or different from each other, and are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R^a$)($R^b$); or in case a, b and c are 2 or more, and $R^1$, $R^2$ and $R^3$ are each in plural being the same or different, and a plurality of $R^1$ or a plurality of $R^2$ or a plurality of $R^3$ may be bonded to each other to form a ring.

5) $L^1$ and $L^2$ are each independently selected from the group consisting of a single bond; a $C_6$-$C_{60}$ arylene group; and a fluorenylene group; a fused ring group of a $C_3$-$C_{60}$ aliphatic ring and a $C_6$-$C_{60}$ aromatic ring; and a $C_2$-$C_{60}$ heterocyclic group;

6) L' is selected from the group consisting of a single bond; a $C_6$-$C_{60}$ arylene group; and a fluorenylene group; a fused ring group of a $C_3$-$C_{60}$ aliphatic ring and a $C_6$-$C_{60}$ aromatic ring; and a $C_2$-$C_{60}$ heterocyclic group; and $R^a$ and $R^b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P, wherein, the aryl group, fluorenyl group, arylene group, heterocyclic group, fluorenylene group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L-N($R^a$)($R^b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; wherein the substituents may combine each other and form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination of thereof.}

The compound represented by Formula 1 is represented by any one of the following Formulas 2 to 4.

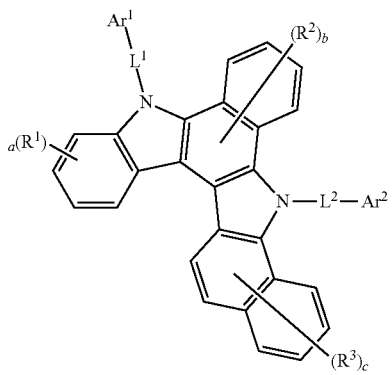

<Formula 2>

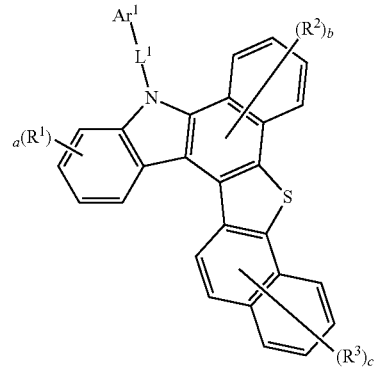

<Formula 3>

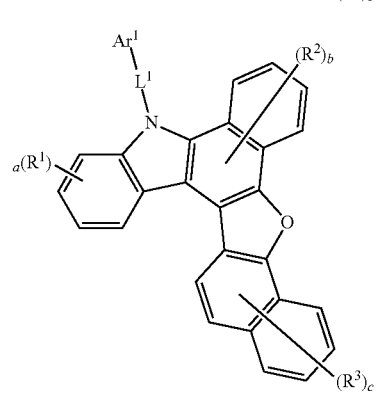

<Formula 4>

{in Formulas 2 to 4,
$R^1$, $R^2$, $R^3$, $L^1$, $L^2$, $Ar^1$, $Ar^2$, a, b and c are the same as defined above}

$Ar^1$ and $Ar^2$ in Formula 1 are represented by Formula A-1 or A-2.

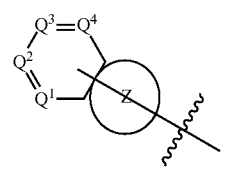

<Formula A-1>

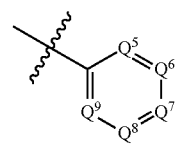

<Formula A-2>

{in Formulas A-1 or A-2,
1) $Q^1$, $Q^2$, $Q^3$, $Q^4$, $Q^5$, $Q^6$, $Q^7$, $Q^8$ and $Q^9$ are each independently N or $CR^e$, 2) $R^e$ is selected from the group consisting of hydrogen; deuterium; halogen; a silane group substituted or unsubstituted with $C_1$-$C_{20}$ alkyl group or $C_6$-$C_{20}$ aryl group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; containing at least one hetero atom of O, N, S, Si, or P, $C_3$-$C_{20}$cycloalkyl group; $C_7$-$C_{20}$ arylalkyl group; and $C_8$-$C_{20}$ arylalkenyl group;

3) Z is any one of Formulas C-1 to C-15,

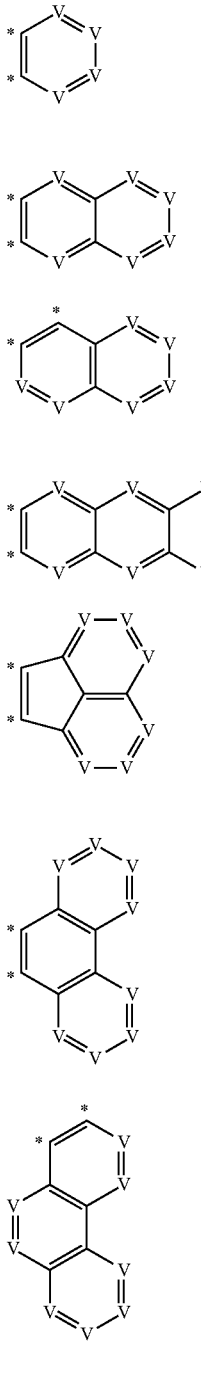

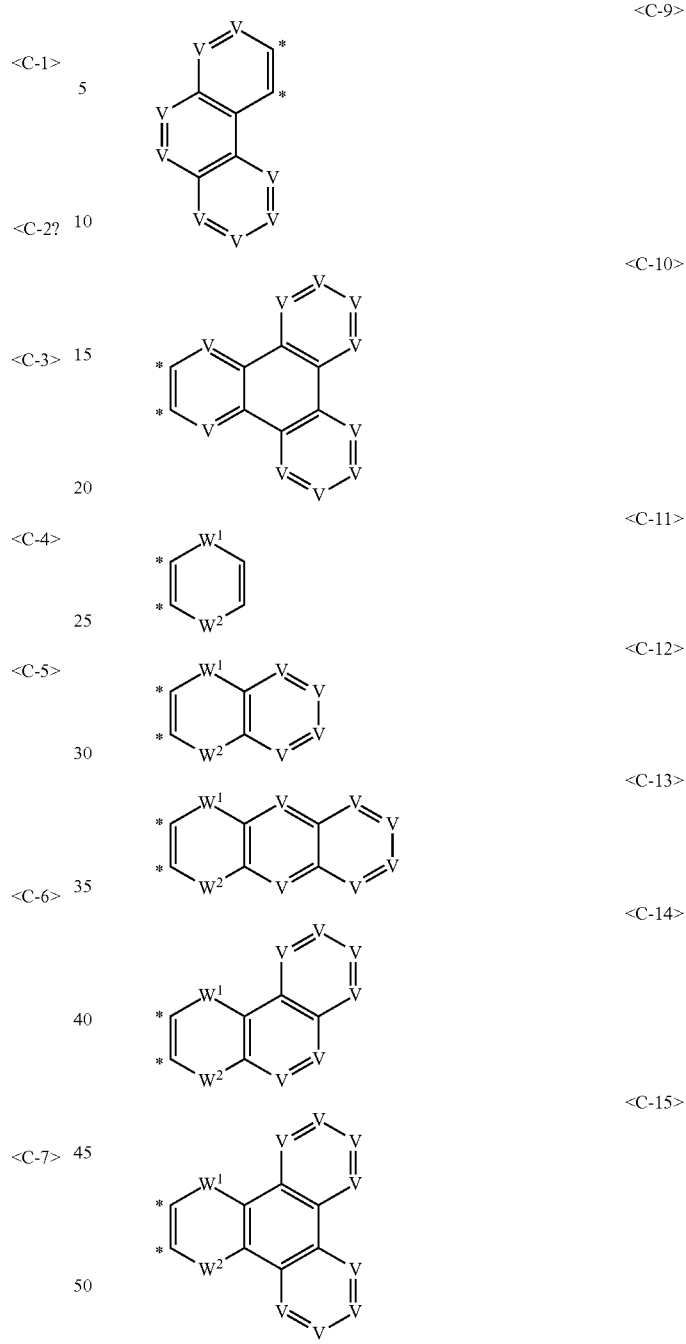

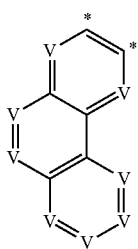

wherein the mark * represents a bonding moiety which combines with the ring including Q1 to Q4 to form a fused ring, 4) in Formulas C-1 to C-15, $W^1$ and $W^2$ are single bond, $N-L^3-Ar^3$, S, O or $C(R^f)(R^g)$, 5) V is each independently N or $CR^h$, 6) $L^3$ is selected from a single bond; a $C_6$-$C_{60}$ arylene group; and a fluorenylene group; $C_2$-$C_{60}$ divalent heterocyclic group containing at least one hetero atom of O, N, S, Si, or P; a divalent fused ring group of a $C_3$-$C_{60}$ aliphatic ring and a $C_6$-$C_{60}$ aromatic ring; and a divalent aliphatic hydrocarbon group;

7) Ara, $R^f$, $R^g$ and $R^h$ are each independently selected from the aryl group, fluorenyl group, a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; $R^f$ and $R^g$ may be bonded to each other to form a spiro together with the carbon (C) to which they are bonded.}

The present invention also provides the following compounds 1-1 to 1-101 comprised in Formula 1.

1-1

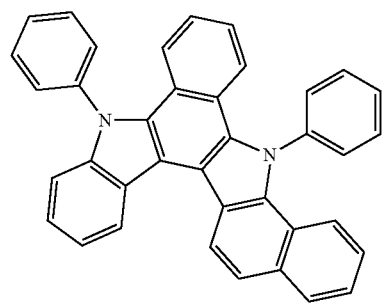

1-2

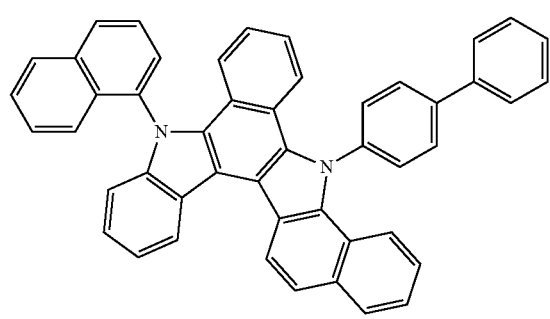

1-3

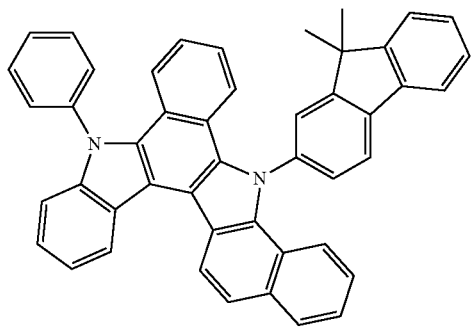

1-4

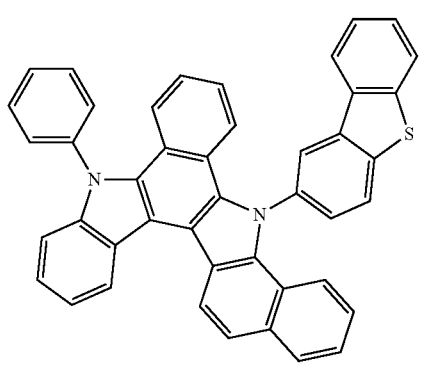

-continued 1-5

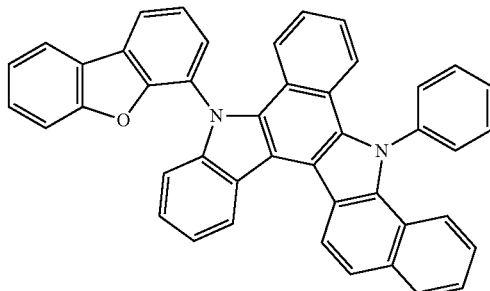

1-6

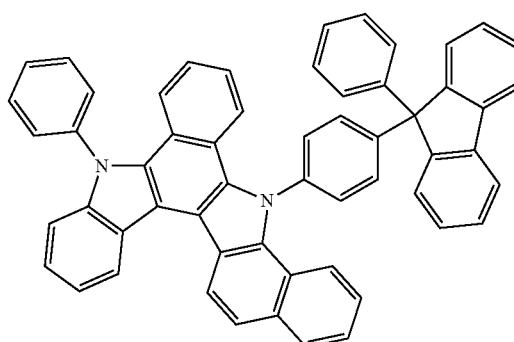

1-7

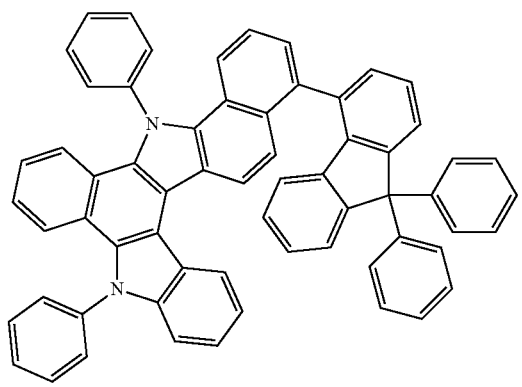

1-8

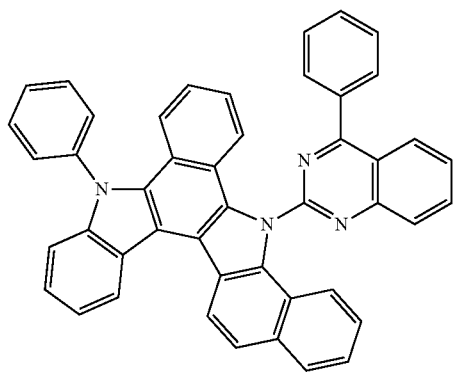

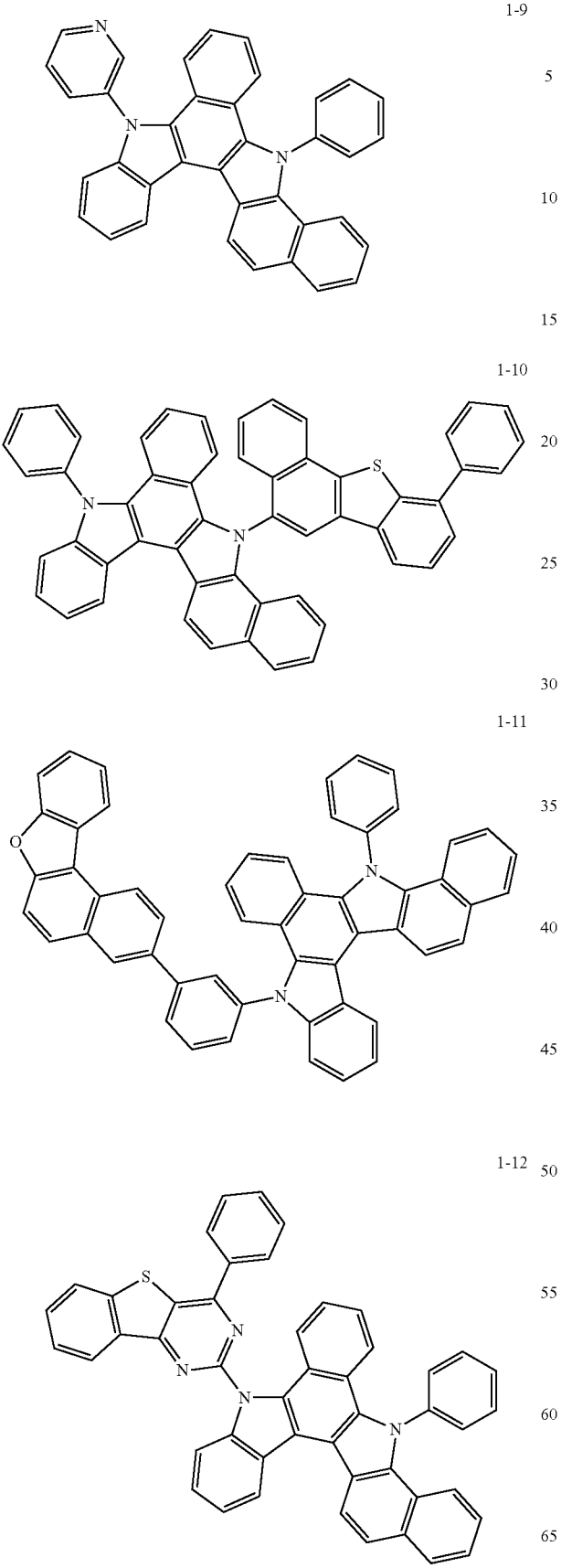
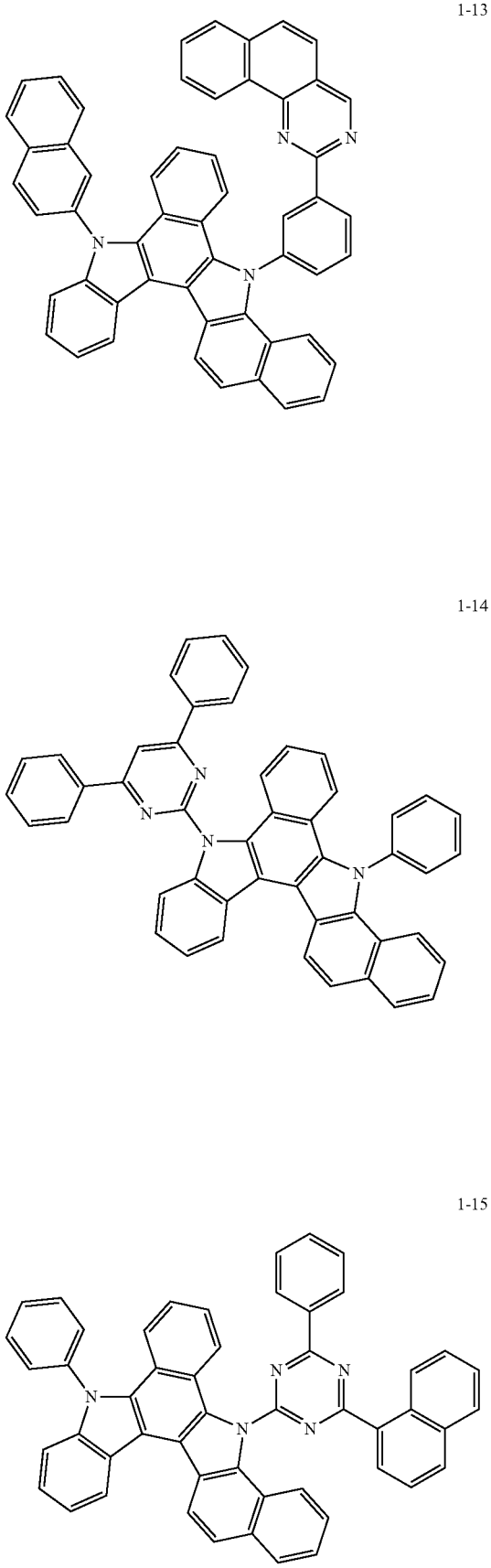

-continued
1-16
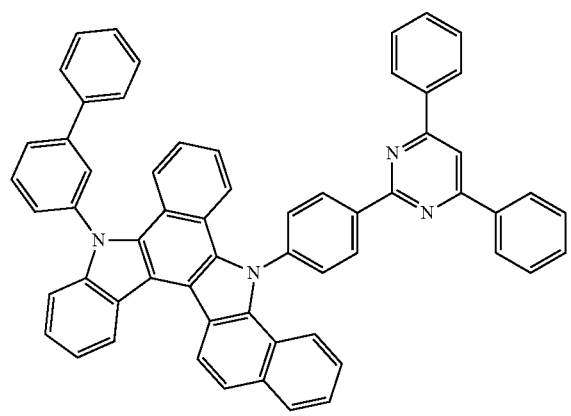
1-17
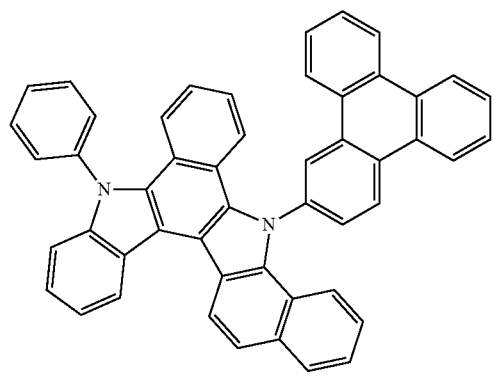
1-18
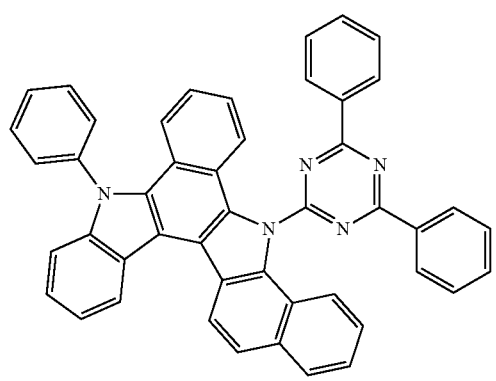
-continued
1-19
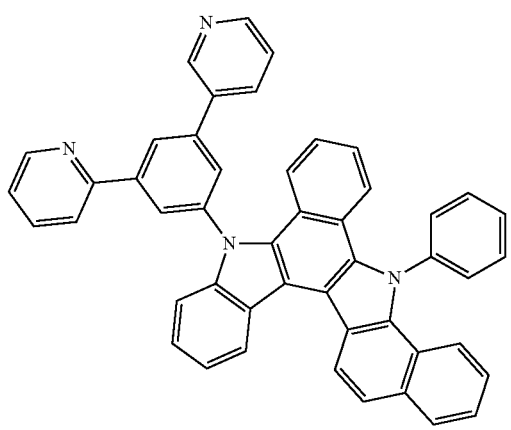
1-20
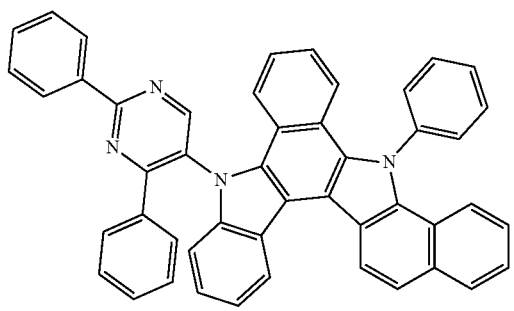
1-21
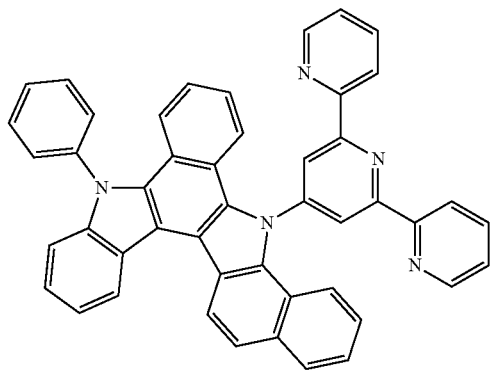
1-22
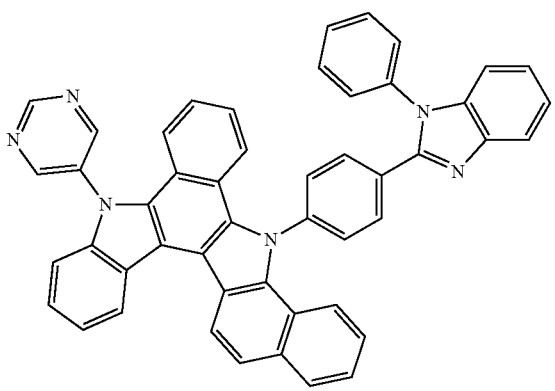

1-23
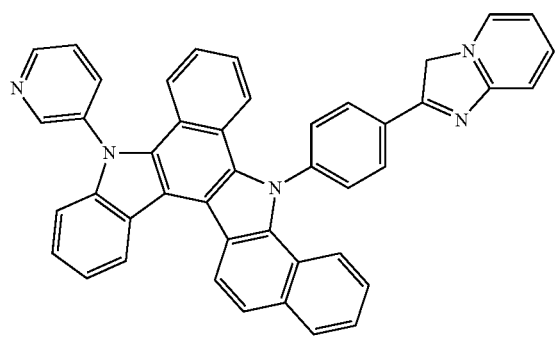
1-24
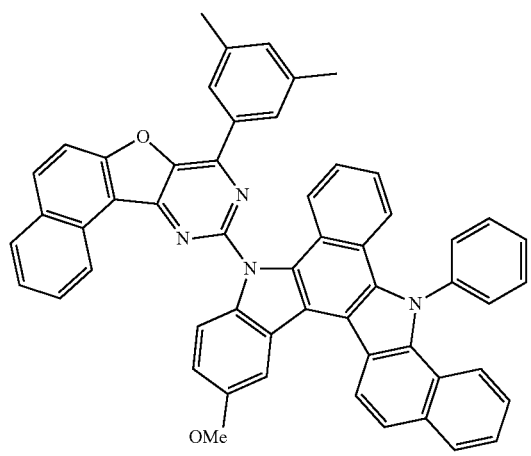
1-25
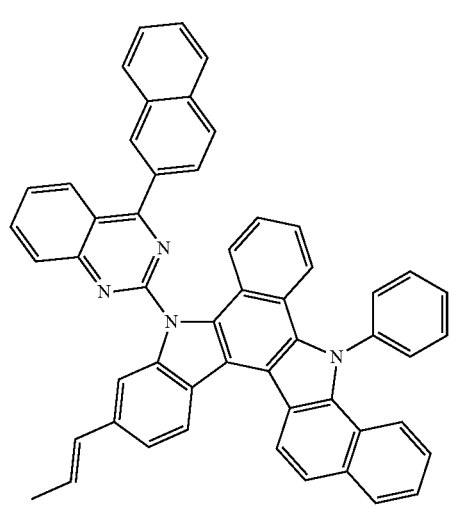
1-26
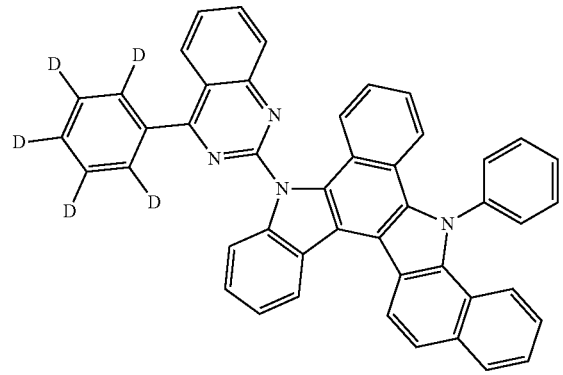
1-27
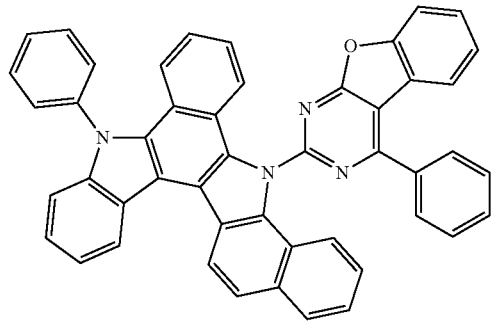
1-28
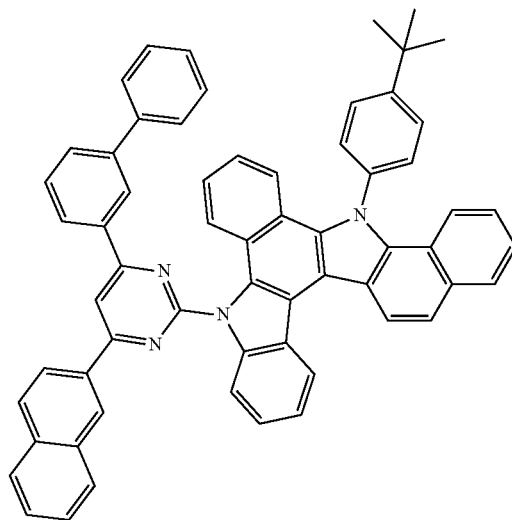

1-29
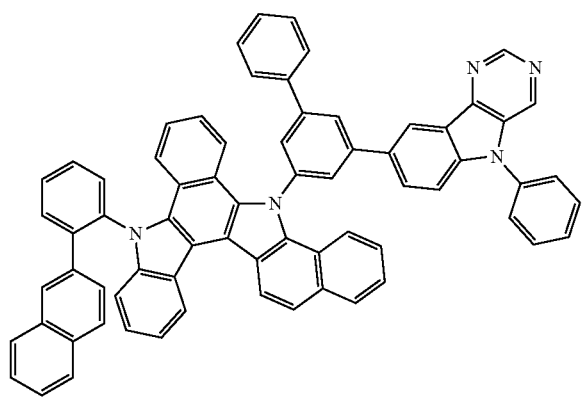
1-30
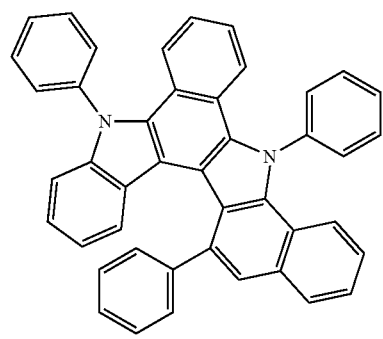
1-31
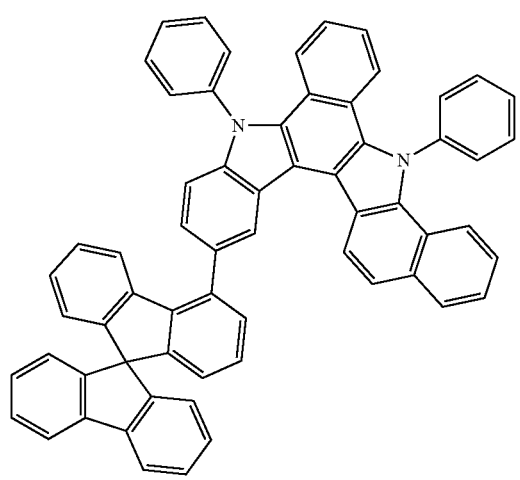
1-32
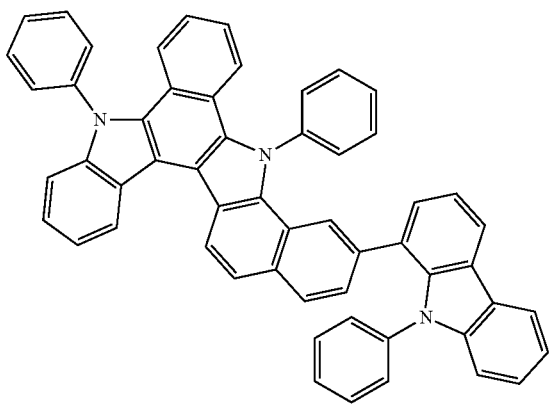
1-33
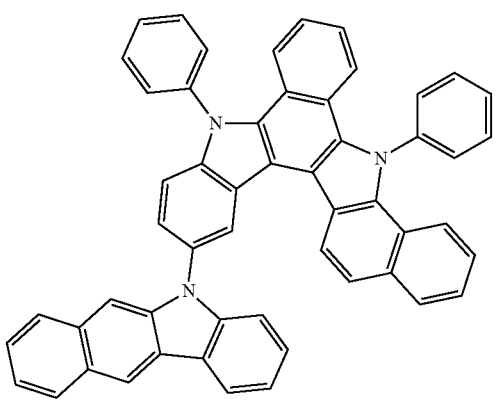
1-34
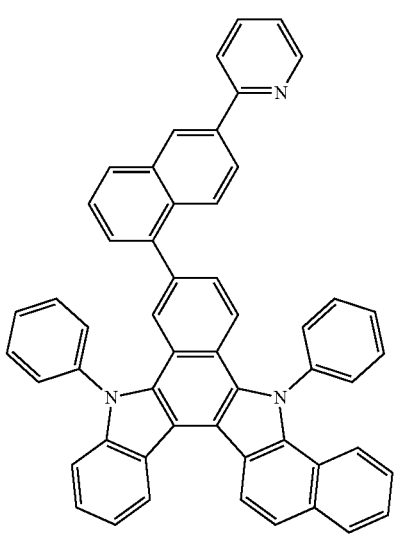

1-35
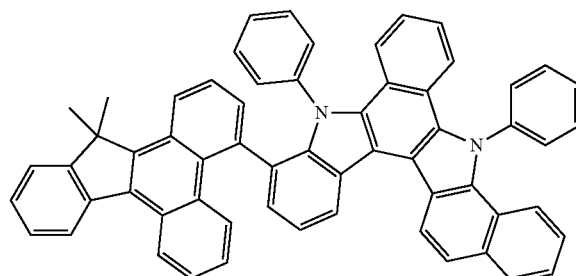
1-36
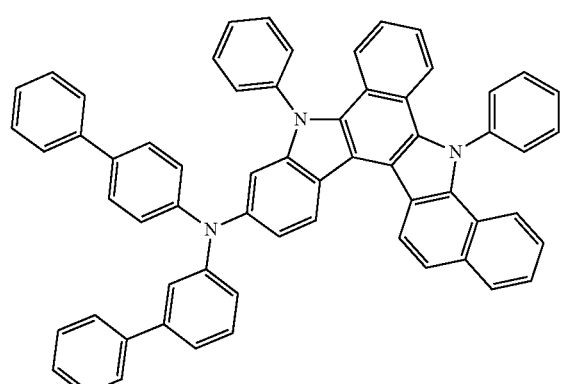
1-37
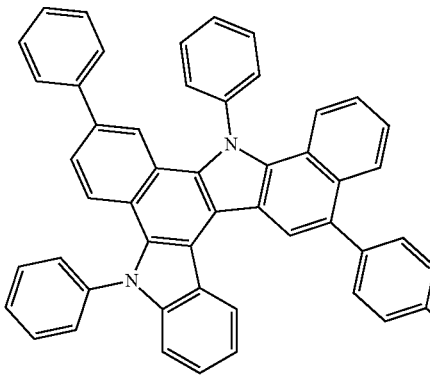
1-38
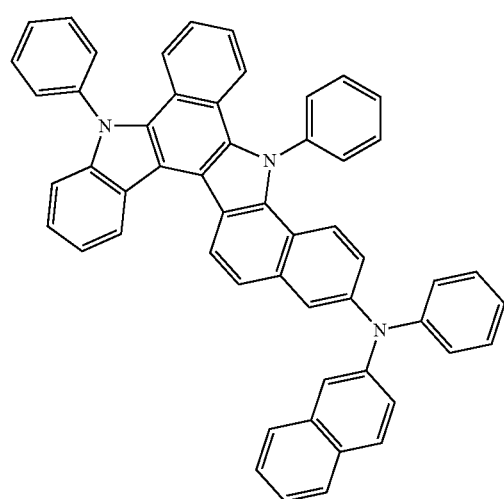
1-39
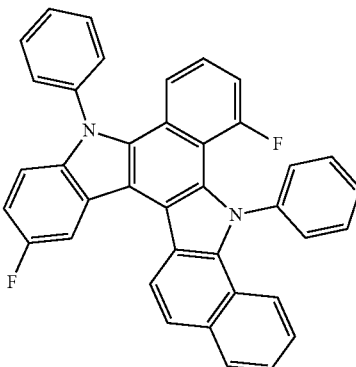
1-40
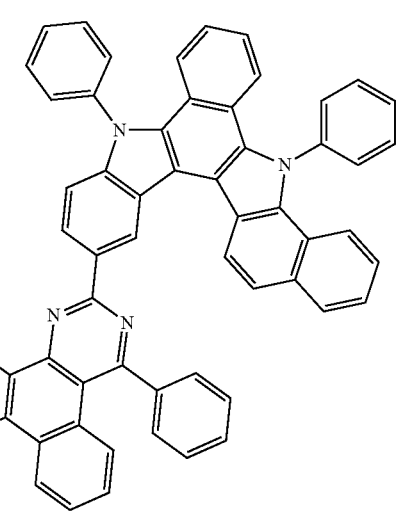
1-41
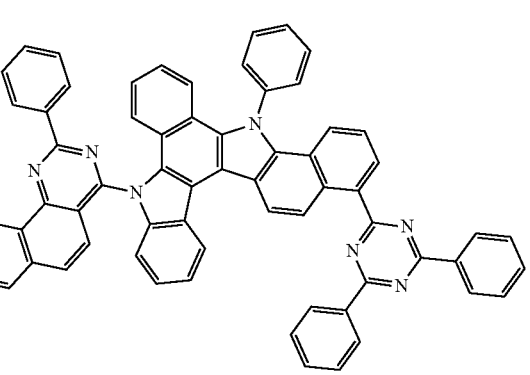
1-42
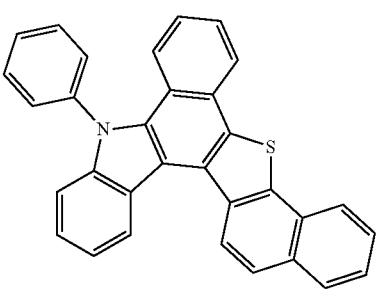

1-43
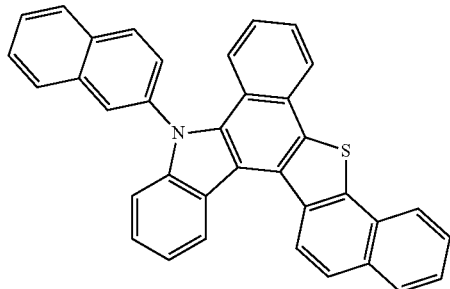
1-44
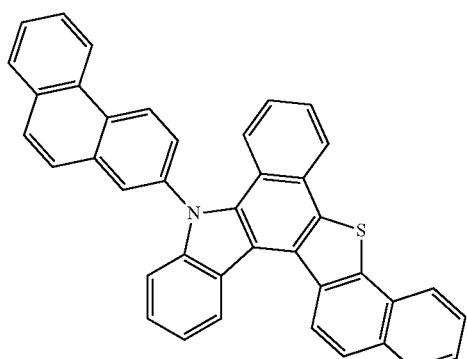
1-45
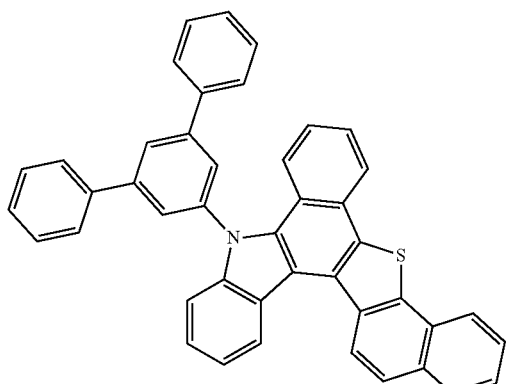
1-46
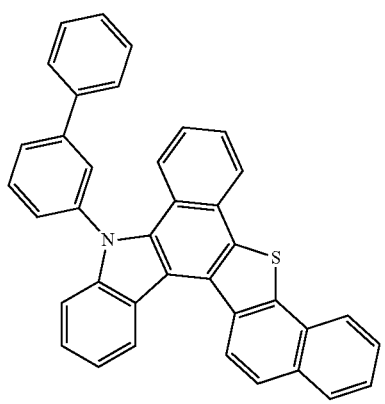
1-47
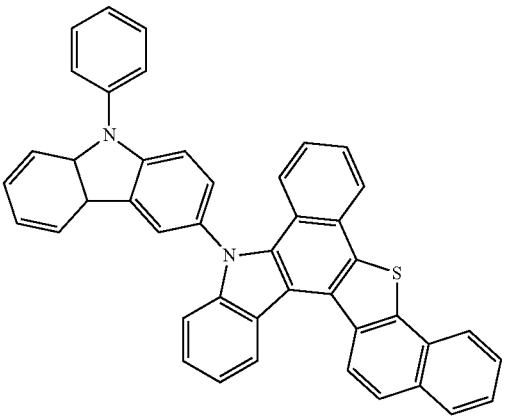
1-48
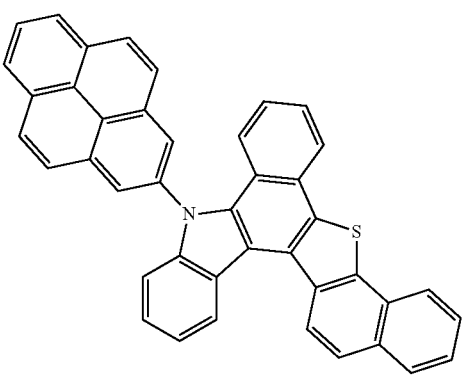
1-49
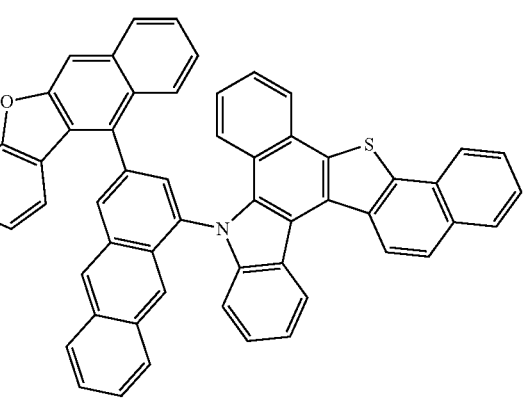
1-50
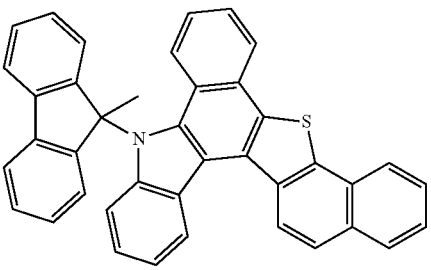

1-51
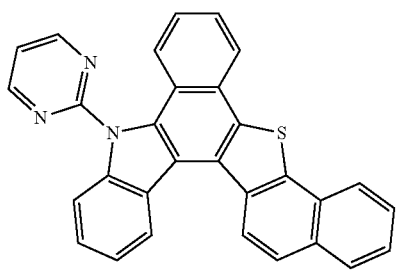
1-52
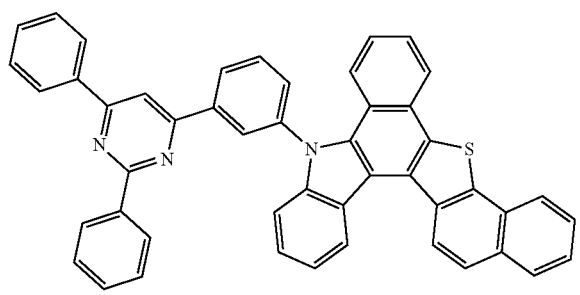
1-53
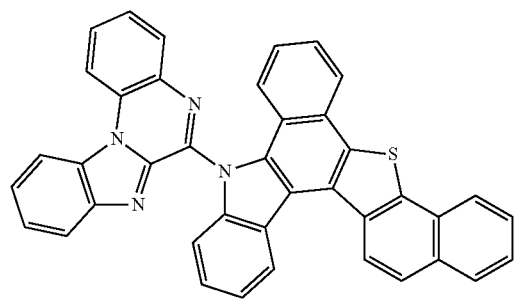
1-54
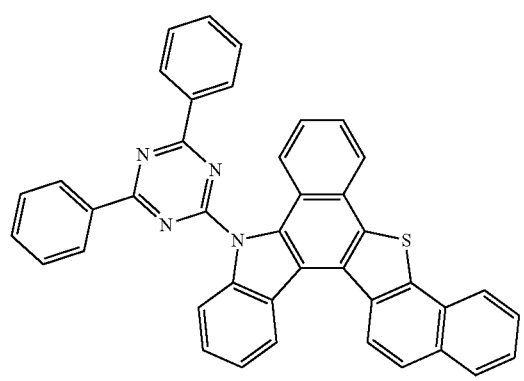
1-55
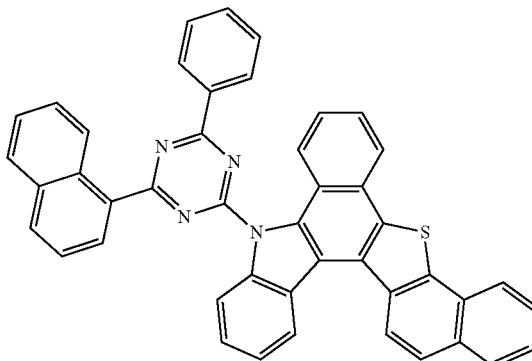
1-56
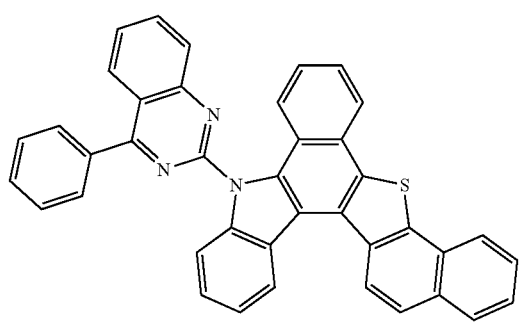
1-57
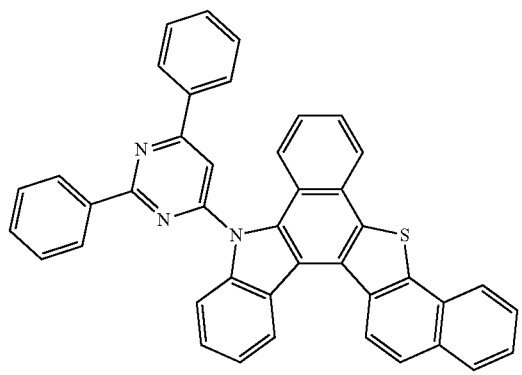
1-58
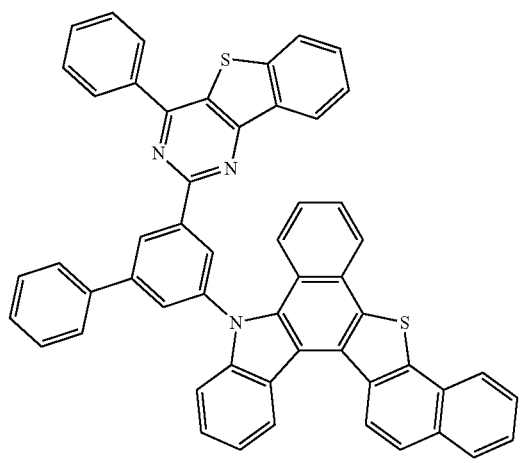

-continued
1-59
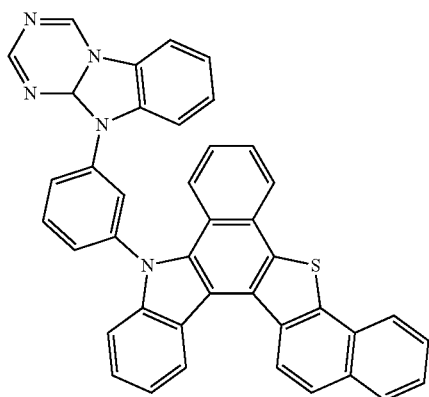
1-60
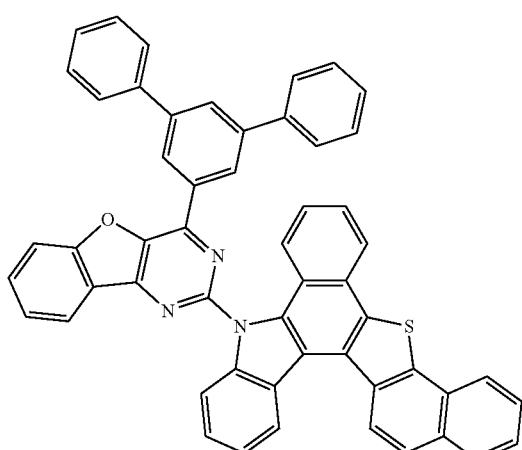
1-61
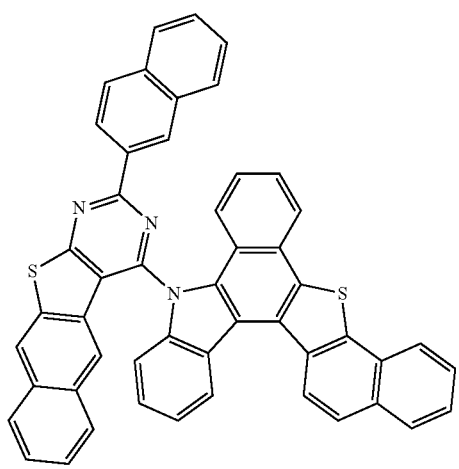
-continued
1-62
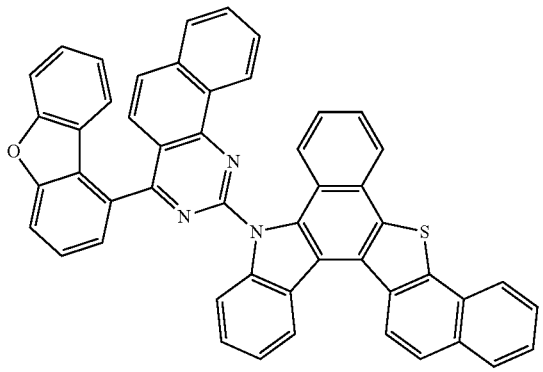
1-63
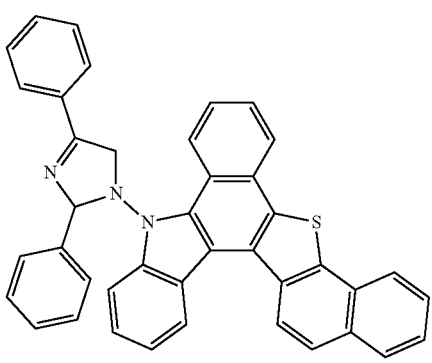
1-64
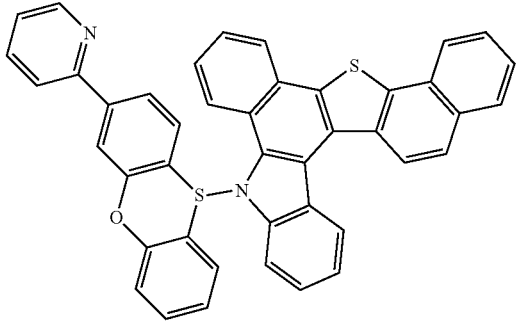
1-65
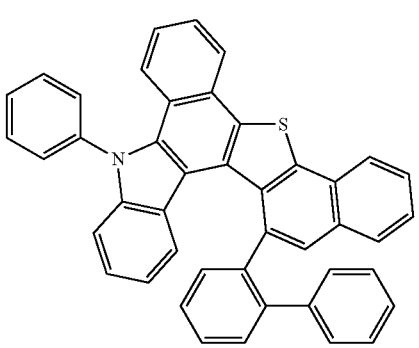

1-66
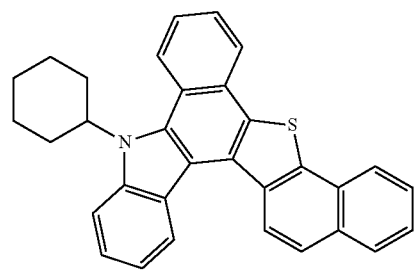
1-67
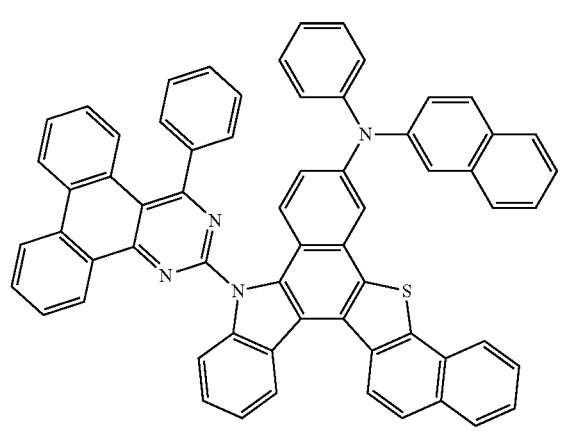
1-68
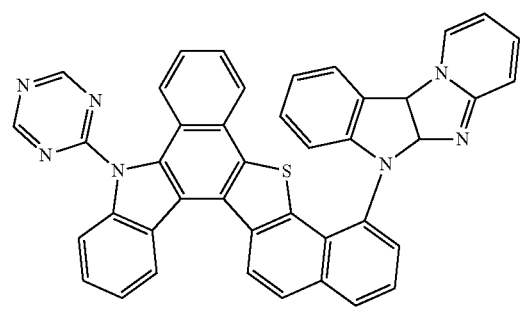
1-69
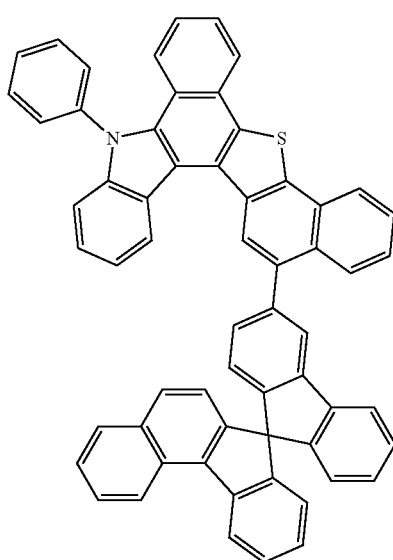
1-70
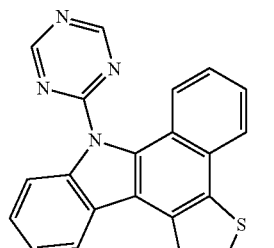
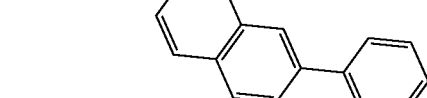
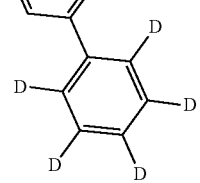
1-71
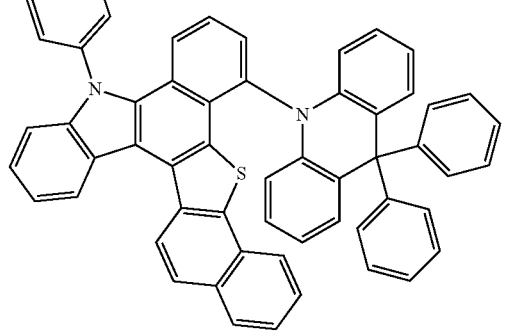
1-72
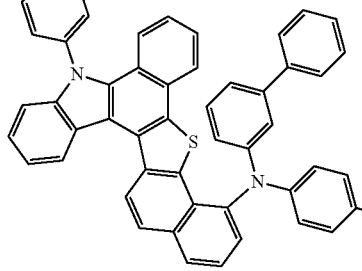

1-73
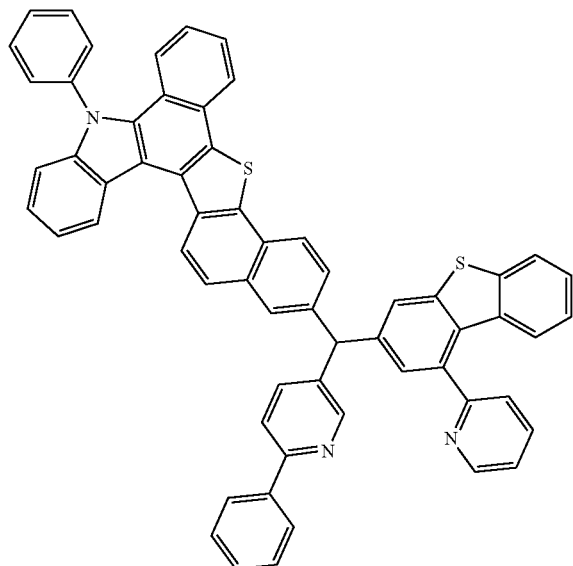
1-74
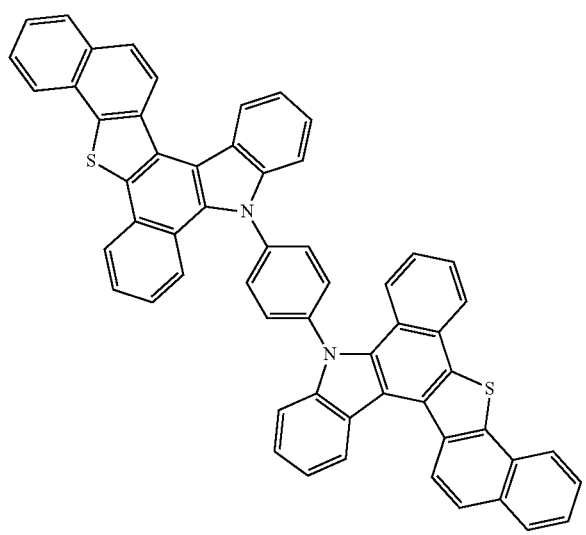
1-75
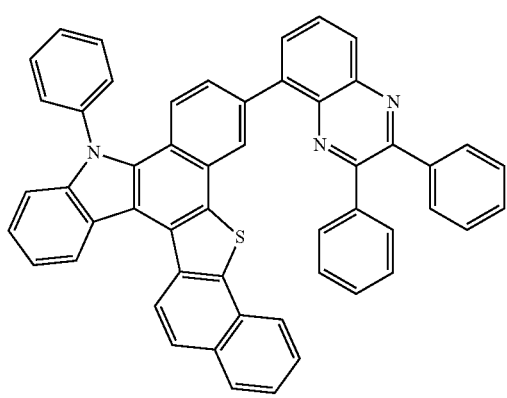
1-76
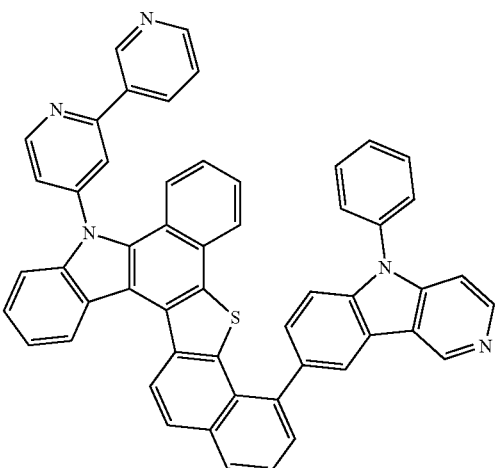
1-77
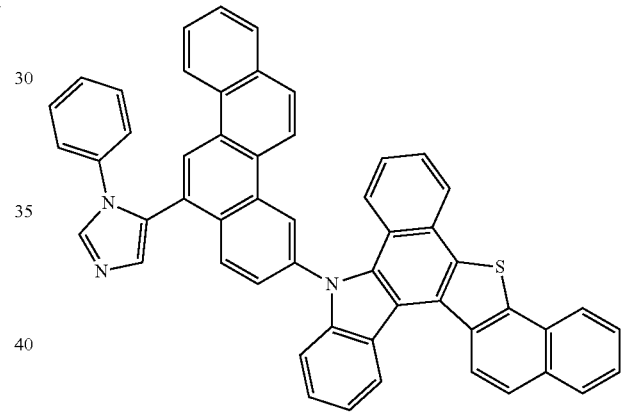
1-78
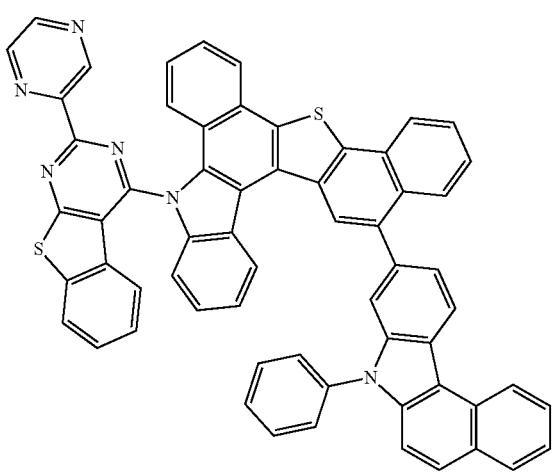

-continued
1-79
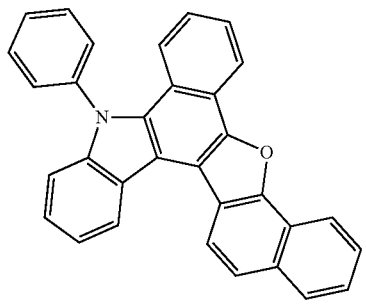
1-80
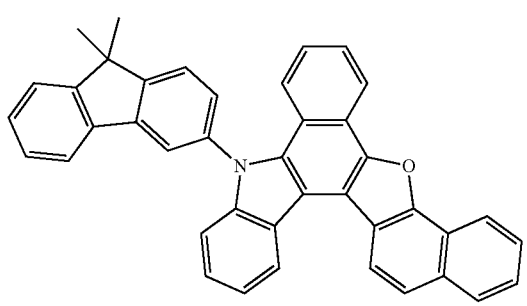
1-81
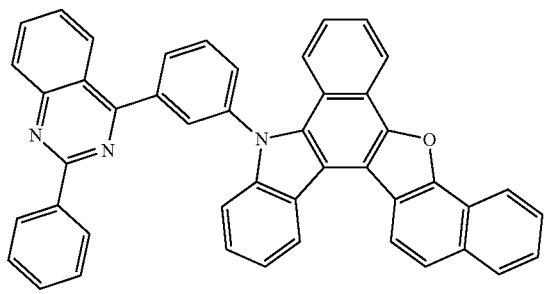
1-82
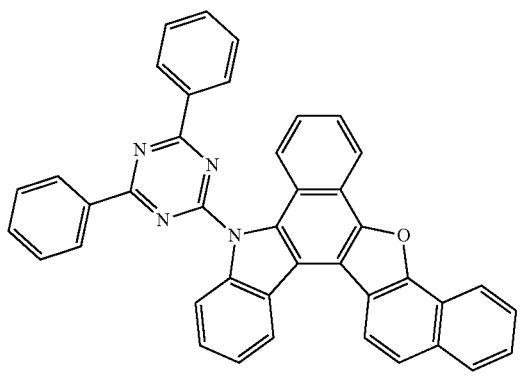
-continued
1-83
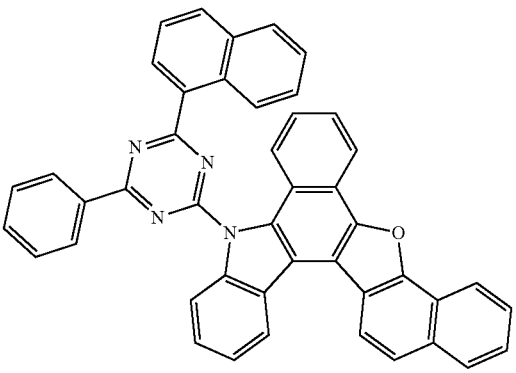
1-84
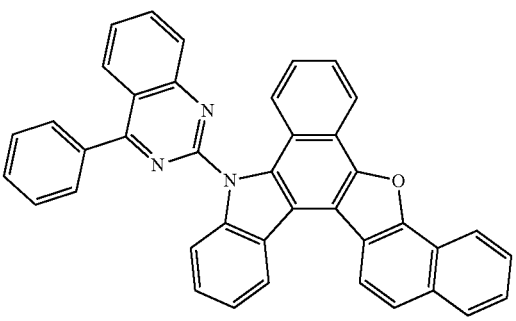
1-85
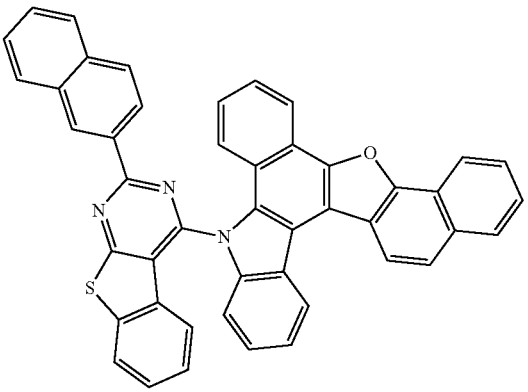
1-86
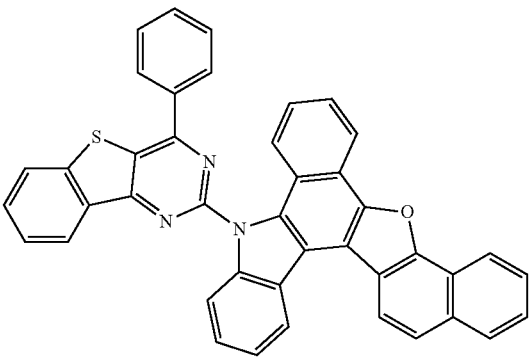

1-87
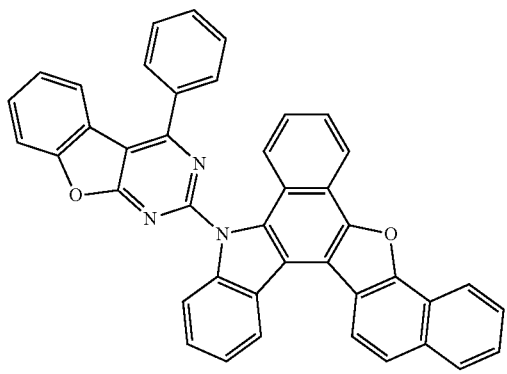
1-88
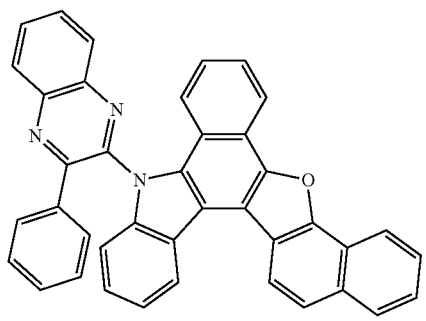
1-89
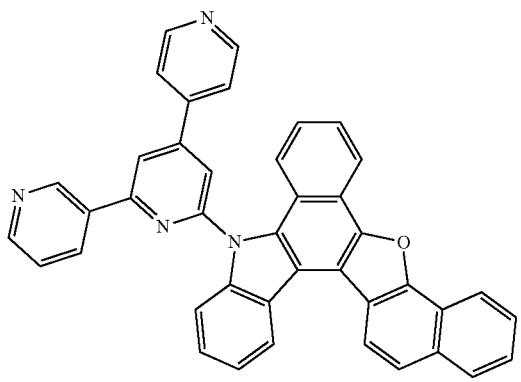
1-90
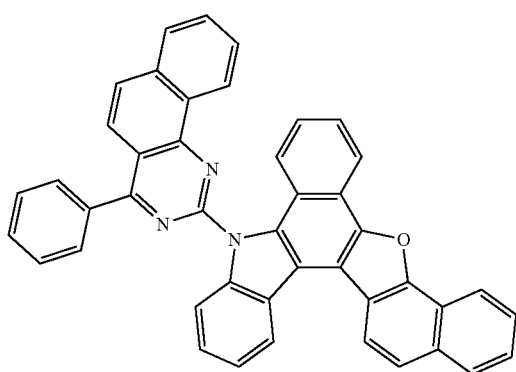
1-91
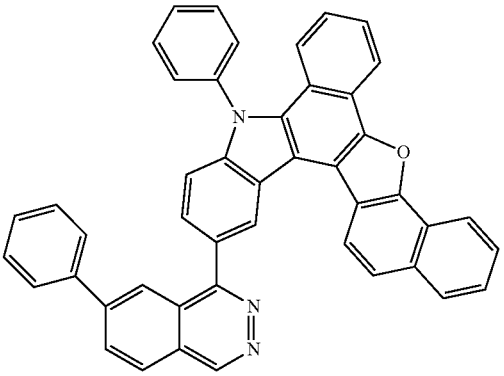
1-92
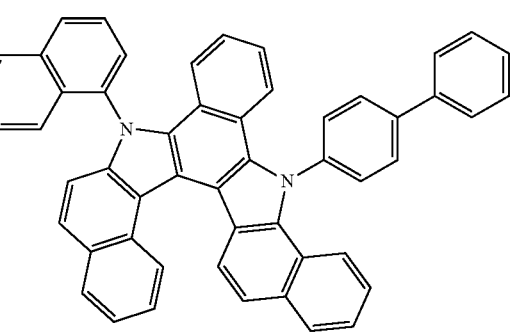
1-93
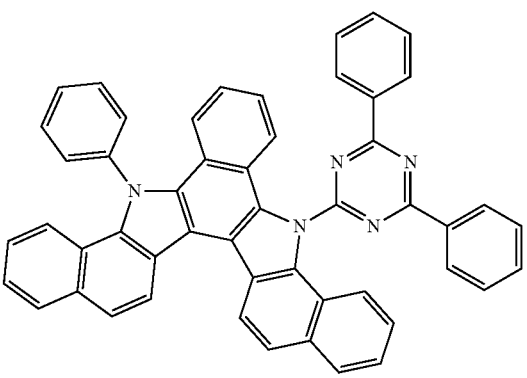
1-94
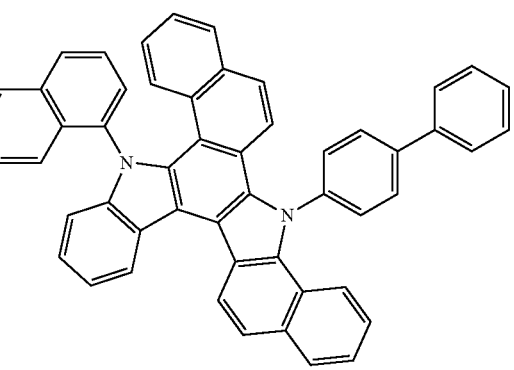

1-95
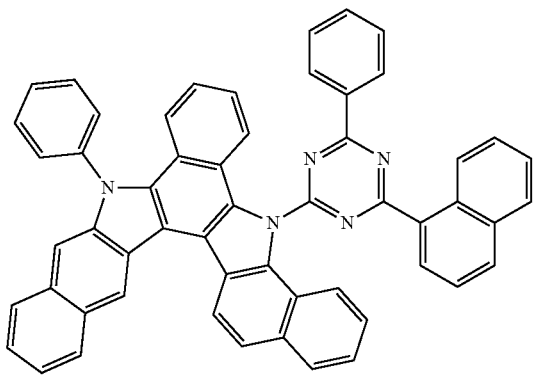
1-96
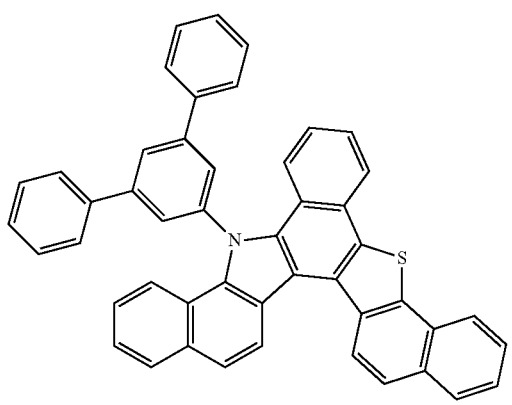
1-97
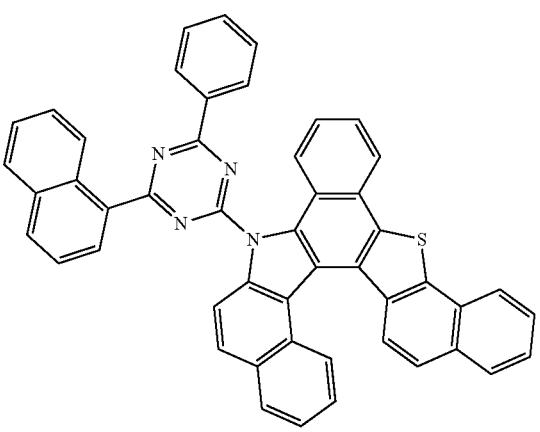
1-98
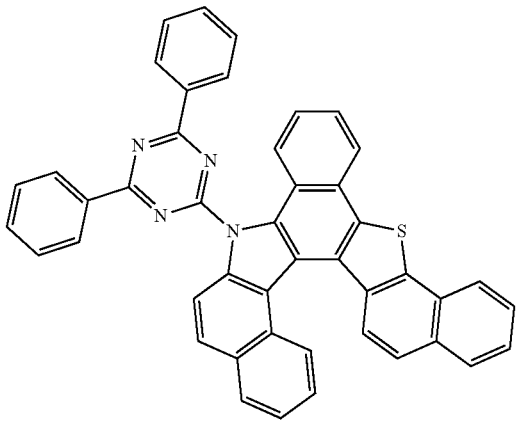
1-99
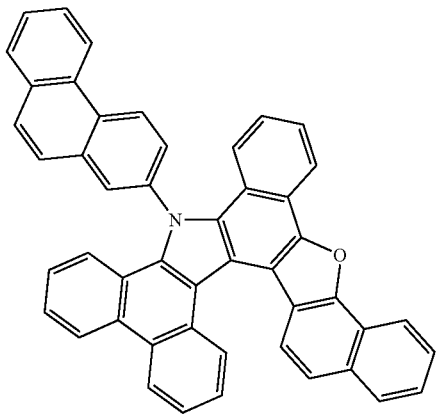
1-100
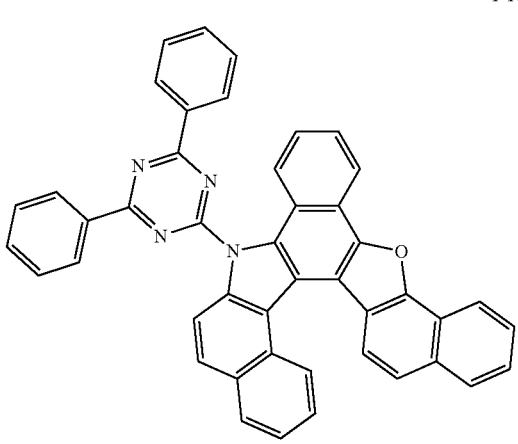

-continued 1-101

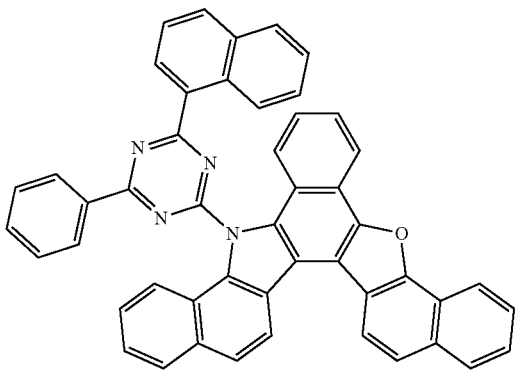

In the above Formulas of the present invention, when $Ar^1$, $Ar^2$, $Ar^3$ and $R^1$, $R^2$, $R^3$ are aryl groups, it is preferably $C_6$-$C_{30}$ aryl group, more preferably $C_6$-$C_{24}$ aryl group, and when $Ar^1$, $Ar^2$, $Ar^3$ and $R^1$, $R^2$, $R^3$ are heterocyclic groups, it is preferably a $C_2$-$C_{40}$ heterocyclic group, more preferably a $C_2$-$C_{30}$ heterocyclic group, still more preferably a $C_2$-$C_{24}$ heterocyclic group.

when $Ar^1$, $Ar^2$, $Ar^3$ and $R^1$, $R^2$, $R^3$ are aryl groups, specific examples thereof include phenyl, biphenyl, terphenyl, quaterphenyl, stylbenyl, naphthyl, anthracenyl, phenanthryl, pyrenyl, perylenyl, klycenyl group, and the like. When $Ar^1$, $Ar^2$, $Ar^3$ and $R^1$, $R^2$, $R^3$ are heterocyclic groups, specific examples thereof include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a pyrazine group, a triazole group, an acridyl group, a pyridazine group, a pyrazinyl group, a quinolinyl group, a quinazolinyl group, a quinoxalinyl group, a benzoquinoxaline, a dibenzoquinoxaline, a phthalazinyl group, a pyridopyrimidinyl group, a pyridopyrazinyl group, a pyrazinopyrazinyl group, an isoquinoline group, an indole group, a carbazole group, indolocarbazole, acridine, phenoxazine, benzopyridazine, benzopyrimidine, carboline, benzocarboline, benzoxazole group, a benzoimidazole group, a benzothiazole group, a benzocarbazole group, a benzothiophene group, dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group and dibenzofuranyl group, thienothiophene, benzothienopyridine, benzothienopyrimidine, benzofuropyrimidine, dimethylbenzoindenopyrimidine, phenanthrofuropyrimidine, naphthofuropyrimidine, naphthothienopyrimidine, dibenzothiophene group, thianthrene, dihydrobenzothiophenopyrazine, dihydrobenzofuropyrazine, and the like, but are not limited thereto.

Also, when $L^1$, $L^2$ and $L^3$ in Formula of the present invention are an arylene group, it may preferably be an $C_6$-$C_{30}$ arylene group, more preferably an $C_6$-$C_{18}$ arylene group, illustratively, it may be phenylene, biphenyl, terphenyl, naphthalene, anthracene, phenanthrene, and the like. Preferably, $L^1$ is a heterocyclic group, it is preferably a $C_2$-$C_{30}$ heterocyclic group, more preferably a $C_2$-$C_{18}$ heterocyclic group, illustratively, it can be dibenzofuran, dibenzothiophene, carbazole, and the like, and when $L^1$ is a fluorenylene group, it can be exemplarily 9,9-dimethyl-9H-fluorene.

Referring to the FIGURE, the organic electric element (100) according to the present invention includes a first electrode (120) formed on a substrate (110), a second electrode (180), and an organic material layer including the compound represented by Formula 1 between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may include a hole injection layer (130), a hole transport layer (140), an emitting layer (150), an electron transport layer (160), and an electron injection layer (170) formed in sequence on the first electrode (120). Here, the remaining layers except the emitting layer (150) may not be formed. The organic material layer may further include a hole blocking layer, an electron blocking layer, an emitting-auxiliary layer (151), an electron transport auxiliary layer, a buffer layer (141), etc., and the electron transport layer (160) and the like may serve as a hole blocking layer.

Although not shown, the organic electric element according to the present invention may further include a protective layer formed on at least one side of the first and second electrodes, which is a side opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

In addition, an emission auxiliary layer (151) may be further formed between the hole transport layer (140) and the emitting layer (150), and an electron transport auxiliary layer may be further formed between the emitting layer (150) and the electron transport layer (160).

In addition, at least one hole transporting band layer is provided between the first electrode and the emitting layer, wherein the hole transporting band layer may include a hole transport layer, an emitting auxiliary layer or both, wherein the hole transporting band layer includes an organic electronic element comprising the compound represented by Formula 1.

The present invention may further include a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

As another specific example, the present invention provides an organic electric element wherein the emitting layer in the organic material layer is a phosphorescent light emitting layer.

The organic electric element according to an embodiment of the present invention may be a front emission type, a back emission type, or a both-sided emission type, depending on the material used.

WOLED (White Organic Light Emitting Device) has advantages of high resolution realization and excellent fairness, and can be manufactured using conventional LCD color filter technology. Various structures for a white organic light emitting device mainly used as a backlight device have been proposed and patented. Representatively, there are side-by-side arrangement of the radiation part of the R (red), G (green) and B (blue), a stacking method in which R, G, and B emitting layers are laminated on top and bottom, electroluminescence by the blue (B) organic emitting layer and, by using the light from this, a color conversion material (CCM) method using a photo-luminescence of an inorganic phosphor, etc., and the present invention may be applied to such WOLED.

The present invention also provides an electronic device comprising a display device including the organic electric element; and a control unit for driving the display device.

According to another aspect, the present invention provides an display device wherein the organic electric element is at least one of an OLED, an organic solar cell, an organic photo conductor, an organic transistor(organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis Examples of the compound represented by Formula 1 of the present invention and preparation examples of the organic electric element of the present invention will be described in detail by way of example, but are not limited to the following examples.

Synthesis Example 1

I. Synthesis of Formula 1

The final products 1 represented by Formula 1 of the present invention can be synthesized by reaction between Sub 1 and Sub 2 as illustrated in the following Reaction Scheme 1.

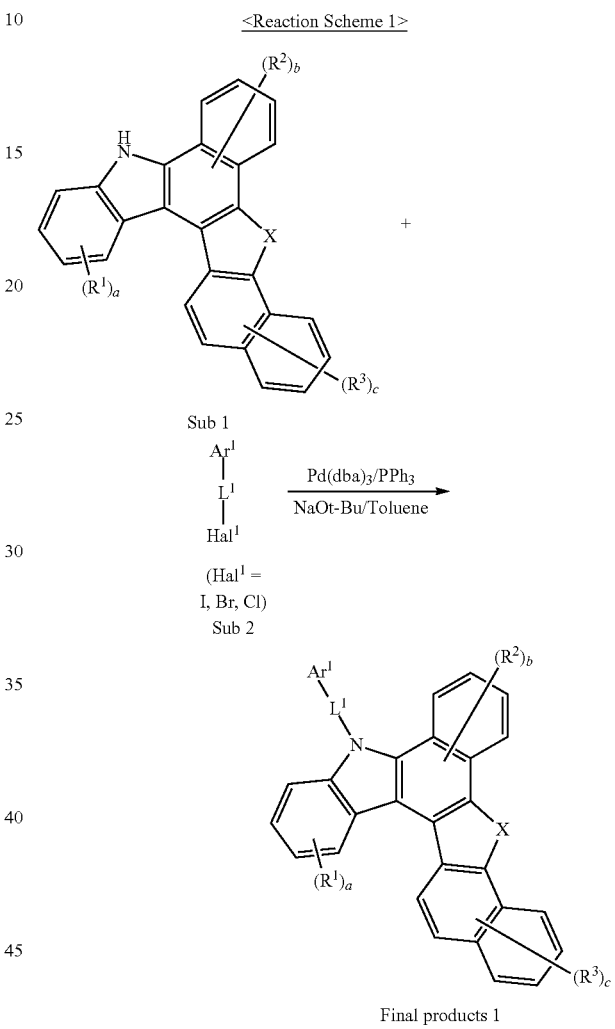

1. Synthesis Example of Sub 1

Sub 1 of reaction scheme 1 can be synthesized by the reaction path of the following reaction scheme 2, but is not limited thereto.

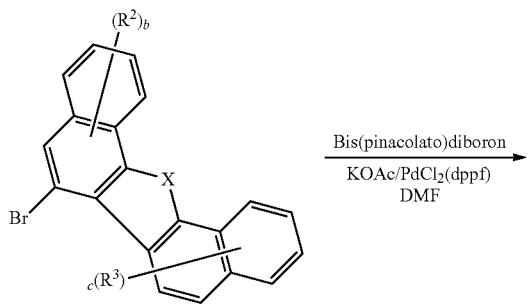

-continued

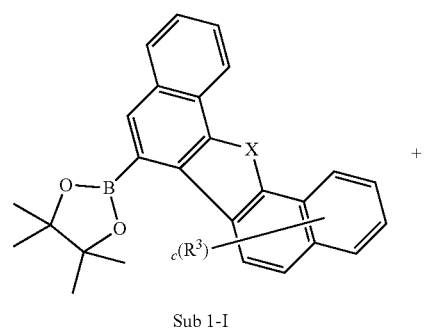

Sub 1-I

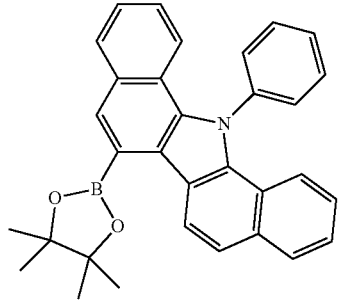

Sub 1-I-1

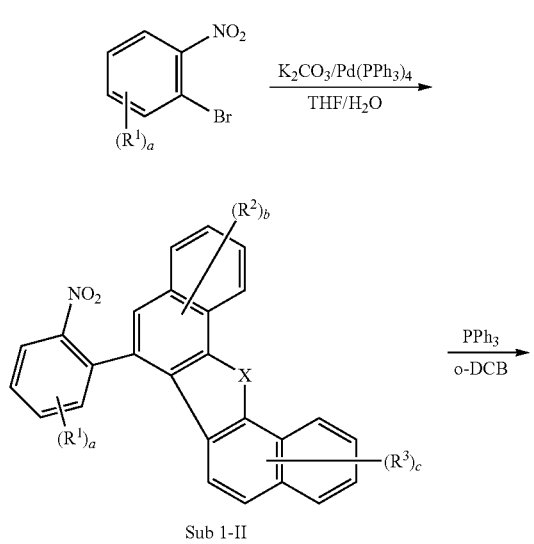

Synthesis Example of Sub 1-1

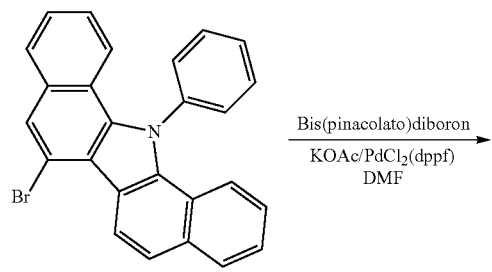

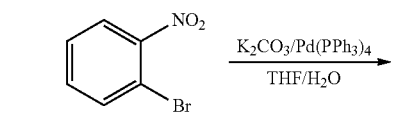

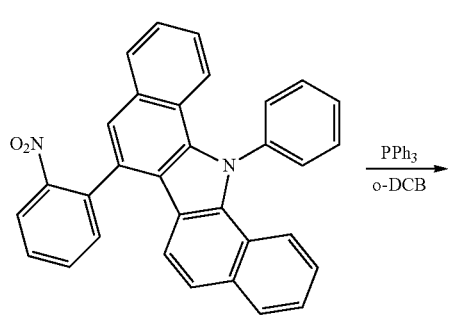

Sub 1-II-1

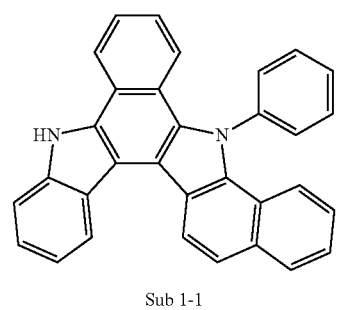

Sub 1-1

(1) Synthesis of Sub 1-I-1

After 13-phenyl-13H-dibenzo[a,i]carbazole (60 g, 142.07 mmol), bis(pinacolato)diboron (39.68 g, 156.28 mmol), KOAc (41.83 g, 426.21 mmol), $PdCl_2$(dppf) (3.48 g, 4.26 mmol) were dissolved in DMF (710 mL), and refluxed at 120° C. for 12 hours. When the reaction was completed, the temperature of the reaction was cooled to room temperature, extracted with $CH_2Cl_2$ and wiped with water. The organic layer was dried over $MgSO_4$ and concentrated. The resulting compound was recrystallized by $CH_2Cl_2$ and methanol solvent to obtain the product. (58.02 g, 87%)

(2) Synthesis of Sub 1-II-1

Sub 1-I-1 (58.02 g, 132.05 mmol), 1-bromo-2-nitrobenzene (40.01 g, 198.07 mmol), $K_2CO_3$ (54.75 g, 396.14 mmol), $P_d(PPh_3)_4$ (6.10 g, 5.28 mmol) were added in a round bottom flask and THF (550 mL) and water (275 mL) were added to dissolve and refluxed at 80° C. for 12 hours. When the reaction was completed, the temperature of the reaction was cooled to room temperature, extracted with CH₂Cl₂ and wiped with water. The organic layer was dried over MgSO₄ and concentrated. The resulting compound was separated by silicagel column chromatography to obtain the product. (46.00 g, 75%)

(3) Synthesis of Sub 1-1

Sub 1-II-1 (46.00 g, 99.03 mmol) and triphenylphosphine (64.93 g, 247.57 mmol) were dissolved in o-dichlorobenzene (866 mL) and refluxed for 24 hours. When the reaction was completed, the solvent was removed using reduced pressure distillation. The resulting compound was separated by silicagel column chromatography and recrystallized to obtain the product. (27.84 g, 65%)

Synthesis of Sub 1-24

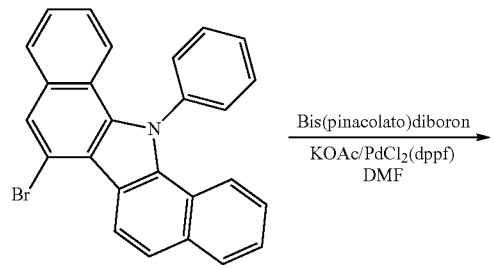

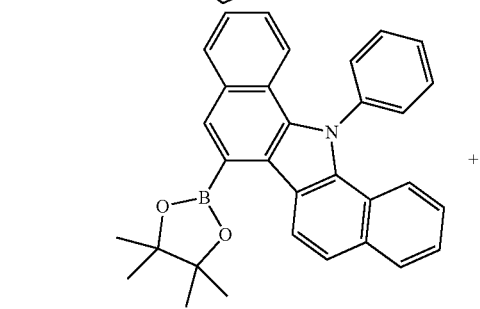

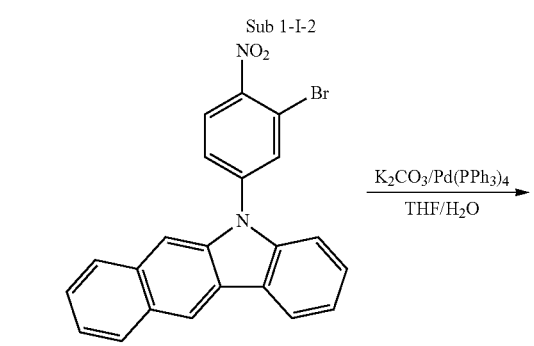

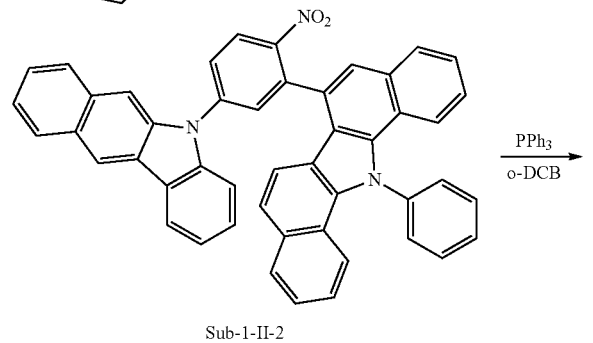

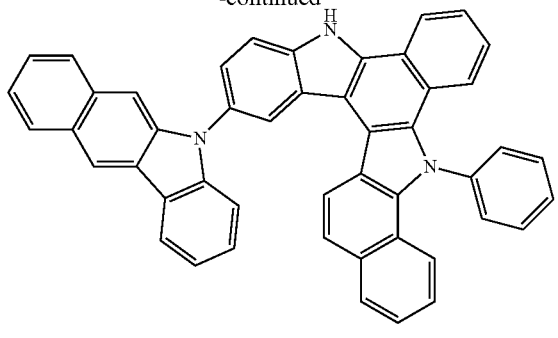

Sub-1-24

(1) Synthesis of Sub 1-I-2

After 13-phenyl-13H-dibenzo[a,i]carbazole (52 g, 123.13 mmol), bis(pinacolato)diboron (34.39 g, 135.44 mmol), KOAc (36.25 g, 369.38 mmol), PdCl₂(dppf) (3.02 g, 3.69 mmol) were dissolved in DMF (616 mL), and refluxed at 120° C. for 12 hours. When the reaction was completed, the temperature of the reaction was cooled to room temperature, extracted with CH₂Cl₂ and wiped with water. The organic layer was dried over MgSO₄ and concentrated. The resulting compound was recrystallized by CH₂Cl₂ and methanol solvent to obtain the product. (49.13 g, 85%)

(2) Synthesis of Sub 1-II-2

Sub 1-I-2 (49.13 g, 104.67 mmol), 5-(3-bromo-4-nitrophenyl)-5H-benzo[b]carbazole (65.51 g, 157.00 mmol), K₂CO₃ (43.40 g, 314.00 mmol), Pd(PPh₃)₄ (4.84 g, 4.19 mmol), THF (436 mL) and water (218 ml) were carried out in the same manner as in Sub 1-II-1 to give the product. (51.23 g, 72%).

(3) Synthesis of Sub 1-24

Sub 1-II-2 (51.23 g, 75.36 mmol), triphenylphosphine (49.42 g, 188.41 mmol) and o-dichlorobenzene (659 mL) were carried out in the same manner as in Sub 1-1 to give the product Sub 1-24. (30.76 g, 63%).

Synthesis of Sub 1-26

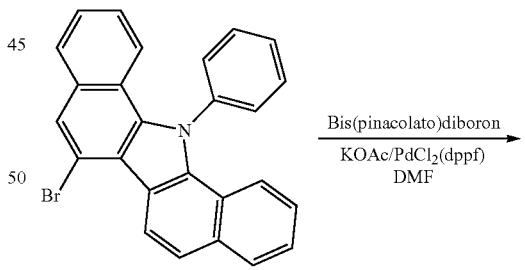

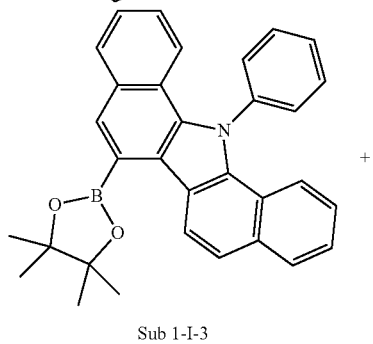

Sub 1-I-3

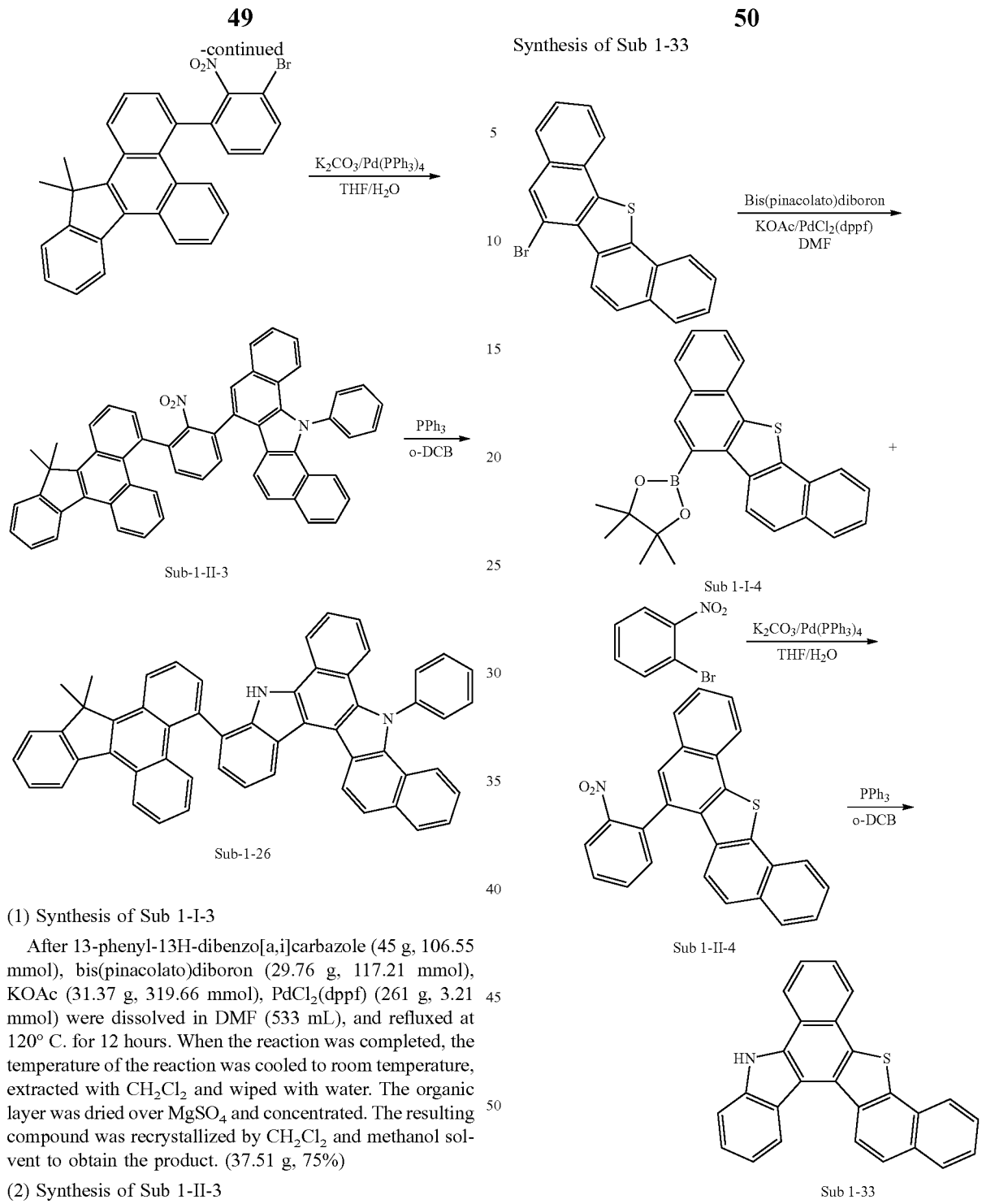

Synthesis of Sub 1-33

(1) Synthesis of Sub 1-I-3

After 13-phenyl-13H-dibenzo[a,i]carbazole (45 g, 106.55 mmol), bis(pinacolato)diboron (29.76 g, 117.21 mmol), KOAc (31.37 g, 319.66 mmol), PdCl$_2$(dppf) (261 g, 3.21 mmol) were dissolved in DMF (533 mL), and refluxed at 120° C. for 12 hours. When the reaction was completed, the temperature of the reaction was cooled to room temperature, extracted with CH$_2$Cl$_2$ and wiped with water. The organic layer was dried over MgSO$_4$ and concentrated. The resulting compound was recrystallized by CH$_2$Cl$_2$ and methanol solvent to obtain the product. (37.51 g, 75%)

(2) Synthesis of Sub 1-II-3

Sub 1-I-3 (37.51 g, 79.91 mmol), 4-(3-bromo-2-nitrophenyl)-13,13-dimethyl-13H-indeno[1,2-I]phenanthrene (59.26 g, 119.87 mmol), K$_2$CO$_3$ (33.13 g, 239.74 mmol), Pd(PPh$_3$)$_4$ (3.69 g, 3.20 mmol), THF (333 mL) and water (166 ml) were carried out in the same manner as in Sub 1-II-1 to give the product. (41.13 g, 68%).

(3) Synthesis of Sub 1-26

Sub 1-II-3 (41.13 g, 54.34 mmol), triphenylphosphine (35.63 g, 135.85 mmol), o-dichlorobenzene (475 mL) were carried out in the same manner as in Sub 1-1 to give the product Sub 1-26. (23.24 g, 59%).

(1) Synthesis of Sub 1-I-4

After dinaphtho[1,2-b:2',1-d]thiophene (60 g, 465.17 mmol), bis(pinacolato)diboron (46.14 g, 181.68 mmol), KOAc (48.63 g, 495.50 mmol), PdCl$_2$(dppf) (4.05 g, 4.92 mmol) were dissolved in DMF (826 mL), and refluxed at 120° C. for 12 hours. When the reaction was completed, the temperature of the reaction was cooled to room temperature, extracted with CH$_2$Cl$_2$ and wiped with water. The organic layer was dried over MgSO$_4$ and concentrated. The resulting compound was recrystallized by CH$_2$Cl$_2$ and methanol solvent to obtain the product. (56.25 g, 83%)

(2) Synthesis of Sub 1-II-4

Sub 1-I-1 (56.25 g, 137.08 mmol), 1-bromo-2-nitrobenzene (41.54 g, 205.62 mmol), K$_2$CO$_3$ (56.84 g, 411.24 mmol), P$_d$(PPh$_3$)$_4$ (6.34 g, 5.48 mmol), THF (571 mL) and water (286 ml) were carried out in the same manner as in Sub 1-II-1 to give the product. (43.35 g, 78%).

(3) Synthesis of Sub 1-33

Sub 1-II-4 (43.35 g, 106.91 mmol), triphenylphosphine (70.11 g, 267.28 mmol), o-dichlorobenzene (935 mL) were carried out in the same manner as in Sub 1-1 to give the product Sub 1-33. (27.95 g, 70%).

Synthesis of Sub 1-45

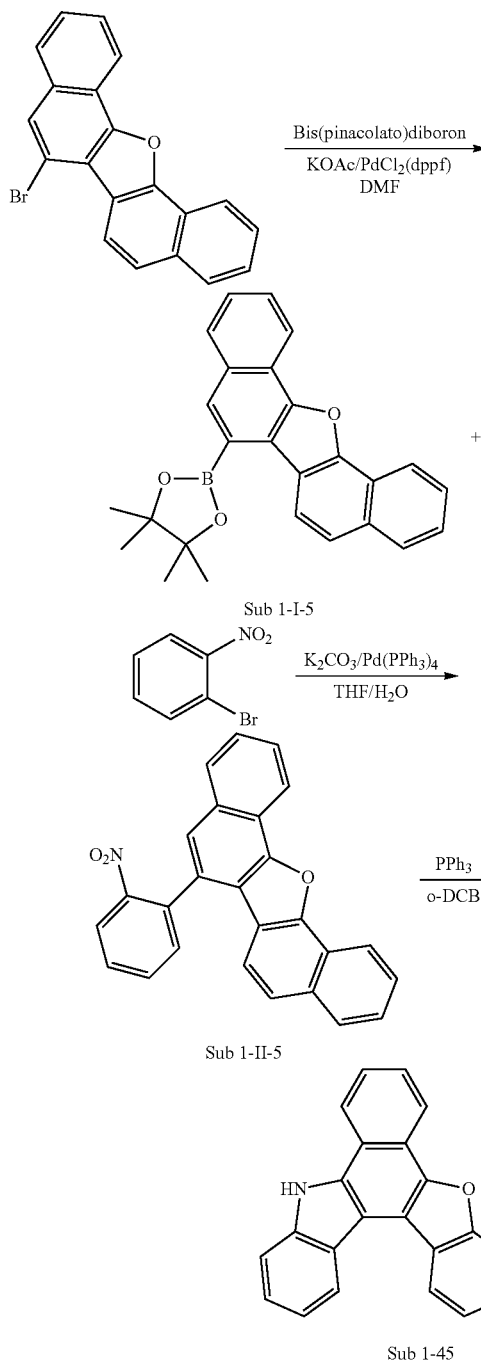

(1) Synthesis of Sub 1-I-5

After dinaphtho[1,2-b:2',1-d]furan (60 g, 223.61 mmol), bis(pinacolato)diboron (62.46 g, 245.97 mmol), KOAc (65.84 g, 670.84 mmol), PdCl$_2$(dppf) (5.48 g, 6.71 mmol) were dissolved in DMF (1118 mL), and refluxed at 120° C. for 12 hours. When the reaction was completed, the temperature of the reaction was cooled to room temperature, extracted with CH$_2$Cl$_2$ and wiped with water. The organic layer was dried over MgSO$_4$ and concentrated. The resulting compound was recrystallized by CH$_2$Cl$_2$ and methanol solvent to obtain the product. (68.77 g, 78%)

(2) Synthesis of Sub 1-II-5

Sub 1-I-1 (68.77 g, 174.42 mmol), 1-bromo-2-nitrobenzene (52.85 g, 261.63 mmol), K$_2$CO$_3$ (72.32 g, 523.26 mmol), P$_d$(PPh$_3$)$_4$ (8.06 g, 6.98 mmol), THF (727 mL) and water (363 ml) were carried out in the same manner as in Sub 1-II-1 to give the product. (49.58 g, 73%).

(3) Synthesis of Sub 1-45

Sub 1-II-5 (49.58 g, 127.32 mmol), triphenylphosphine (83.49 g, 318.30 mmol), o-dichlorobenzene (1114 mL) were carried out in the same manner as in Sub 1-1 to give the product Sub 1-45. (30.94 g, 68%).

Synthesis of Sub 1-46

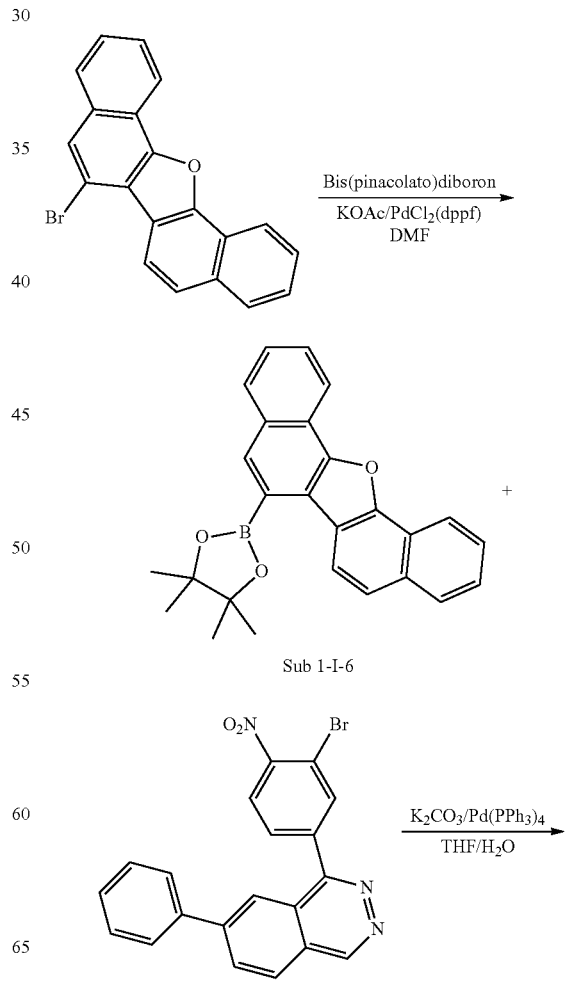

-continued

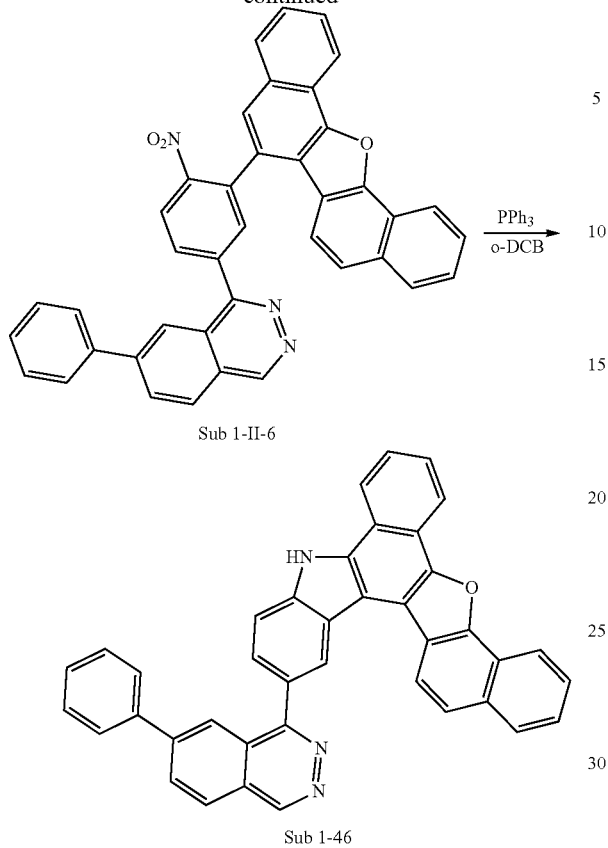

Sub 1-II-6

Sub 1-46

(1) Synthesis of Sub 1-I-6

After dinaphtho[1,2-b:2',1-d]furan (55 g, 204.98 mmol), bis(pinacolato)diboron (57.26 g, 225.48 mmol), KOAc (60.35 g, 614.94 mmol), PdCl$_2$(dppf) (5.02 g, 6.15 mmol) were dissolved in DMF (1025 mL), and refluxed at 120° C. for 12 hours. When the reaction was completed, the temperature of the reaction was cooled to room temperature, extracted with CH$_2$Cl$_2$ and wiped with water. The organic layer was dried over MgSO$_4$ and concentrated. The resulting compound was recrystallized by CH$_2$Cl$_2$ and methanol solvent to obtain the product. (58.19 g, 72%)

(2) Synthesis of Sub 1-II-6

Sub 1-I-1 (58.19 g, 204.98 mmol), 1-(3-bromo-4-nitrophenyl)-7-phenylphthalazine (89.93 g, 221.38 mmol), K$_2$CO$_3$ (61.19 g, 442.76 mmol), Pd(PPh$_3$)$_4$ (6.82 g, 5.90 mmol), THF (615 mL) and water (307 ml) were carried out in the same manner as in Sub 1-II-1 to give the product. (59.58 g, 68%).

(3) Synthesis of Sub 1-46

Sub 1-II-6 (59.58 g, 100.36 mmol), triphenylphosphine (65.81 g, 250.91 mmol), o-dichlorobenzene (878 mL) were carried out in the same manner as in Sub 1-1 to give the product Sub 1-46. (36.64 g, 65%).

The compounds belonging to Sub 1 may be, but not limited to, the following compounds, and Table 1 shows FD-MS (Field Desorption-Mass Spectrometry) values of Sub 1 compounds.

Examples of Sub 1 include, but are not limited to, the followings.

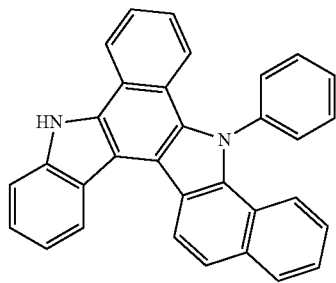

Sub 1-1

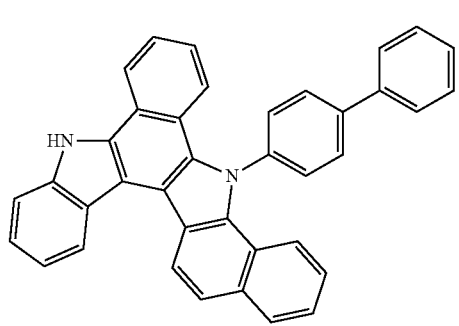

Sub 1-2

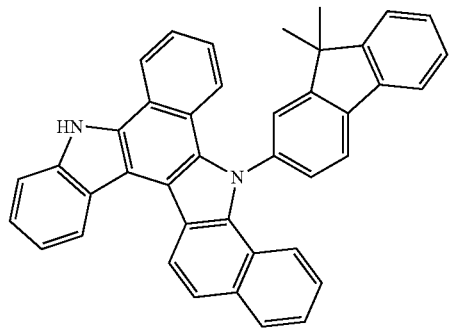

Sub 1-3

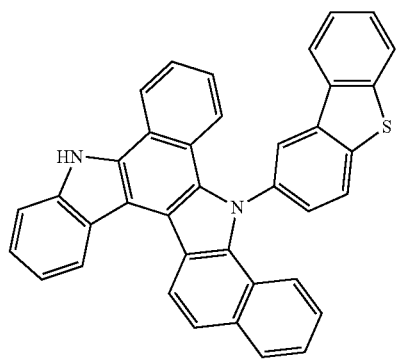

Sub 1-4

Sub 1-5
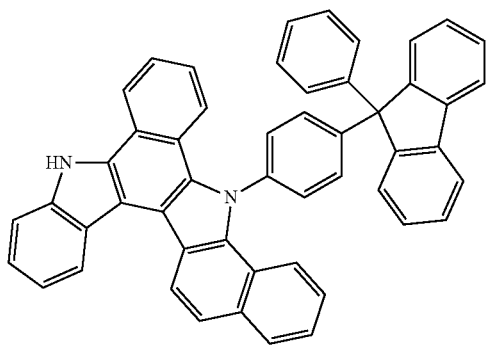
Sub 1-8
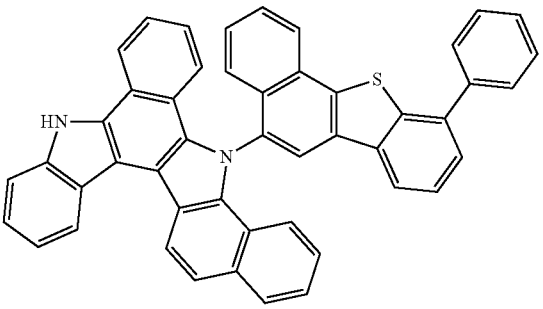
Sub 1-6
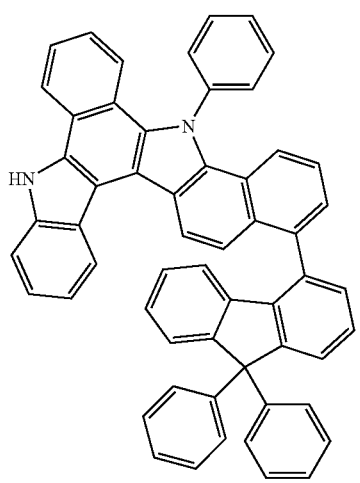
Sub 1-9
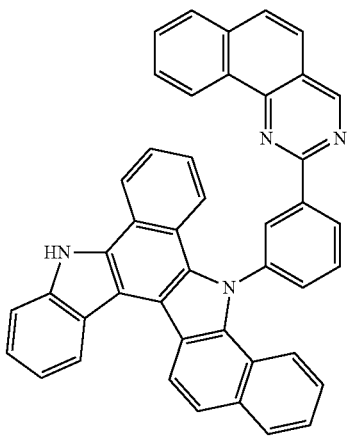
Sub 1-7
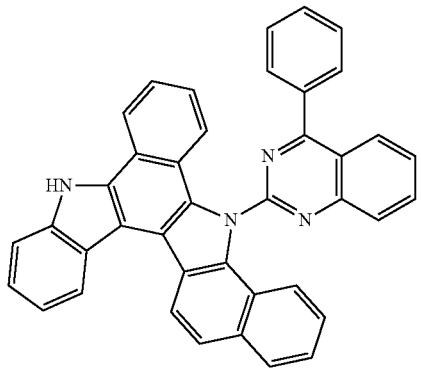
Sub 1-10
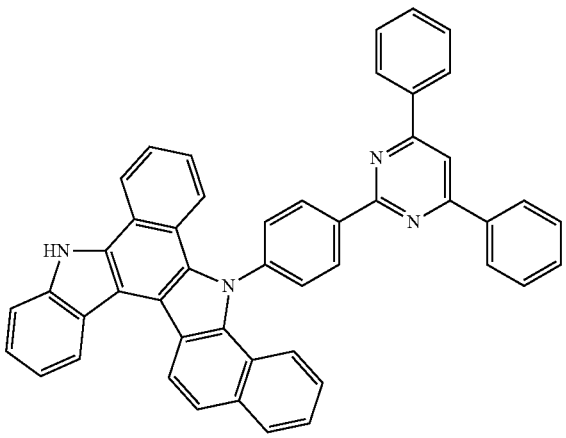

-continued
Sub 1-11
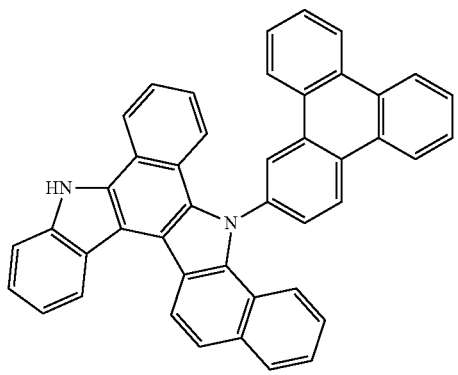
Sub 1-12
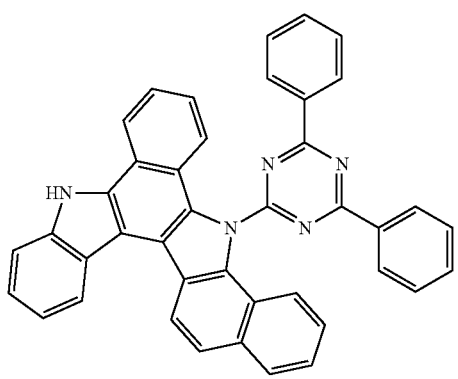
Sub 1-13
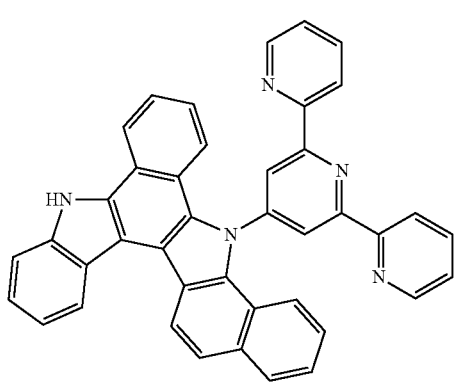
-continued
Sub 1-14
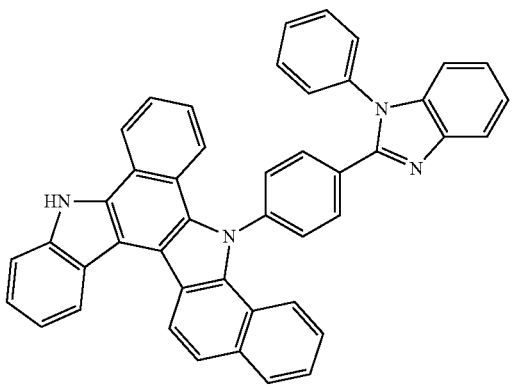
Sub 1-15
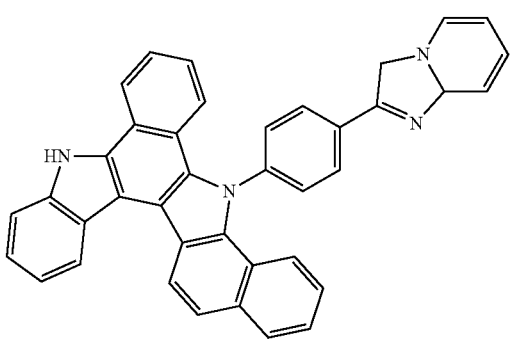
Sub 1-16
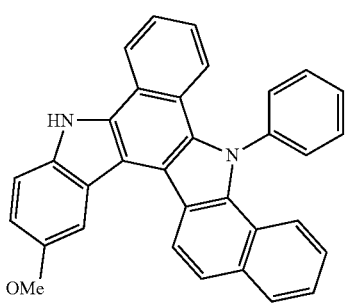

Sub 1-17
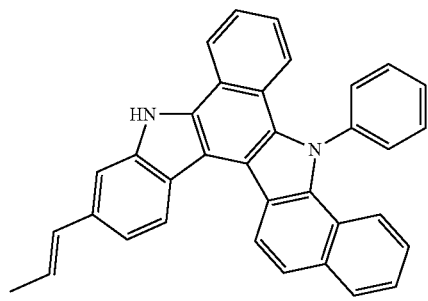
Sub 1-18
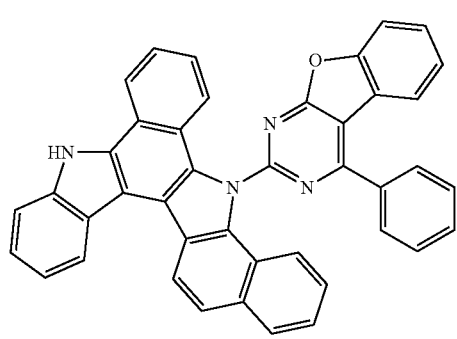
Sub 1-19
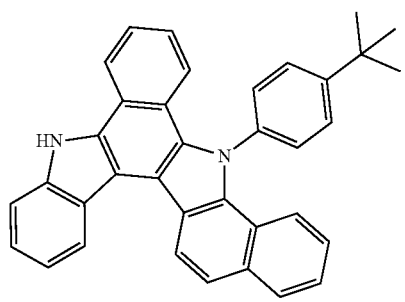
Sub 1-20
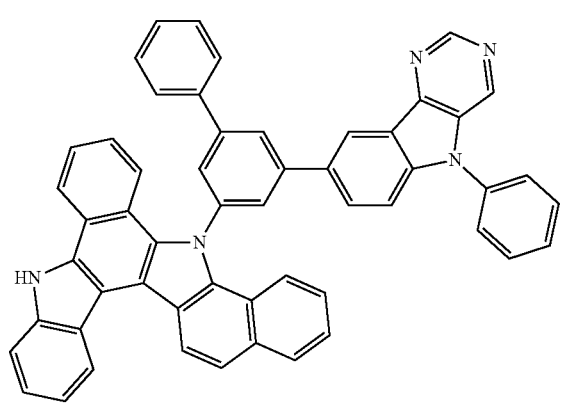
Sub 1-21
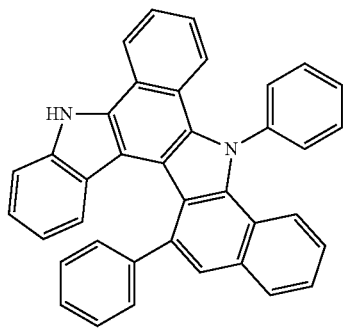
Sub 1-22
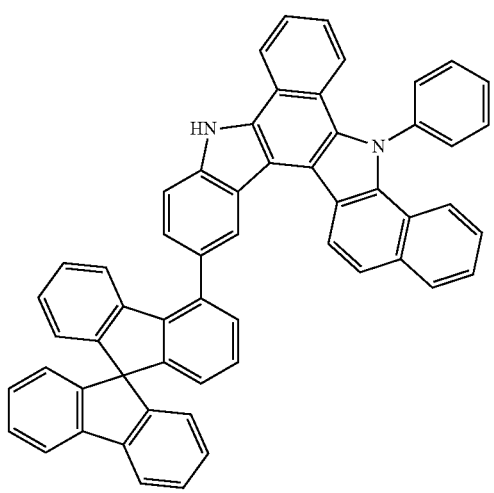
Sub 1-23
Sub 1-24
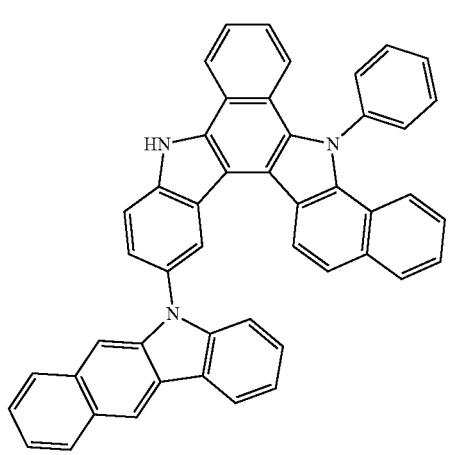

Sub 1-25
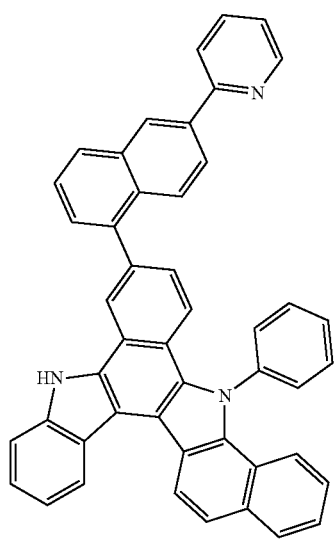
Sub 1-27
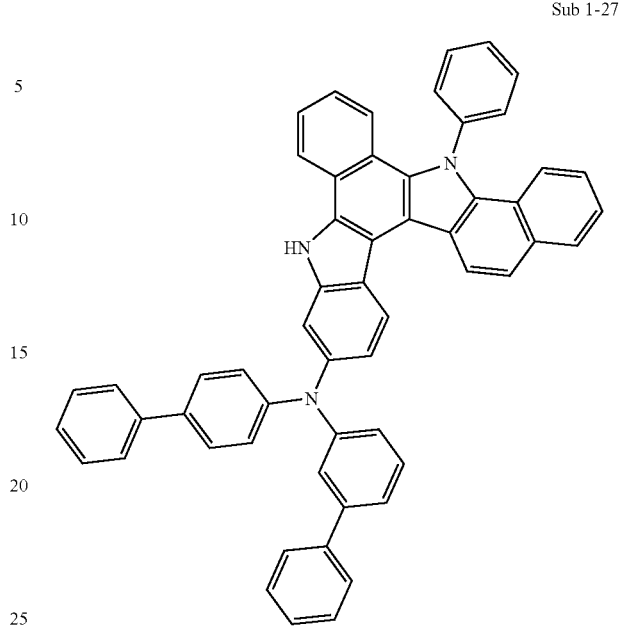
Sub 1-26
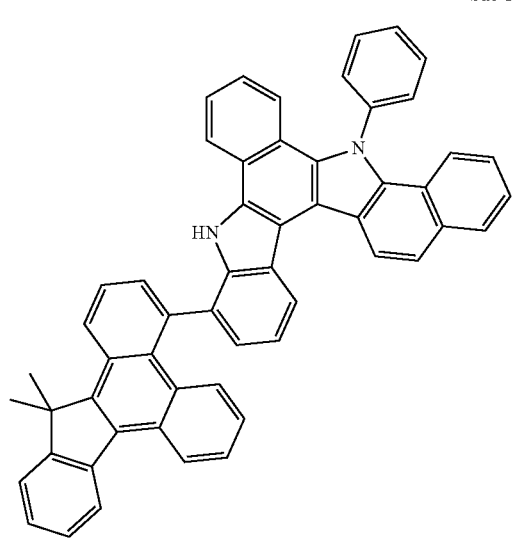
Sub 1-28
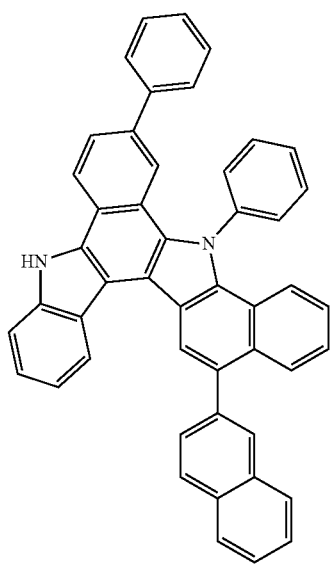

Sub 1-29
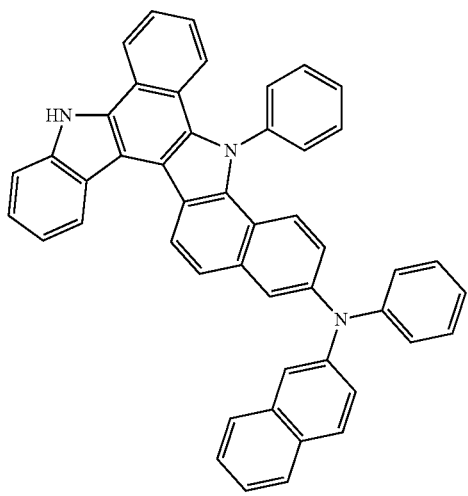
Sub 1-30
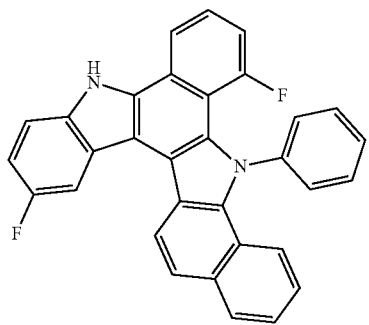
Sub 1-31
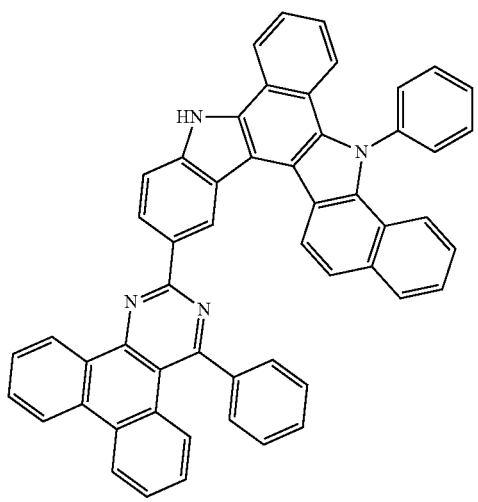
Sub 1-32
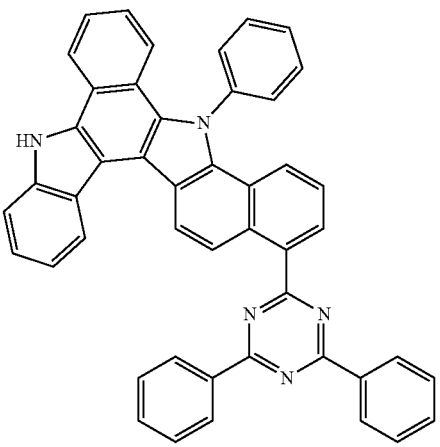
Sub 1-33
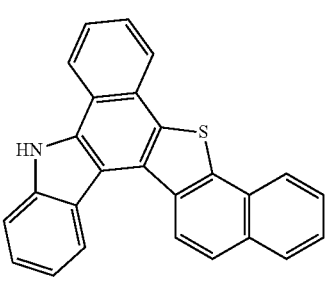
Sub 1-34
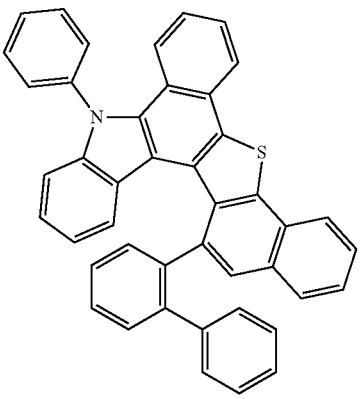
Sub 1-35
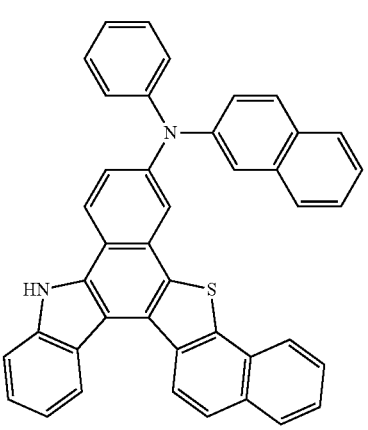

Sub 1-36
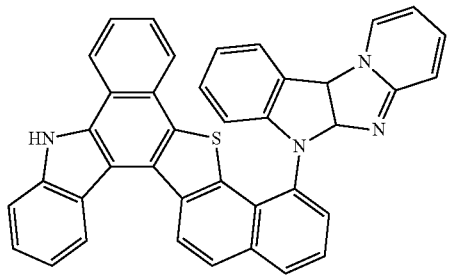
Sub 1-39
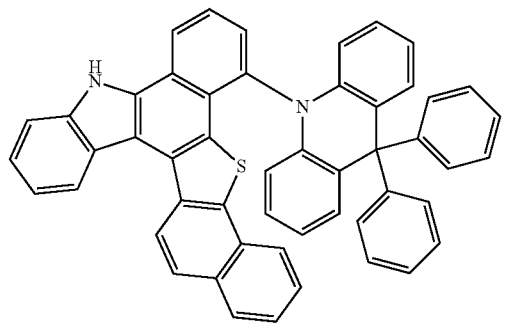
Sub 1-37
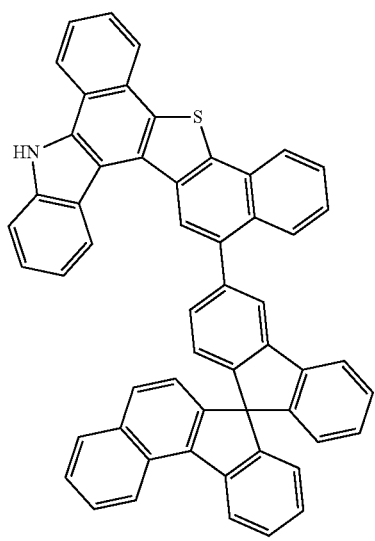
Sub 1-40
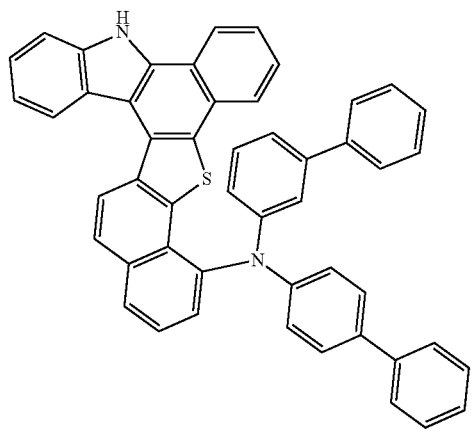
Sub 1-38
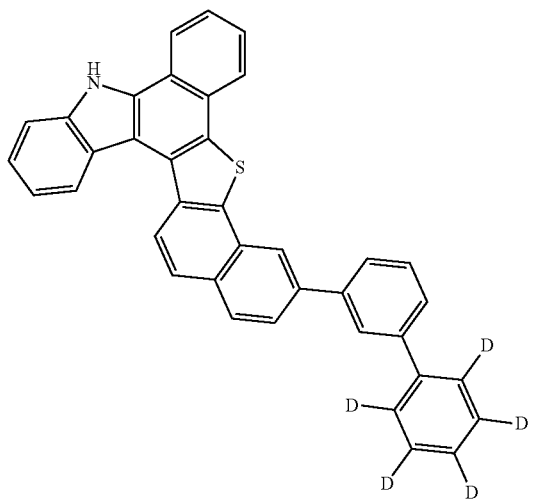
Sub 1-41
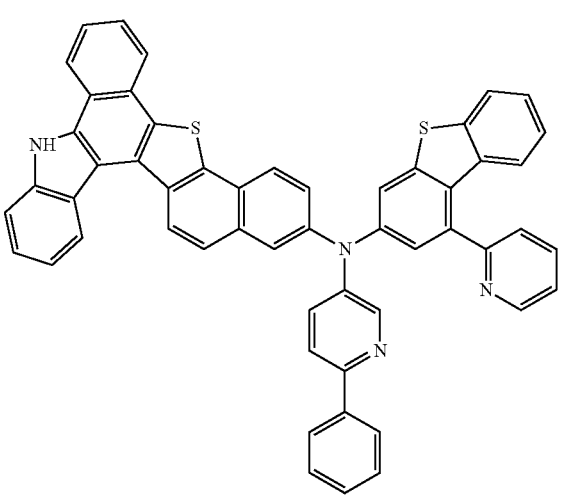

-continued
Sub 1-42
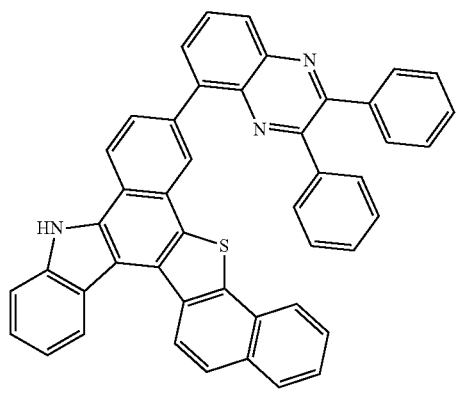
Sub 1-43
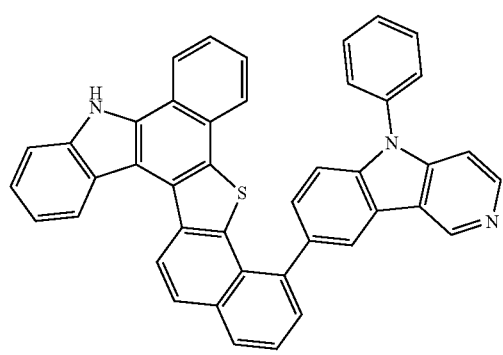
Sub 1-44
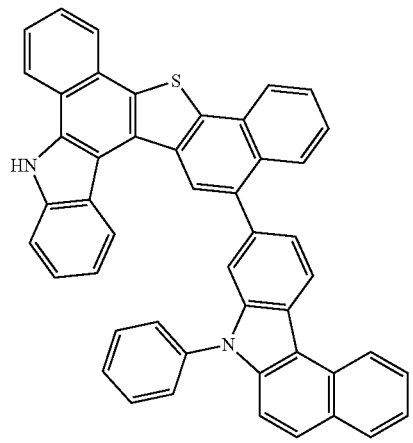
Sub 1-45
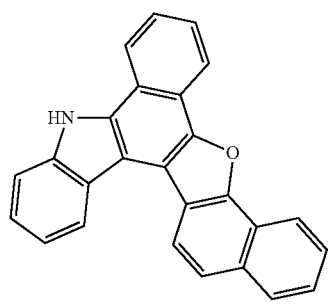
-continued
Sub 1-46
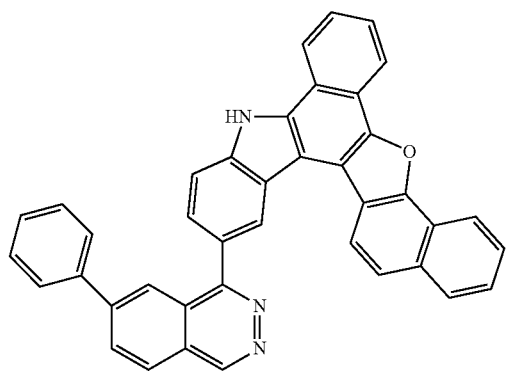
Sub 1-47
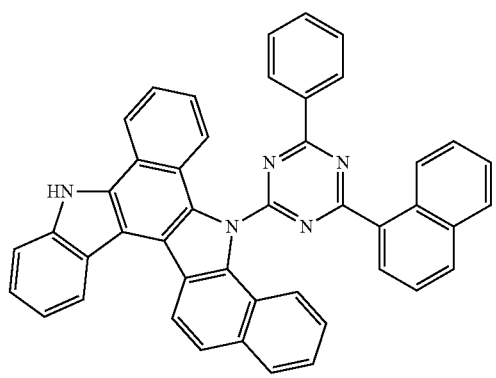
Sub 1-48
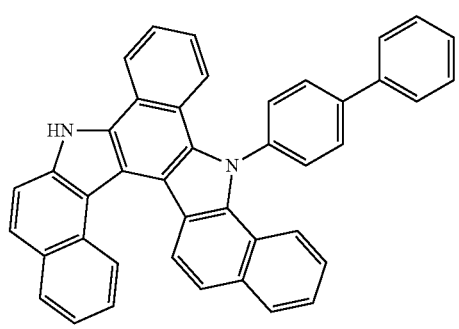
Sub 1-49
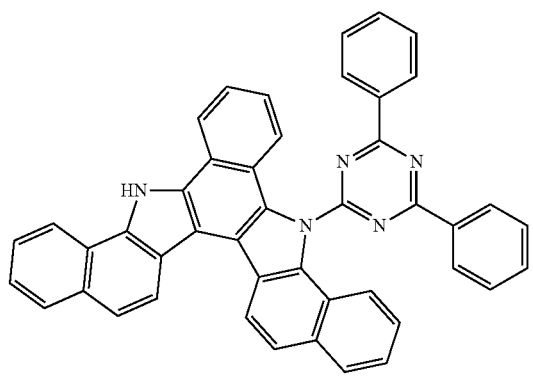

Sub 1-50
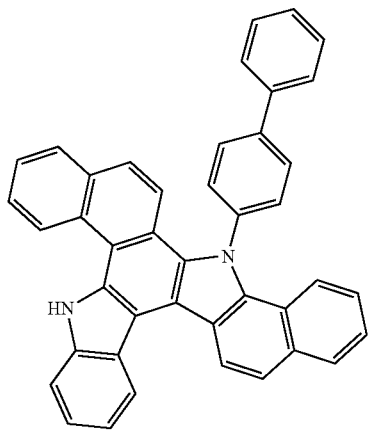
Sub 1-51
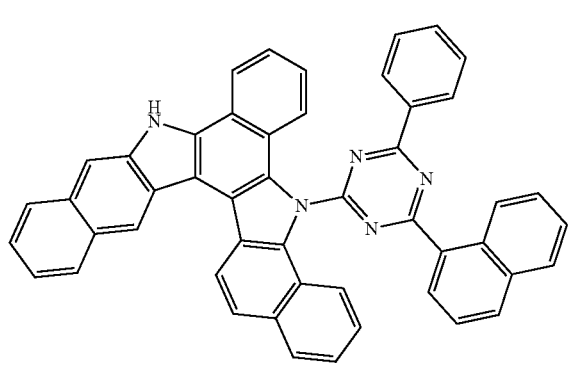
Sub 1-52
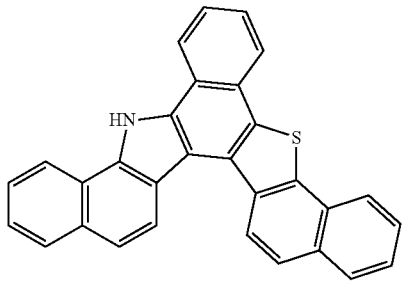
Sub 1-53
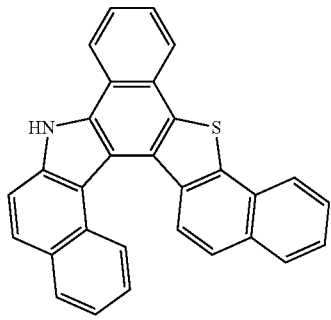
Sub 1-54
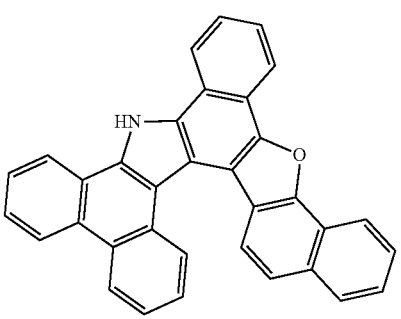
Sub 55
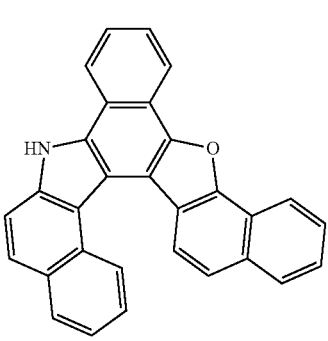
Sub 1-56
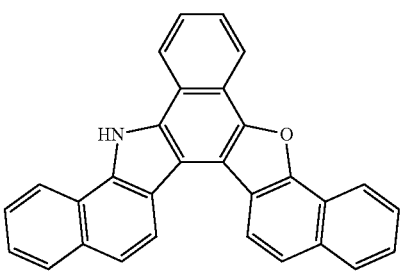
TABLE 1
| compound | FD-MS | compound | FD-MS |
|---|---|---|---|
| Sub 1-1 | m/z = 432.16 ($C_{32}H_{20}N_2$ = 432.53) | Sub 1-2 | m/z = 508.19 ($C_{38}H_{24}N_2$ = 508.62) |
| Sub 1-3 | m/z = 548.23 ($C_{41}H_{28}N_2$ = 548.69) | Sub 1-4 | m/z = 538.15 ($C_{38}H_{22}N_2S$ = 538.67) |
| Sub 1-5 | m/z = 672.26 ($C_{51}H_{32}N_2$ = 672.83) | Sub 1-7 | m/z = 560.20 ($C_{40}H_{24}N_4$ = 560.66) |
| Sub 1-8 | m/z = 664.20 ($C_{48}H_{28}N_2S$ = 664.83) | Sub 1-9 | m/z = 610.22 ($C_{44}H_{26}N_4$ = 610.72) |
| Sub 1-10 | m/z = 662.25 ($C_{48}H_{30}N_4$ = 662.80) | Sub 1-11 | m/z = 582.21 ($C_{44}H_{26}N_2$ = 582.71) |

TABLE 1-continued

| compound | FD-MS | compound | FD-MS |
|---|---|---|---|
| Sub 1-12 | m/z = 587.21 ($C_{41}H_{25}N_5$ = 587.69) | Sub 1-13 | m/z = 587.21 ($C_{41}H_{25}N_5$ = 587.69) |
| Sub 1-14 | m/z = 634.23 ($C_{45}H_{28}N_4$ = 624.75) | Sub 1-15 | m/z = 549.21 ($C_{39}H_{25}N_4$ = 549.66) |
| Sub 1-16 | m/z = 462.17 ($C_{33}H_{22}N_2O$ = 462.55) | Sub 1-17 | m/z = 472.19 ($C_{35}H_{24}N_2$ = 472.59) |
| Sub 1-18 | m/z = 600.20 ($C_{42}H_{24}N_4O$ = 600.68) | Sub 1-20 | m/z = 751.27 ($C_{54}H_{33}N_5$ = 751.89) |
| Sub 1-21 | m/z = 508.19 ($C_{38}H_{24}N_2$ = 508.62) | Sub 1-22 | m/z = 746.27 ($C_{57}H_{34}N_2$ = 746.91) |
| Sub 1-23 | m/z = 673.25 ($C_{50}H_{31}N_3$ = 673.82) | Sub 1-24 | m/z = 647.24 ($C_{48}H_{29}N_3$ = 647.78) |
| Sub 1-25 | m/z = 635.24 ($C_{47}H_{29}N_3$ = 635.77) | Sub 1-29 | m/z = 649.25 ($C_{48}H_{31}N_3$ = 649.80) |
| Sub 1-30 | m/z = 468.14 ($C_{32}H_{18}F_2N_2$ = 468.51) | Sub 1-31 | m/z = 736.26 ($C_{54}H_{32}N_4$ = 736.88) |
| Sub 1-32 | m/z = 663.24 ($C_{47}H_{29}N_5$ = 663.78) | Sub 1-33 | m/z = 373.09 ($C_{26}H_{15}NS$ = 373.47) |
| Sub 1-34 | m/z = 601.19 ($C_{44}H_{27}NS$ = 601.77) | Sub 1-35 | m/z = 590.18 ($C_{42}H_{26}N_2S$ = 590.74) |
| Sub 1-36 | m/z = 580.17 ($C_{39}H_{24}N_4S$ = 580.71) | Sub 1-37 | m/z = 737.22 ($C_{55}H_{31}NS$ = 737.92) |
| Sub 1-38 | m/z = 530.19 ($C_{38}H_{18}D_5NS$ = 530.70) | Sub 1-40 | m/z = 692.23 ($C_{50}H_{32}N_2S$ = 692.88) |
| Sub 1-42 | m/z = 653.19 ($C_{46}H_{27}N_3S$ = 653.80) | Sub 1-43 | m/z = 615.18 ($C_{43}H_{25}N_3S$ = 615.75) |
| Sub 1-44 | m/z = 664.20 ($C_{48}H_{28}N_2S$ = 664.83) | Sub 1-45 | m/z = 357.12 ($C_{26}H_{15}NO$ = 357.41) |
| Sub 1-46 | m/z = 561.18 ($C_{40}H_{23}N_3O$ = 561.64) | Sub 1-47 | m/z = 637.23 ($C_{45}H_{27}N_5$ = 637.75) |
| Sub 1-48 | m/z = 558.21 ($C_{42}H_{26}N_2$ = 558.68) | Sub 1-51 | m/z = 687.24 ($C_{49}H_{29}N_5$ = 687.81) |
| Sub 1-52 | m/z = 423.11 ($C_{30}H_{17}NS$ = 423.53) | Sub 1-54 | m/z = 457.15 ($C_{34}H_{19}NO$ = 457.53) |
| Sub 1-55 | m/z = 407.13 ($C_{30}H_{17}NO$ = 407.47) | | |

2. Synthesis of Sub 2

Sub 2 of Reaction Scheme 3 can be synthesized by the reaction path of the following Reaction Scheme 3, but is not limited thereto.

($Hal^1$=I, Br, Cl; $Hal^2$=Br, Cl)

<Reaction Scheme 3>

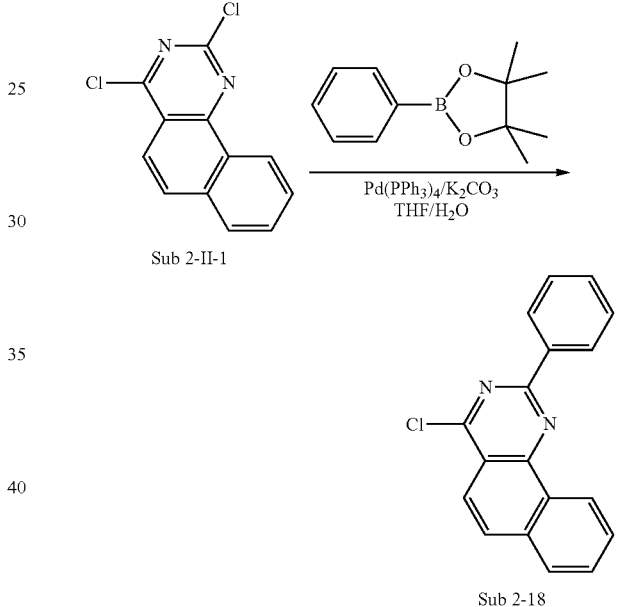

Synthesis of Sub 2-18

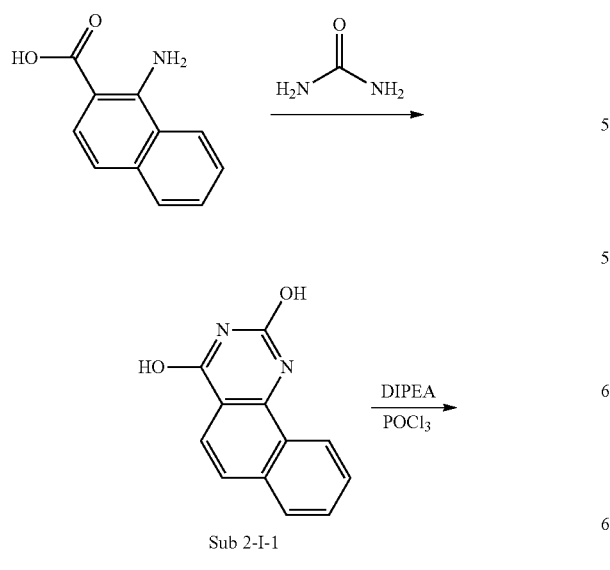

(1) Synthesis of Sub 2-I-1

The starting material, 1-amino-2-naphthoic acid (CAS Registry Number: 4919-43-1) (75.11 g, 401.25 mmol), was placed in a round bottom flask with urea (CAS Registry Number: 57-13-6) (168.69 g, 2808.75 mmol) and stirred at 160° C. After confirming the reaction by TLC, the reaction mixture was cooled to 100° C., water (200 ml) was added, and the mixture was stirred for 1 hour. When the reaction was completed, the resulting solid was filtered under reduced pressure, washed with water, and then dried to obtain 63.86 g (yield: 75%) of the product.

(2) Synthesis of Sub 2-II-1

Sub 2-I-1 (63.86 g, 300.94 mmol) was dissolved in $POCl_3$ (200 ml) at room temperature in a round bottom flask, and N, N-Diisopropylethylamine (97.23 g, 752.36 mmol) was slowly added dropwise thereto, followed by stirring at 90° C. After the reaction was completed, the reaction mixture was concentrated, and then ice water (500 ml) was added thereto, followed by stirring at room temperature for 1 hour. The resulting solid was filtered under reduced pressure and dried to obtain 67.47 g (yield: 90%) of the product.

(3) Synthesis of Sub 2-18

After Sub 2-II-1 (67.47 g, 270.86 mmol) was dissolved in THF (950 ml) in a round bottom flask, 4,4,5,5-tetramethyl-2-phenyl-1,3,2-dioxaborolane (CAS Registry Number: 24388-23-6) (60.80 g, 297.94 mmol), Pd(PPh₃)₄ (12.52 g, 10.83 mmol), K₂CO₃ (112.30 g, 812.57 mmol) and water (475 mL) were added to dissolve and stirred at 90° C. After the reaction was completed, the reaction mixture was extracted with CH₂Cl₂ and water. The organic layer was dried over MgSO₄ and concentrated. The resulting compound was purified by silicagel column and recrystallized to obtain 44.89 g (yield: 57%) of the product.

Synthesis of Sub 2-35

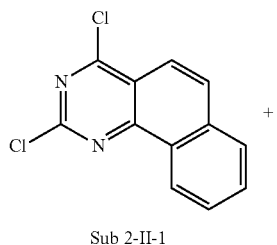

Sub 2-II-1

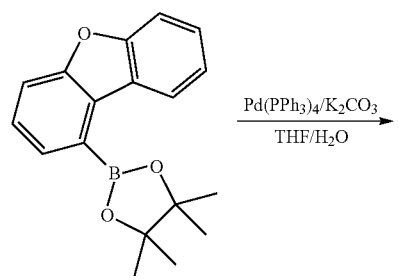

Sub 2-35

Sub 2-II-1 (19 g, 76.28 mmol), 2-(dibenzo[b,d]furan-1-yl)-4,4,5,5-tetramethyl-1,3,2-dioxaborolane (CAS Registry Number: 1822310-41-7) (26.92 g, 91.53 mmol), Pd(PPh₃)₄ (3.53 g, 3.05 mmol), K₂CO₃ (31.63 g, 228.83 mmol), THF (280 ml) and water (140 ml) were added and carried out in the same manner as in Sub 2-18 to give the product. (15.69 g, 54%).

Synthesis of Sub 4-49

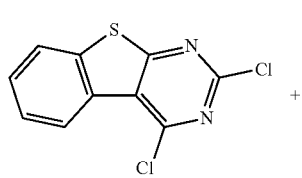

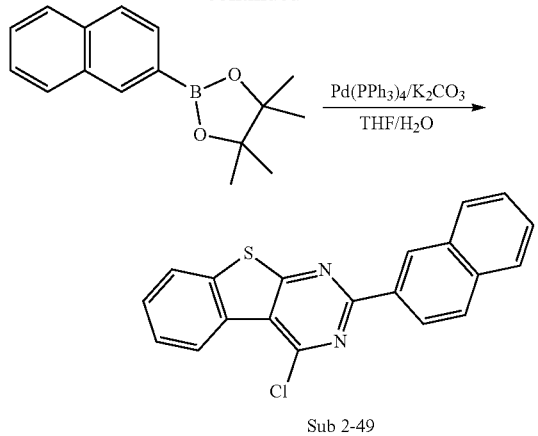

Sub 2-49

[1]Benzothieno[2,3-d]pyrimidine, 2,4-dichloro- (CAS Registry Number: 76872-40-7) (32.01 g, 125.47 mmol), 1,3,2-Dioxaborolane, 4,4,5,5-tetramethyl-2-(2-naphthalenyl) (CAS Registry Number: 256652-04-7) (38.26 g, 150.56 mmol), Pd(PPh₃)₄ (5.80 g, 5.02 mmol), K₂CO₃ (52.02 g, 376.41 mmol), THF (460 ml) and water (230 ml) were added and carried out in the same manner as in Sub 2-18 to give the product. (19.58 g, 45%).

The compounds belonging to Sub 2 may be, but not limited to, the following compounds, and Table 2 shows FD-MS (Field Desorption-Mass Spectrometry) values of Sub 2 compounds.

Examples of Sub 2 include, but are not limited to, the followings.

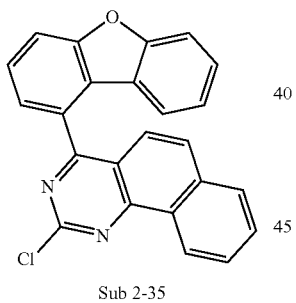

-continued
Sub 2-6
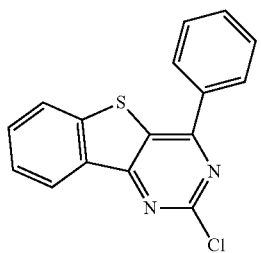
Sub 2-7
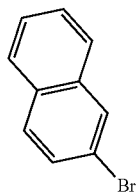
Sub 2-8
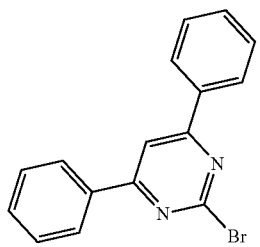
Sub 2-9
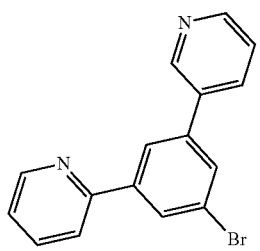
Sub 2-10
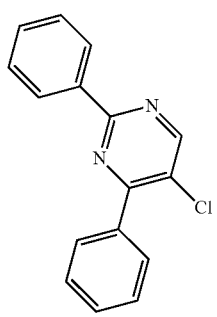
Sub 2-11
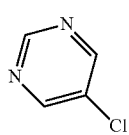
Sub 2-12
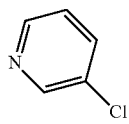
-continued
Sub 2-13
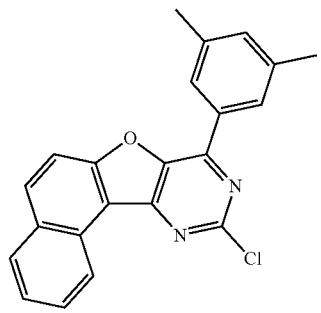
Sub 2-14
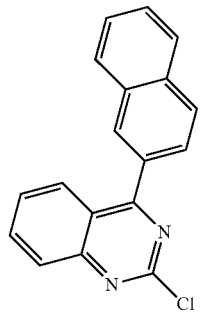
Sub 2-15
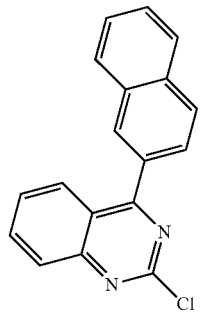
Sub 2-16
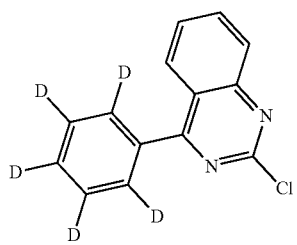
Sub 2-17
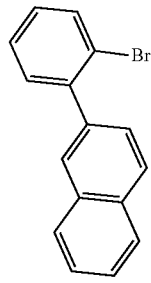

-continued
Sub 2-18
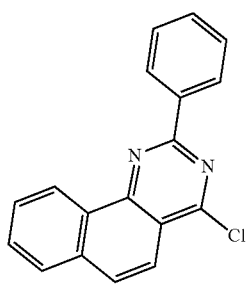
Sub 2-19
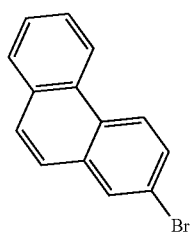
Sub 2-20
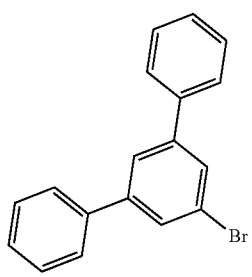
Sub 2-21
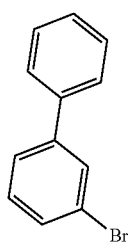
Sub 2-22
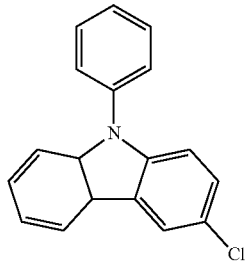
Sub 2-23
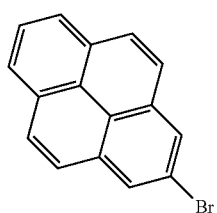
-continued
Sub 2-24
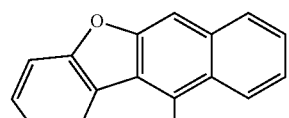
Sub 2-25
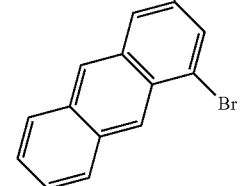
Sub 2-26
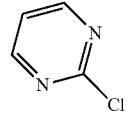
Sub 2-27
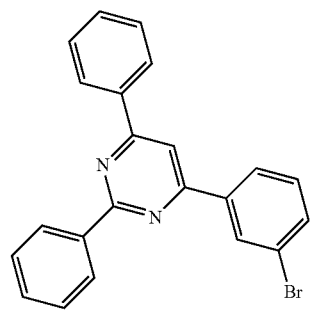
Sub 2-28
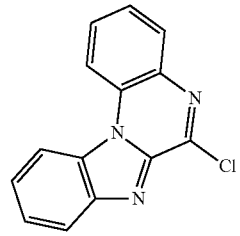
Sub 2-29
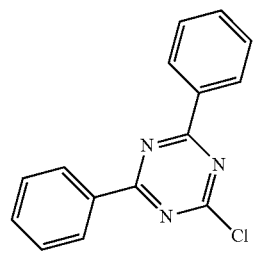

Sub 2-30
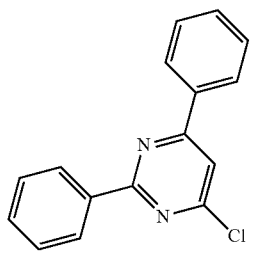
Sub 2-31
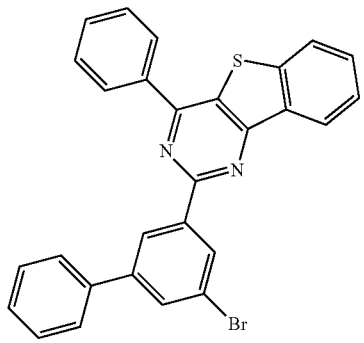
Sub 2-32
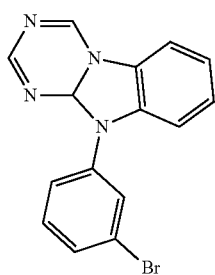
Sub 2-33
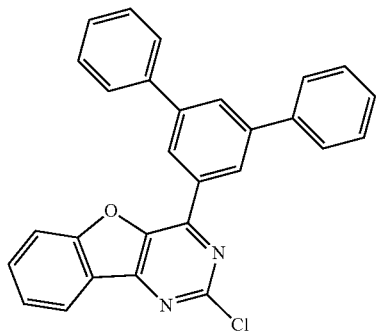
Sub 2-34
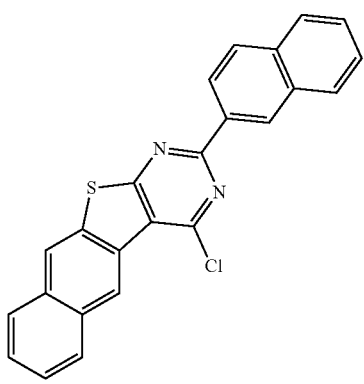
Sub 2-35
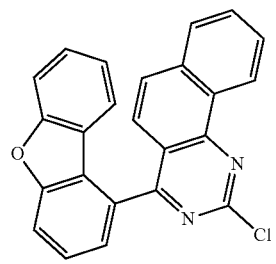
Sub 2-36
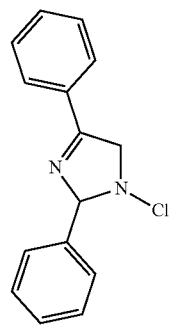
Sub 2-37
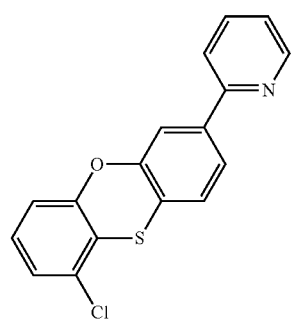
Sub 2-38
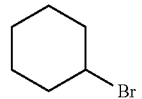
Sub 2-39
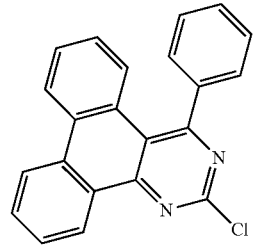
Sub 2-40
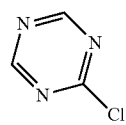

Sub 2-41 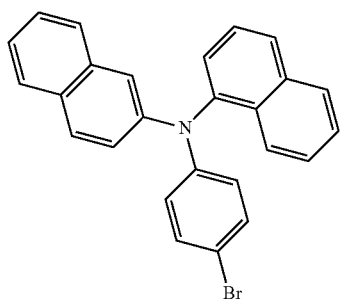
Sub 2-42 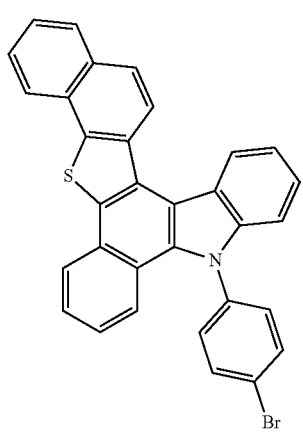
Sub 2-43 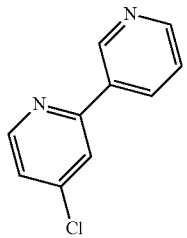
Sub 2-44 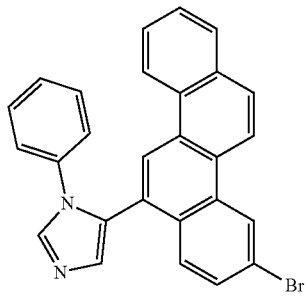
Sub 2-45 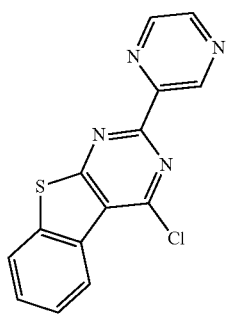
Sub 2-46 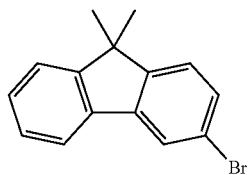
Sub 2-47 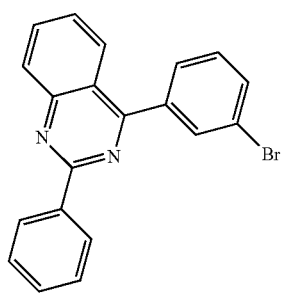
Sub 2-48 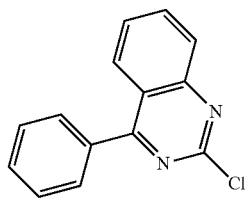
Sub 2-49 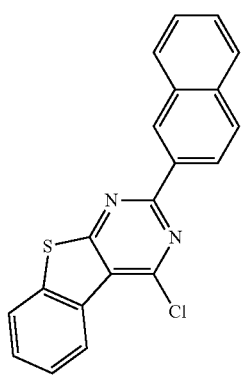
Sub 2-50 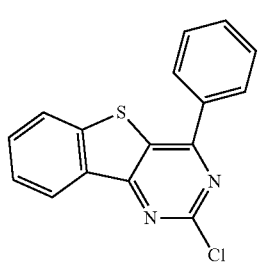

Sub 2-51 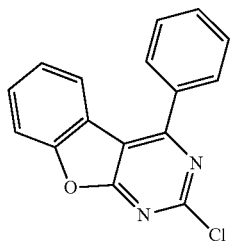

Sub 2-52 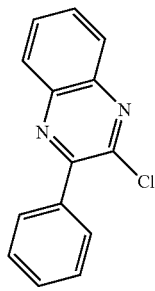

Sub 2-53 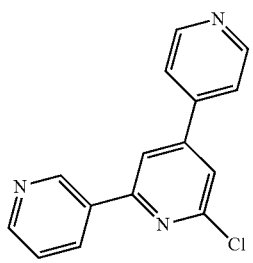

Sub 2-54 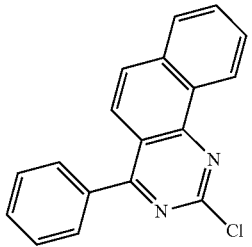

Sub 2-55 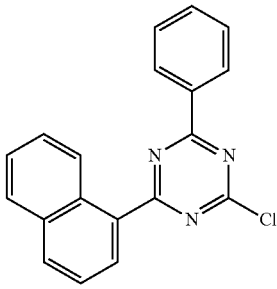

Sub 2-56 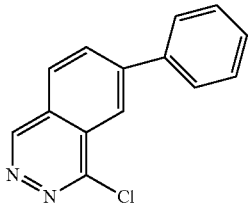

TABLE 2

| compound | FD-MS | compound | FD-MS |
|---|---|---|---|
| Sub 2-1 | m/z = 155.96 ($C_6H_5Br$ = 157.01) | Sub 2-2 | m/z = 205.97 ($C_{10}H_7Br$ = 207.07) |
| Sub 2-3 | m/z = 245.97 ($C_{12}H_7BrO$ = 247.09) | Sub 2-4 | m/z = 113.00 ($C_5H_4ClN$ = 113.54) |
| Sub 2-5 | m/z = 372.01 ($C_{22}H_{13}BrO$ = 373.25) | Sub 2-6 | m/z = 296.02 ($C_{16}H_9ClN_2S$ = 296.77) |
| Sub 2-8 | m/z = 266.06 ($C_{16}H_{11}ClN_2$ = 266.73) | Sub 2-9 | m/z = 310.01 ($C_{16}H_{11}BrN_2$ = 311.18) |
| Sub 2-11 | m/z = 114.00 ($C_4H_3ClN_2$ = 114.53) | Sub 2-12 | m/z = 113.00 ($C_5H_4ClN$ = 113.54) |
| Sub 2-13 | m/z = 358.09 ($C_{22}H_{15}ClN_2O$ = 358.83) | Sub 2-14 | m/z = 290.06 ($C_{18}H_{11}ClN_2$ = 290.75) |
| Sub 2-15 | m/z = 245.08 ($C_{14}H_4D_5ClN_2$ = 245.72) | Sub 2-16 | m/z = 392.11 ($C_{26}H_{17}ClN_2$ = 392.89) |
| Sub 2-17 | m/z = 282.00 ($C_6H_{11}Br$ = 283.17) | Sub 2-18 | m/z = 290.06 ($C_{18}H_{11}ClN_2$ = 290.75) |
| Sub 2-19 | m/z = 255.99 ($C_{14}H_9Br$ = 257.13) | Sub 2-20 | m/z = 308.02 ($C_{18}H_{13}Br$ = 309.21) |
| Sub 2-21 | m/z = 231.99 ($C_{12}H_9Br$ = 233.11) | Sub 2-22 | m/z = 279.08 ($C_{18}H_{14}ClN$ = 279.77) |
| Sub 2-23 | m/z = 279.99 ($C_{16}H_9Br$ = 281.15) | Sub 2-26 | m/z = 386.04 ($C_{22}H_{15}BrN_2$ = 387.28) |
| Sub 2-27 | m/z = 253.04 ($C_{14}H_8ClN_3$ = 253.69) | Sub 2-28 | m/z = 267.06 ($C_{15}H_{10}ClN_3$ = 267.72) |
| Sub 2-31 | m/z = 492.03 ($C_{28}H_{17}BrN_2S$ = 493.42) | Sub 2-32 | m/z = 326.02 ($C_{15}H_{11}BrN_4$ = 327.17) |
| Sub 2-33 | m/z = 432.10 ($C_{28}H_{17}ClN_2O$ = 432.91) | Sub 2-34 | m/z = 396.05 ($C_{24}H_{13}ClN_2S$ = 396.89) |
| Sub 2-35 | m/z = 380.07 ($C_{24}H_{13}ClN_2O$ = 380.83) | Sub 2-36 | m/z = 256.08 ($C_{15}H_{13}ClN_2$ = 256.73) |
| Sub 2-37 | m/z = 311.02 ($C_{17}H_{10}ClNOS$ = 311.78) | Sub 2-38 | m/z = 162.00 ($C_6H_{11}Br$ = 163.06) |
| Sub 2-55 | m/z = 317.07 ($C_{19}H_{12}ClN_3$ = 317.78) | | |

Synthesis Example of Final Products

Sub 1(1 eq.) was dissolved in toluene in a round bottom flask, and Sub 2(1 eq.), $Pd_2(dba)_3$ (0.03 eq.), $P(t-Bu)_3$ (0.1 eq.), NaOt-Bu (3 eq.) were added and stirred at 100° C. When the reaction was complete, the reaction mixture was extracted with $CH_2Cl_2$ and water. The organic layer was dried over $MgSO_4$ and concentrated. The resulting compound was separated by silicagel column chromatography and recrystallization to obtain the Final products.

Synthesis of 1-1

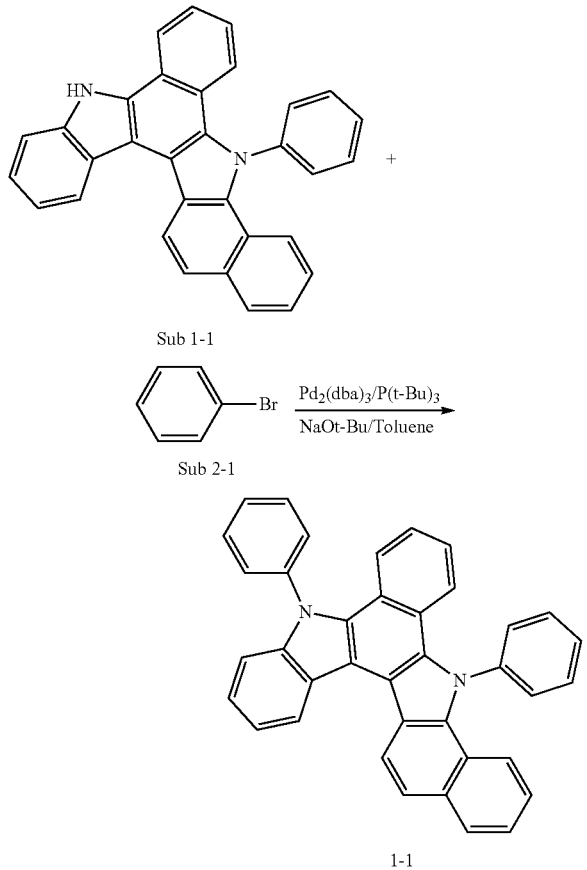

Sub 1-1(5.85 g, 13.53 mmol) was dissolved in toluene (135 ml) in a round bottom flask, and Sub 2-1 (2.12 g, 13.53 mmol), Pd$_2$(dba)$_3$ (0.37 g, 0.41 mmol), P(t-Bu)$_3$ (0.16 g, 0.81 mmol), NaOt-Bu (3.90 g, 40.58 mmol) were added and stirred at 100° C. When the reaction was complete, the reaction mixture was extracted with CH$_2$Cl$_2$ and water. The organic layer was dried over MgSO$_4$ and concentrated. The resulting compound was separated by silicagel column chromatography and recrystallization to obtain 5.43 g of product. (yield: 79%)

Synthesis of 1-12

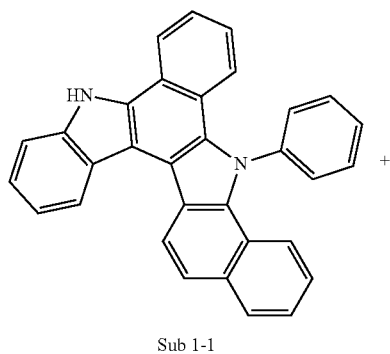

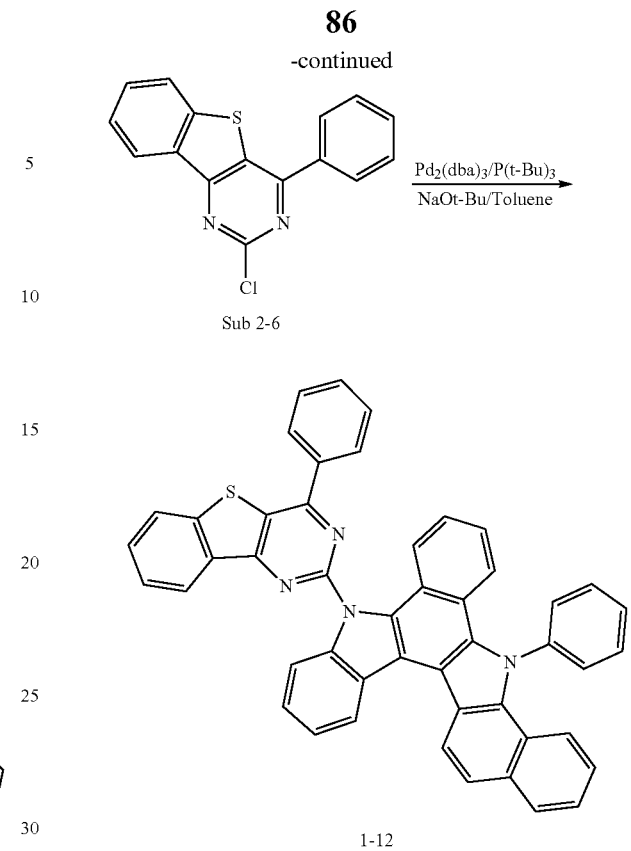

Sub 1-1 (5.85 g, 13.53 mmol), toluene (135 ml), Sub 4-42 (4.01 g, 13.53 mmol), Pd$_2$(dba)$_3$ (0.37 g, 0.41 mmol), P(t-Bu)$_3$ (0.16 g, 0.81 mmol), NaOt-Bu (3.90 g, 40.58 mmol) were carried out in the same manner as 1-1 to obtain 6.65 g of the product (yield: 71%)

Synthesis of 1-26

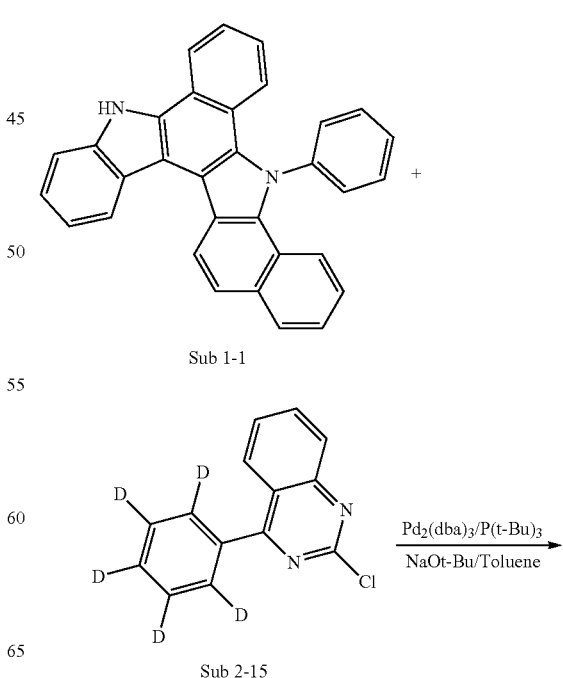

Synthesis of 1-33

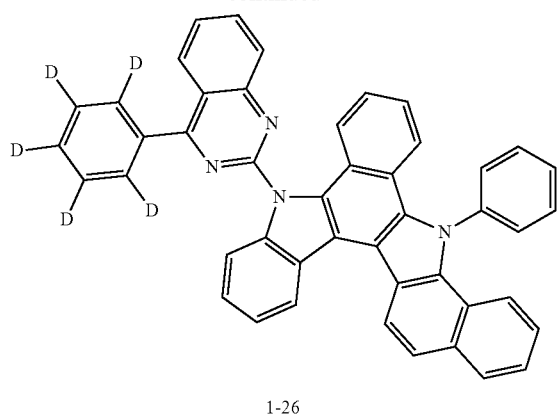

1-26

Sub 1-1 (5.85 g, 13.53 mmol), toluene (135 ml), Sub 2-15 (3.32 g, 13.53 mmol), Pd$_2$(dba)$_3$ (0.37 g, 0.41 mmol), P(t-Bu)$_3$ (0.16 g, 0.81 mmol), NaOt-Bu (3.90 g, 40.58 mmol) were carried out in the same manner as 1-1 to obtain 5.90 g of the product (yield: 68%)

Synthesis of 1-27

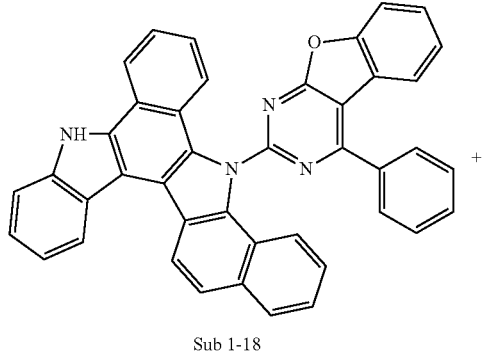

Sub 1-18

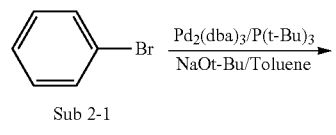

Sub 2-1

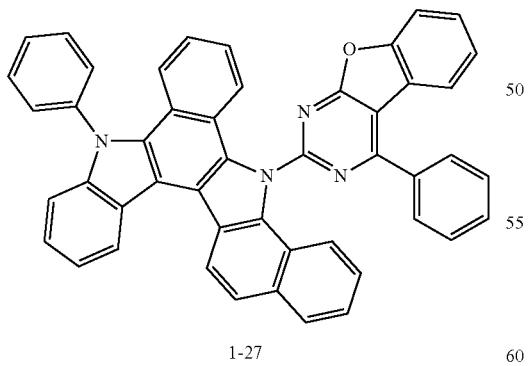

1-27

Sub 1-18 (7.85 g, 13.07 mmol), toluene (131 ml), Sub 2-1 (2.05 g, 13.07 mmol), Pd$_2$(dba)$_3$ (0.36 g, 0.39 mmol), P(t-Bu)$_3$ (0.16 g, 0.78 mmol), NaOt-Bu (3.77 g, 39.21 mmol) were carried out in the same manner as 1-1 to obtain 6.46 g of the product (yield: 73%)

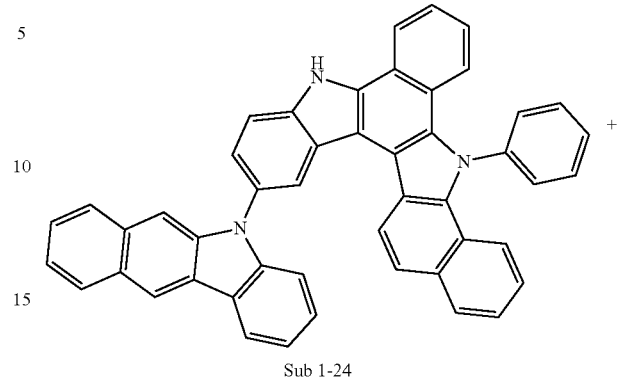

Sub 1-24

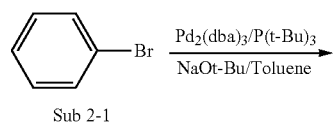

Sub 2-1

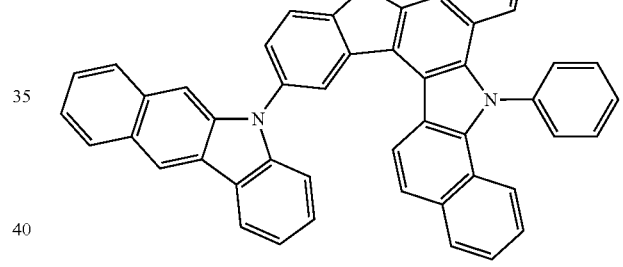

1-33

Sub 1-24 (10.00 g, 15.44 mmol), toluene (154 ml), Sub 2-1 (2.42 g, 15.44 mmol), Pd$_2$(dba)$_3$ (0.42 g, 0.46 mmol), P(t-Bu)$_3$ (0.19 g, 0.93 mmol), NaOt-Bu (4.45 g, 46.31 mmol) were carried out in the same manner as 1-1 to obtain 7.84 g of the product (yield: 75%)

Synthesis of 1-47

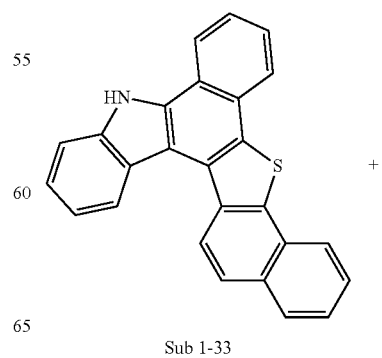

Sub 1-33

-continued
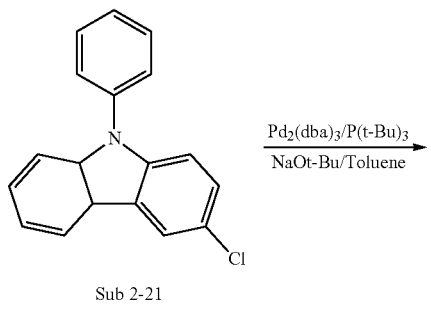
Sub 2-21
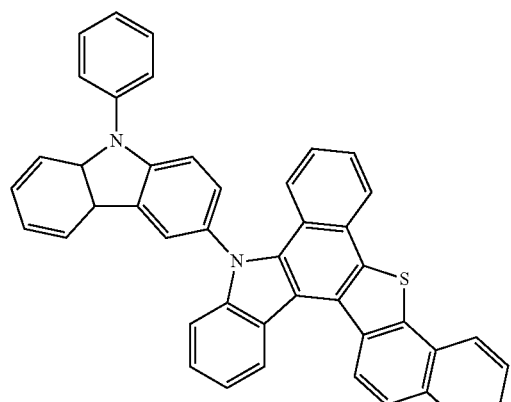
1-47
Sub 1-33 (6.55 g, 17.54 mmol), toluene (175 ml), Sub 2-21 (4.91 g, 17.54 mmol), Pd$_2$(dba)$_3$ (0.48 g, 0.53 mmol), P(t-Bu)$_3$ (0.21 g, 1.05 mmol), NaOt-Bu (5.06 g, 52.61 mmol) were carried out in the same manner as 1-1 to obtain 8.44 g of the product (yield: 78%)
Synthesis of 1-54
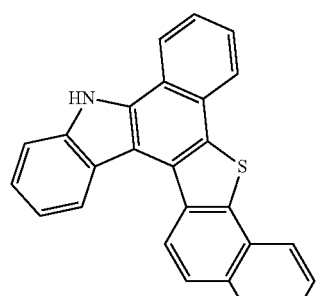
Sub 1-33
-continued
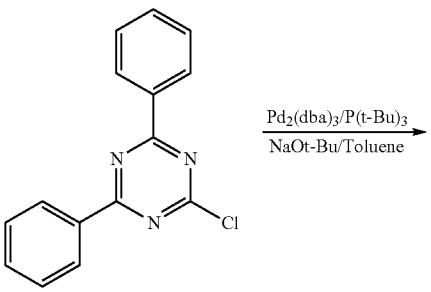
Sub 2-27
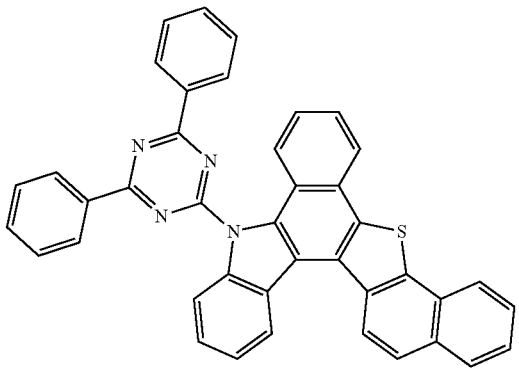
1-54
Sub 1-33 (6.55 g, 17.54 mmol), toluene (175 ml), Sub 2-21 (4.70 g, 17.54 mmol), Pd$_2$(dba)$_3$ (0.48 g, 0.53 mmol), P(t-Bu)$_3$ (0.21 g, 1.05 mmol), NaOt-Bu (5.06 g, 52.61 mmol) were carried out in the same manner as 1-1 to obtain 8.38 g of the product (yield: 79%)
Synthesis of 1-74
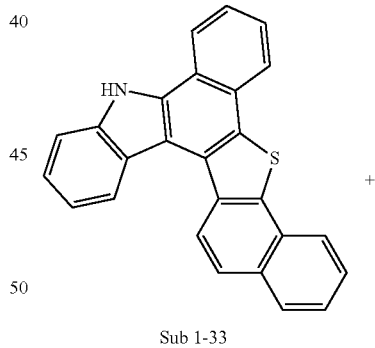
Sub 1-33
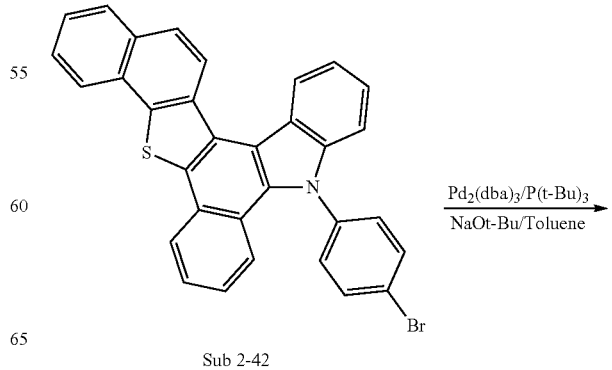
Sub 2-42

-continued

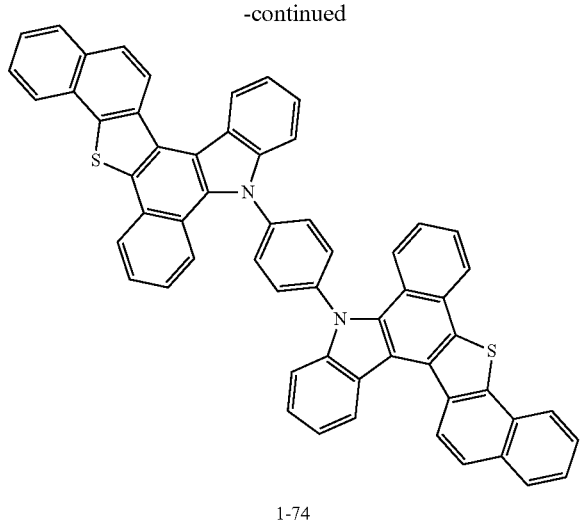

1-74

Sub 1-33 (8.57 g, 22.95 mmol), toluene (229 ml), Sub 2-42 (12.13 g, 22.95 mmol), Pd₂(dba)₃ (0.63 g, 0.69 mmol), P(t-Bu)₃ (0.28 g, 1.38 mmol), NaOt-Bu (6.62 g, 68.84 mmol) were carried out in the same manner as 1-1 to obtain 12.81 g of the product (yield: 68%)

Synthesis of 1-81

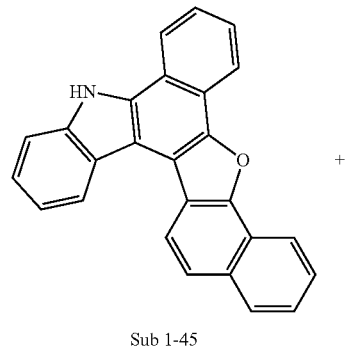

Sub 1-45

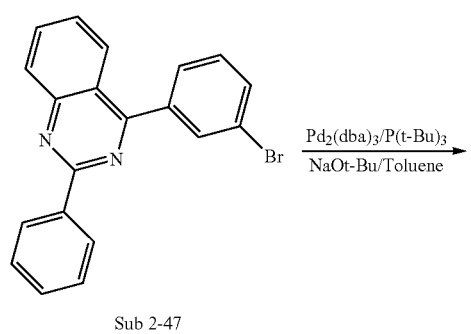

Sub 2-47

-continued

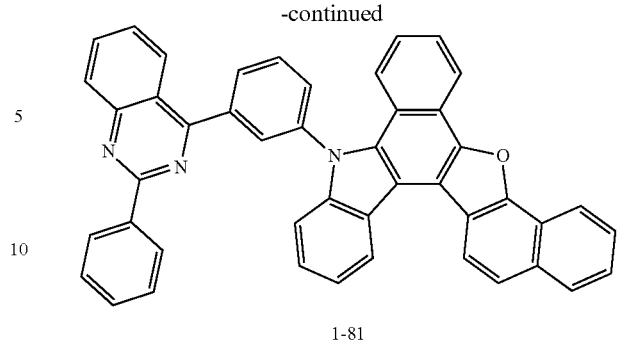

1-81

Sub 1-45 (7.21 g, 20.17 mmol), toluene (202 ml), Sub 2-47 (7.29 g, 20.17 mmol), Pd₂(dba)₃ (0.55) were carried out in the same manner as 1-1 to obtain 10.16 g of the product (yield: 79%)

Synthesis of 1-90

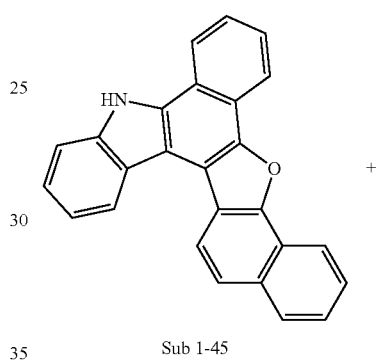

Sub 1-45

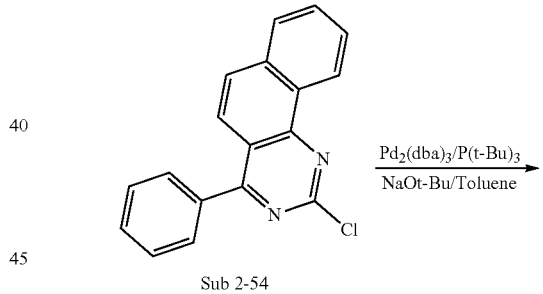

Sub 2-54

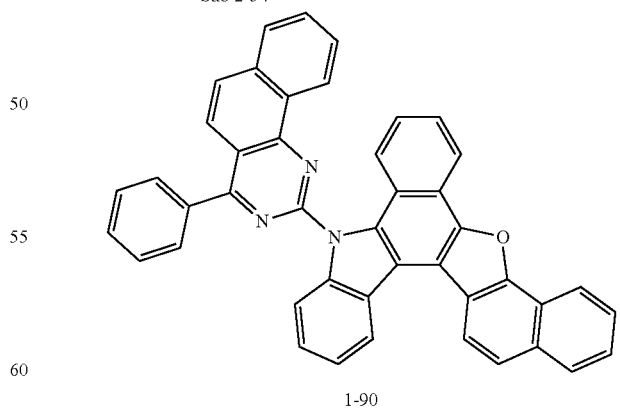

1-90

Sub 1-45 (10.13 g, 28.34 mmol), toluene (283 ml), Sub 2-54 (8.24 g, 28.34 mmol), Pd₂(dba)₃ (0.78 g, 0.85 mmol), P(t-Bu)₃ (0.34 g, 1.70 mmol), NaOt-Bu (8.17 g, 85.03 mmol) were carried out in the same manner as 1-1 to obtain 13.35 g of the product (yield: 77%)

TABLE 3

| compound | FD-MS | compound | FD-MS |
|---|---|---|---|
| 1-1 | m/z = 508.19($C_{38}H_{24}N_2$ = 508.62) | 1-2 | m/z = 634.24($C_{48}H_{30}N_2$ = 634.78) |
| 1-3 | m/z = 624.26($C_{47}H_{32}N_2$ = 624.79) | 1-4 | m/z = 614.18($C_{44}H_{26}N_2S$ = 614.77) |
| 1-5 | m/z = 598.20($C_{44}H_{26}N_2O$ = 598.71) | 1-6 | m/z = 748.29($C_{57}H_{36}N_2$ = 748.93) |
| 1-7 | m/z = 824.32($C_{63}H_{40}N_2$ = 825.03) | 1-8 | m/z = 636.23($C_{46}H_{28}N_4$ = 636.76) |
| 1-9 | m/z = 509.19($C_{37}H_{23}N_3$ = 509.61) | 1-10 | m/z = 740.23($C_{54}H_{32}N_2S$ = 740.92) |
| 1-11 | m/z = 724.25($C_{54}H_{32}N_2O$ = 724.86) | 1-12 | m/z = 692.20($C_{48}H_{28}N_4S$ = 692.84) |
| 1-13 | m/z = 736.26($C_{54}H_{32}N_4$ = 736.88) | 1-14 | m/z = 662.25($C_{48}H_{30}N_4$ = 662.80) |
| 1-15 | m/z = 713.26($C_{51}H_{31}N_5$ = 713.84) | 1-16 | m/z = 814.31($C_{60}H_{38}N_4$ = 814.99) |
| 1-17 | m/z = 658.24($C_{50}H_{30}N_2$ = 658.80) | 1-18 | m/z = 663.24($C_{47}H_{29}N_5$ = 663.78) |
| 1-19 | m/z = 662.25($C_{48}H_{30}N_4$ = 662.80) | 1-20 | m/z = 662.25($C_{48}H_{30}N_4$ = 662.80) |
| 1-21 | m/z = 663.24($C_{47}H_{29}N_5$ = 663.78) | 1-22 | m/z = 702.25($C_{49}H_{30}N_6$ = 702.82) |
| 1-23 | m/z = 626.23($C_{44}H_{28}N_5$ = 626.74) | 1-24 | m/z = 784.28($C_{55}H_{36}N_4O_2$ = 784.92) |
| 1-25 | m/z = 726.28($C_{53}H_{34}N_4$ = 726.88) | 1-26 | m/z = 641.26($C_{46}H_{23}D_5N_4$ = 641.79) |
| 1-27 | m/z = 677.22($C_{47}H_{27}N_5O$ = 677.77) | 1-28 | m/z = 844.36($C_{62}H_{44}N_4$ = 845.06) |
| 1-29 | m/z = 953.35($C_{70}H_{43}N_5$ = 954.15) | 1-30 | m/z = 584.23($C_{44}H_{28}N_2$ = 584.72) |
| 1-31 | m/z = 822.30($C_{63}H_{38}N_2$ = 823.01) | 1-32 | m/z = 749.28($C_{56}H_{35}N_3$ = 749.92) |
| 1-33 | m/z = 723.27($C_{54}H_{33}N_3$ = 723.88) | 1-34 | m/z = 711.27($C_{53}H_{33}N_3$ = 711.87) |
| 1-35 | m/z = 800.32($C_{61}H_{40}N_2$ = 801.01) | 1-36 | m/z = 827.33($C_{62}H_{41}N_3$ = 828.03) |
| 1-37 | m/z = 710.27($C_{54}H_{34}N_2$ = 710.88) | 1-38 | m/z = 725.28($C_{54}H_{35}N_3$ = 725.90) |
| 1-39 | m/z = 544.18($C_{38}H_{22}F_2N_2$ = 544.60) | 1-40 | m/z = 812.29($C_{60}H_{36}N_4$ = 812.98) |
| 1-41 | m/z = 917.33($C_{65}H_{39}N_7$ = 918.08) | 1-42 | m/z = 449.12($C_{32}H_{19}NS$ = 449.57) |
| 1-43 | m/z = 499.14($C_{36}H_{21}NS$ = 499.63) | 1-44 | m/z = 549.16($C_{40}H_{23}NS$ = 549.69) |
| 1-45 | m/z = 601.19($C_{44}H_{27}NS$ = 601.77) | 1-46 | m/z = 525.16($C_{38}H_{23}NS$ = 525.67) |
| 1-47 | m/z = 616.20($C_{44}H_{28}N_2S$ = 616.78) | 1-48 | m/z = 573.16($C_{42}H_{23}NS$ = 573.71) |
| 1-49 | m/z = 765.21($C_{56}H_{31}NOS$ = 765.93) | 1-50 | m/z = 551.17($C_{40}H_{25}NS$ = 551.71) |
| 1-51 | m/z = 451.11($C_{30}H_{17}N_3S$ = 451.55) | 1-52 | m/z = 679.21($C_{48}H_{29}N_3S$ = 679.84) |
| 1-53 | m/z = 590.16($C_{40}H_{22}N_4S$ = 590.70) | 1-54 | m/z = 604.17($C_{41}H_{24}N_4S$ = 604.73) |
| 1-55 | m/z = 654.19($C_{45}H_{26}N_4S$ = 654.79) | 1-56 | m/z = 577.16(C40H23N3S = 577.71) |
| 1-57 | m/z = 603.18($C_{42}H_{25}N_3S$ = 603.74) | 1-58 | m/z = 785.20($C_{54}H_{31}N_3S_2$ = 785.98) |
| 1-59 | m/z = 619.18($C_{41}H_{25}N_5S$ = 619.75) | 1-60 | m/z = 769.22($C_{54}H_{31}N_3OS$ = 769.92) |
| 1-61 | m/z = 733.16($C_{50}H_{27}N_3S_2$ = 733.91) | 1-62 | m/z = 717.19($C_{50}H_{27}N_3OS$ = 717.85) |
| 1-63 | m/z = 593.19($C_{41}H_{27}N_3S$ = 593.75) | 1-64 | m/z = 648.13($C_{43}H_{24}N_2OS_2$ = 648.80) |
| 1-65 | m/z = 601.19($C_{44}H_{27}NS$ = 601.77) | 1-66 | m/z = 455.17($C_{32}H_{25}NS$ = 455.62) |
| 1-67 | m/z = 894.28($C_{64}H_{38}N_4S$ = 895.10) | 1-68 | m/z = 659.19($C_{42}H_{25}N_7S$ = 659.77) |
| 1-69 | m/z = 813.25($C_{61}H_{35}NS$ = 814.02) | 1-70 | m/z = 609.20($C_{41}H_{19}D_5N_4S$ = 609.76) |
| 1-71 | m/z = 780.26($C_{57}H_{36}N_2S$ = 780.99) | 1-72 | m/z = 1035.36($C_{76}H_{49}N_3S$ = 1036.31) |
| 1-73 | m/z = 876.24($C_{60}H_{36}N_4S_2$ = 877.10) | 1-74 | m/z = 820.20($C_{58}H_{32}N_2S_2$ = 821.03) |
| 1-75 | m/z = 729.22($C_{52}H_{31}N_3S$ = 729.90) | 1-76 | m/z = 769.23($C_{53}H_{31}N_5S$ = 769.93) |
| 1-77 | m/z = 741.22($C_{53}H_{31}N_3S$ = 741.91) | 1-78 | m/z = 926.23($C_{62}H_{34}N_6S_2$ = 927.12) |
| 1-79 | m/z = 433.15($C_{32}H_{19}NO$ = 433.51) | 1-80 | m/z = 549.21($C_{41}H_{27}NO$ = 549.67) |
| 1-81 | m/z = 637.22($C_{46}H_{27}N_3O$ = 637.74) | 1-82 | m/z = 588.20($C_{41}H_{24}N_4O$ = 588.67) |
| 1-83 | m/z = 638.21($C_{45}H_{26}N_4O$ = 638.73) | 1-84 | m/z = 561.18($C_{40}H_{23}N_3O$ = 561.64) |
| 1-85 | m/z = 667.17($C_{46}H_{25}N_3OS$ = 667.79) | 1-86 | m/z = 617.16($C_{42}H_{23}N_3OS$ = 617.73) |
| 1-87 | m/z = 601.18($C_{42}H_{23}N_3O_2$ = 601.67) | 1-88 | m/z = 561.18($C_{40}H_{23}N_3O$ = 561.64) |
| 1-89 | m/z = 588.20($C_{41}H_{24}N_4O$ = 588.67) | 1-90 | m/z = 611.20($C_{44}H_{25}N_3O$ = 611.70) |
| 1-91 | m/z = 637.22($C_{46}H_{27}N_3O$ = 637.74) | 1-92 | m/z = 684.26($C_{52}H_{32}N_2$ = 684.84) |
| 1-93 | m/z = 713.26($C_{51}H_{31}N_5$ = 713.84) | 1-94 | m/z = 684.26($C_{52}H_{32}N_2$ = 684.84) |
| 1-95 | m/z = 763.27($C_{55}H_{33}N_5$ = 763.90) | 1-96 | m/z = 651.20($C_{48}H_{29}NS$ = 651.83) |
| 1-97 | m/z = 704.20($C_{49}H_{28}N_4S$ = 704.85) | 1-98 | m/z = 654.19($C_{45}H_{26}N_4S$ = 654.79) |
| 1-99 | m/z = 633.21($C_{48}H_{27}NO$ = 633.75) | 1-100 | m/z = 638.21($C_{45}H_{26}N_4O$ = 638.73) |
| 1-101 | m/z = 688.23($C_{49}H_{28}N_4O$ = 688.79) | | |

Otherwise, the synthesis examples of the present invention represented by Formula 1 have been described, but these are all based on the Buchwald-Hartwig cross coupling reaction, Suzuki cross-coupling reaction, Intramolecular acid-induced cyclization reaction (J. mater. Chem. 1999, 9, 2095.), Pd(II)-catalyzed oxidative cyclization reaction (Org. Lett. 2011, 13, 5504), Grignard reaction, Cyclic Dehydration reaction and $PPh_3$-mediated reductive cyclization reaction (J. Org. Chem. 2005, 70, 5014.), and those skilled in the art will readily understand that the above reaction proceeds even when, besides the substituent specified in the specific synthesis example, other substituents (substituents such as $Ar^1$ to $Ar^6$, $L^1$ to $L^6$, $R^1$ to $R^5$, $X^1$, $X^2$, A and B) defined in Formula 1 are bonded.

Evaluation of Manufacture of Organic Electric Element

Example 1) Manufacture and Evaluation of Red Organic Light Emitting Diode (Phosphorescent Host)

On an ITO layer(anode) formed on a glass substrate, 2-TNATA was vacuum-deposited to form a hole injection layer with a thickness of 60 nm, and NPB was vacuum-deposited on the hole injection layer to form a hole transport layer with a thickness of 60 nm.

Then, the emitting layer was deposited on the hole transport layer at a thickness of 30 nm by doping the inventive compound P 1-1 with the host material and [bis-(1-phenylisoquinolyl)iridium(III)acetylacetonate] (hereinafter abbreviated as(piq)$_2$Ir(acac)) with the dopant material at a weight ratio of 95:5. Next, BAlq was vacuum-deposited on the emitting layer to a thickness of 10 nm to form a hole blocking layer, and Alq3 was formed to a thickness of 40 nm on the hole blocking layer to form an electron transport layer. Thereafter, LiF was deposited to a thickness of 0.2 nm on the electron transport layer to form an electron injection layer, and then Al was deposited to a thickness of 150 nm on the electron injection layer to form a cathode.

[Example 2] to [Example 37] Red Organic Light Emitting Diode

An organic electroluminescent device was prepared in the same manner as in Example 1, except that the compound of the present invention described in Table 4 was used instead of the compound 1-1 as the host material of the emitting layer.

Comparative Examples 1 to 4

An organic electroluminescent device was prepared in the same manner as in Example 1, except that comparative compound 1 to 4 described in Table 4 was used instead of the compound 1-1 as the host material of the emitting layer.

To the OLEDs which were manufactured by example 1 to 30 and comparative examples 1 to 5, a forward bias direct current voltage was applied, and electroluminescent(EL) properties were measured using PR-650 of Photoresearch Co., and T95 life was measured using a life measuring apparatus manufactured by McScience Inc. with a reference luminance of 2500 cd/m². The measurement results are shown in Tables 4 below.

comparative compound 1

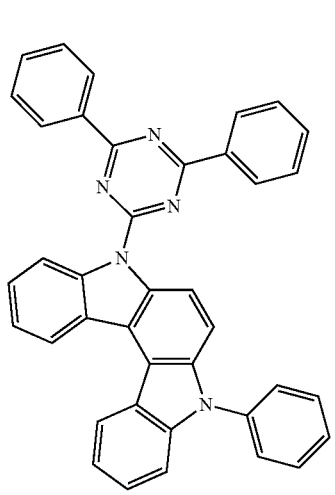

comparative compound 2

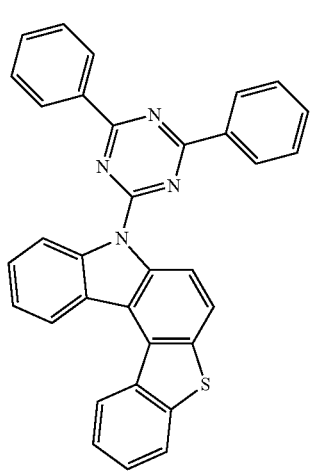

comparative compound 3

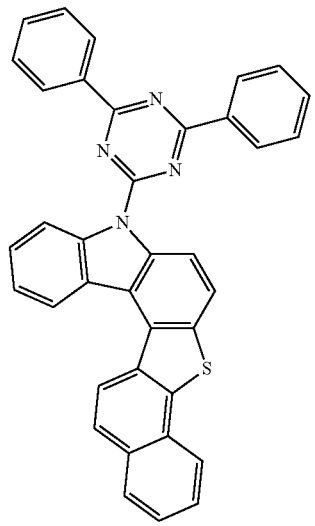

comparative compound 4

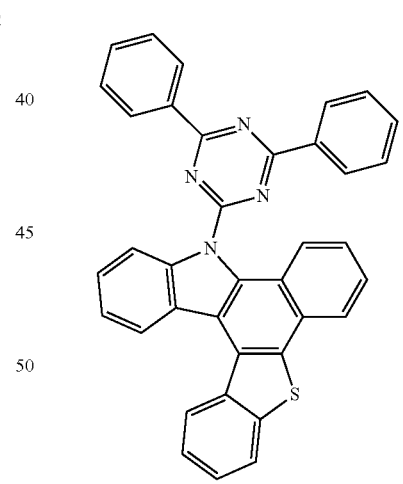

TABLE 4

| | compound | Voltage | Current Density | Brightness (cd/m²) | Efficiency (cd/A) | T(95) | CIE X | CIE Y |
|---|---|---|---|---|---|---|---|---|
| comparative example(1) | comparative compound 1 | 6.2 | 21.2 | 2500 | 11.8 | 108.5 | 0.66 | 0.32 |
| comparative example (2) | comparative compound 2 | 6.1 | 19.8 | 2500 | 12.6 | 110.8 | 0.66 | 0.32 |
| comparative example (3) | comparative compound 3 | 5.7 | 17.2 | 2500 | 14.5 | 113.5 | 0.66 | 0.32 |

TABLE 4-continued

| | compound | Voltage | Current Density | Brightness (cd/m$^2$) | Efficiency (cd/A) | T(95) | CIE X | CIE Y |
|---|---|---|---|---|---|---|---|---|
| comparative example (4) | comparative compound 4 | 5.7 | 16.3 | 2500 | 15.3 | 114.3 | 0.66 | 0.32 |
| example(1) | compound 1-1 | 5.3 | 11.4 | 2500 | 21.9 | 134.7 | 0.66 | 0.32 |
| example(2) | compound 1-2 | 5.3 | 11.7 | 2500 | 21.3 | 134.3 | 0.66 | 0.32 |
| example(3) | compound 1-3 | 5.3 | 11.5 | 2500 | 21.7 | 132.8 | 0.66 | 0.33 |
| example(4) | compound 1-4 | 5.1 | 10.2 | 2500 | 24.4 | 147.0 | 0.66 | 0.32 |
| example(5) | compound 1-8 | 5.0 | 9.9 | 2500 | 25.3 | 149.1 | 0.66 | 0.33 |
| example(6) | compound 1-12 | 5.0 | 10.0 | 2500 | 25.1 | 148.6 | 0.66 | 0.33 |
| example(7) | compound 1-13 | 5.1 | 10.2 | 2500 | 24.6 | 147.1 | 0.66 | 0.32 |
| example(8) | compound 1-15 | 5.0 | 10.0 | 2500 | 24.9 | 147.8 | 0.66 | 0.33 |
| example(9) | compound 1-16 | 5.3 | 11.2 | 2500 | 22.3 | 135.6 | 0.66 | 0.33 |
| example(10) | compound 1-17 | 5.3 | 11.6 | 2500 | 21.5 | 132.2 | 0.66 | 0.33 |
| example(11) | compound 1-18 | 5.0 | 10.1 | 2500 | 24.8 | 147.5 | 0.66 | 0.33 |
| example(12) | compound 1-30 | 5.4 | 13.7 | 2500 | 18.3 | 127.1 | 0.66 | 0.32 |
| example(13) | compound 1-33 | 5.4 | 13.4 | 2500 | 18.7 | 128.4 | 0.66 | 0.32 |
| example(14) | compound 1-41 | 5.4 | 12.8 | 2500 | 19.5 | 128.3 | 0.66 | 0.33 |
| example(15) | compound 1-42 | 5.2 | 10.5 | 2500 | 23.7 | 143.4 | 0.66 | 0.33 |
| example(16) | compound 1-43 | 5.2 | 10.6 | 2500 | 23.5 | 142.9 | 0.66 | 0.33 |
| example(17) | compound 1-45 | 5.2 | 10.8 | 2500 | 23.2 | 142.6 | 0.66 | 0.33 |
| example(18) | compound 1-52 | 5.2 | 10.5 | 2500 | 23.9 | 144.3 | 0.66 | 0.32 |
| example(19) | compound 1-54 | 4.9 | 9.2 | 2500 | 27.3 | 156.7 | 0.66 | 0.32 |
| example(20) | compound 1-55 | 4.9 | 9.1 | 2500 | 27.5 | 154.3 | 0.66 | 0.32 |
| example(21) | compound 1-56 | 4.9 | 9.0 | 2500 | 27.9 | 156.9 | 0.66 | 0.32 |
| example(22) | compound 1-58 | 5.2 | 10.3 | 2500 | 24.2 | 145.9 | 0.66 | 0.33 |
| example(23) | compound 1-60 | 4.9 | 9.3 | 2500 | 27.0 | 155.7 | 0.66 | 0.33 |
| example(24) | compound 1-61 | 4.9 | 9.3 | 2500 | 26.8 | 154.1 | 0.66 | 0.32 |
| example(25) | compound 1-65 | 5.4 | 12.4 | 2500 | 20.1 | 129.7 | 0.66 | 0.33 |
| example(26) | compound 1-75 | 5.4 | 12.1 | 2500 | 20.7 | 131.8 | 0.66 | 0.33 |
| example(27) | compound 1-79 | 5.3 | 11.0 | 2500 | 22.8 | 136.4 | 0.66 | 0.33 |
| example(28) | compound 1-81 | 5.3 | 10.9 | 2500 | 22.9 | 137.0 | 0.66 | 0.33 |
| example(29) | compound 1-82 | 5.0 | 9.5 | 2500 | 26.2 | 153.4 | 0.66 | 0.32 |
| example(30) | compound 1-83 | 5.0 | 9.7 | 2500 | 25.9 | 152.7 | 0.66 | 0.33 |
| example(31) | compound 1-84 | 5.0 | 9.4 | 2500 | 26.7 | 153.6 | 0.66 | 0.33 |
| example(32) | compound 1-85 | 5.1 | 9.6 | 2500 | 26.0 | 152.5 | 0.66 | 0.33 |
| example(33) | compound 1-87 | 5.1 | 9.7 | 2500 | 25.7 | 149.8 | 0.66 | 0.33 |
| example(34) | compound 1-90 | 5.1 | 9.8 | 2500 | 25.4 | 149.3 | 0.66 | 0.33 |
| example(35) | compound 1-93 | 5.3 | 11.8 | 2500 | 21.1 | 131.3 | 0.66 | 0.32 |
| example(36) | compound 1-98 | 5.2 | 10.9 | 2500 | 23.0 | 137.3 | 0.66 | 0.33 |
| example(37) | compound 1-100 | 5.3 | 11.1 | 2500 | 22.6 | 135.9 | 0.66 | 0.33 |

As can be seen from the results of Table 4, it can be confirmed that the device using the compound according to one embodiment of the present invention as the phosphorescent host material of the emitting layer is significantly improved in electrical characteristics as compared with the device using Comparative Compounds 1 to 4 as the phosphorescent host material in the emitting layer.

First, comparing Comparative Example 1 with Comparative Example 2, Comparative Example 2 using the comparative compound 2, which is a heterophasic ring compound having different hetero atoms (N, S), shows a higher efficiency than Comparative Example 1 using Comparative Compound 1 having the same nitrogen atom. Also, by comparing the compounds 1-8, 1-56 and 1-84 of the present invention, it can be seen that the device of the compound having heteroatom of the dissimilar type exhibits the improved electrical characteristic more than the device of the compound having the heteroatom of the same type.

Compounds having different heteroatoms has an antiparallelcofacial π-stacking structure in which the packing structure of the molecule faces in the opposite direction rather than the compounds having the same heteroatom.

Thus, the arrangement order of the molecules is made face-to-face, and it is considered that the steric effect of $Ar^1$ of the asymmetrically arranged hetero atom N, which is the cause of the stacking structure, results in remarkably high carrier mobility and thus has a high efficiency, and the lifetime is remarkably increased due to high oxidation stability.

In addition, Comparative Compounds 3 and 4, which are 6-ring compounds in which benzene is fused at a specific position of Comparative Compound 2, showed excellent results in terms of driving voltage, efficiency, and lifetime. Further, it can be seen that the compound of the present invention, which is a 7-ring compound in which benzene is fused at a specific position more than the Comparative compound 3, shows remarkably excellent results in terms of all the electrical characteristics of the device. This indicates that the device has an excellent device result because one more benzene is fused at a specific position, the T1 value of the compound is lowered, the charge transfer from the host to the dopant is smooth, and the charge balance in the emitting layer is increased.

As a result, through comparison of the comparative compounds 1 to 4 and the inventive example compounds, since the energy level of the compound varies depending on the number of the compound rings, the compounds of the present invention have appropriate HOMO and LUMO energies compared with Comparative Compounds 1 to 4, and the charge balance in the emitting layer of holes and electrons is increased, therefore the device result is improved as compared with the comparative example device using the comparative compound.

On the other hand, in the device result of the embodiment of the present invention, it can be confirmed that the chemical properties such as the energy band gap and the device characteristics such as the packing density are remarkably changed due to the introduction of a specific substituent group to the hetero atom N in the same core. That is, it can be seen that the driving voltage, efficiency and lifetime of the device are improved by introducing a specific substituent such as a heteroaryl group other than a simple aryl group into N.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:
1. A compound represented by Formula 1:

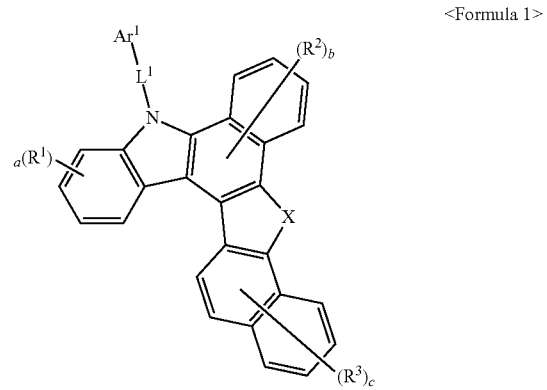

<Formula 1> wherein:
1) X is $N-L^2-Ar^2$, O or S,
2) $Ar^1$ and $Ar^2$ are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and $-L'-N(R^a)(R^b)$;
3) a and b are an integer of 0 to 4, and c is an integer of 0 to 6,
4) $R^1$, $R^2$ and $R^3$ are the same or different from each other, and are each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and $-L'-N(R^a)(R^b)$; or in case a, b and c are 2 or more, and $R^1$, $R^2$ and $R^3$ are each in plural being the same or different, a plurality of $R^1$ or a plurality of $R^2$ or a plurality of $R^3$ may be bonded to each other to form a ring, with the proviso that the plurality of $R^1$ does not form a heterocyclic ring, with the proviso that $R^1$ is not halogen, and with the proviso that where X is O or S, $R^3$ is hydrogen,
5) $L^1$ and $L^2$ are each independently selected from the group consisting of a single bond; a $C_6$-$C_{60}$ arylene group; and a fluorenylene group; a fused ring group of a $C_3$-$C_{60}$ aliphatic ring and a $C_6$-$C_{60}$ aromatic ring; and a $C_2$-$C_{60}$ heterocyclic group;
6) L' is selected from the group consisting of a single bond; a $C_6$-$C_{60}$ arylene group; and a fluorenylene group; a fused ring group of a $C_3$-$C_{60}$ aliphatic ring and a $C_6$-$C_{60}$ aromatic ring; and a $C_2$-$C_{60}$ heterocyclic group; and $R^a$ and $R^b$ are each independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P, wherein, the aryl group, fluorenyl group, arylene group, heterocyclic group, fluorenylene group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L'-N($R^a$)($R^b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; wherein the substituents may combine each other and form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination of thereof.

2. The compound of claim 1, wherein the compound represented by Formula 1 is represented by any one of the following Formulas 2 to 4:

<Formula 2>

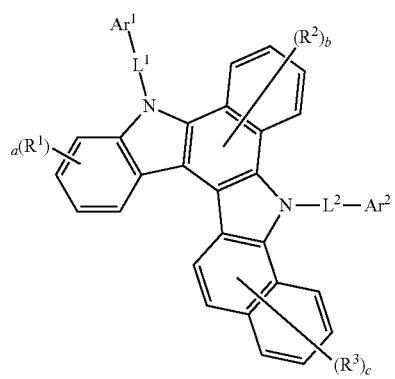

<Formula 3>

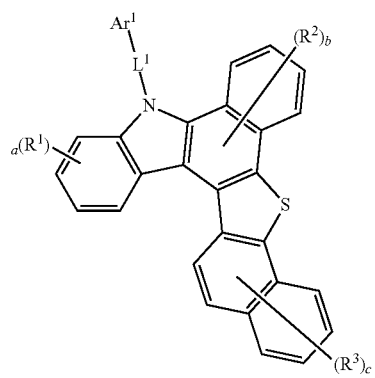

<Formula 4>

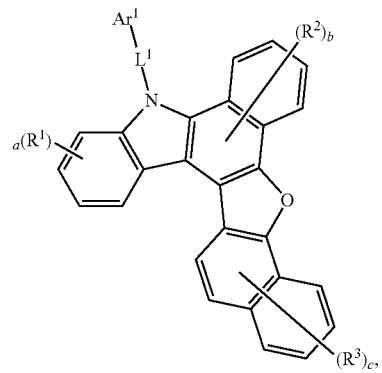

wherein $R^1$, $R^2$, $R^3$, $L^1$, $L^2$, $Ar^1$, $Ar^2$, a, b and c are the same as defined in claim 1.

3. The compound of claim 1, wherein $Ar^1$ or $Ar^2$ in Formula 1 are represented by Formula A-1 or A-2:

<Formula A-1>

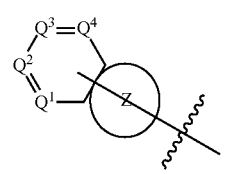

<Formula A-2>

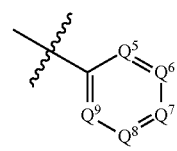

wherein:
1) $Q^1$, $Q^2$, $Q^3$, $Q^4$, $Q^5$, $Q^6$, $Q^7$, $Q^8$ and $Q^9$ are each independently N or $CR^e$,
2) $R^e$ is selected from the group consisting of hydrogen; deuterium; halogen; a silane group substituted or unsubstituted with $C_1$-$C_{20}$ alkyl group or $C_6$-$C_{20}$ aryl group; siloxane group; boron group; germanium group; cyano group; nitro group; a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; containing at least one hetero atom of O, N, S, Si, or P, $C_3$-$C_{20}$ cycloalkyl group; $C_7$-$C_{20}$ arylalkyl group; and $C_8$-$C_{20}$ arylalkenyl group;
3) Z is any one of Formulas C-1 to C-15:

<C-1>

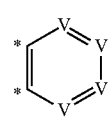

<C-2>

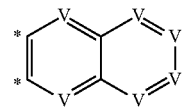

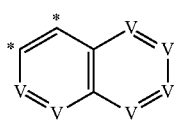
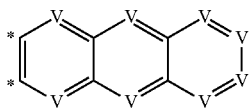
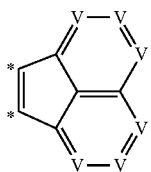
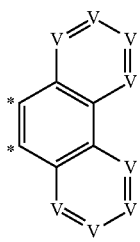
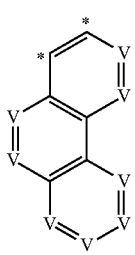
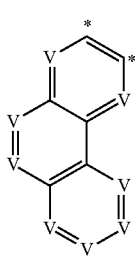
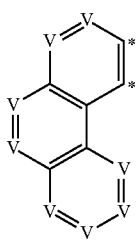

<C-3>
<C-4>
<C-5>
<C-6>
<C-7>
<C-8>
<C-9>

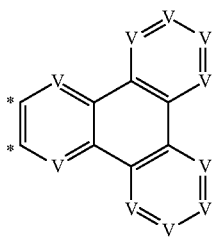
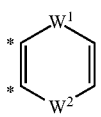
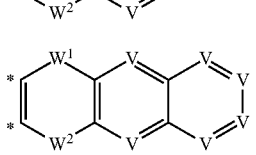
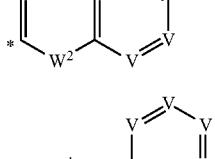

<C-10>
<C-11>
<C-12>
<C-13>
<C-14>
<C-15> wherein the mark * represents a bonding moiety which combines with the ring including Q1 to Q4 to form a fused ring, 4) in Formulas C-11 to C-15, $W^1$ and $W^2$ are single bond, $N-L^3-Ar^3$, S, O or $C(R^f)(R^g)$, 5) V is each independently N or $CR^h$, 6) $L^3$ is selected from a single bond; a $C_6-C_{60}$ arylene group; and a fluorenylene group; $C_2-C_{60}$ divalent heterocyclic group containing at least one hetero atom of O, N, S, Si, or P; a divalent fused ring group of a $C_3-C_{60}$ aliphatic ring and a $C_6-C_{60}$ aromatic ring; and a divalent aliphatic hydrocarbon group;

7) $Ar^3$, $R^f$, $R^g$ and $R^h$ are each independently selected from the aryl group, fluorenyl group, a $C_2-C_{60}$ heterocyclic group including at least one heteroatom of O, N, S, Si or P; a fused ring group of a $C_3-C_{60}$ aliphatic ring and a $C_6-C_{60}$ aromatic ring; a $C_1-C_{50}$ alkyl group; a $C_2-C_{20}$ alkenyl group; a $C_2-C_{20}$ alkynyl group; a $C_1-C_{30}$ alkoxyl group; a $C_6-C_{30}$ aryloxy group; $R^f$ and $R^g$ may be bonded to each other to form a spiro together with the carbon (C) to which they are bonded.

4. A compound selected from the group consisting of the following compounds 1-1 to 1-101:
1-1
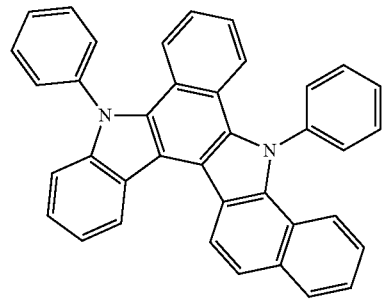
1-2
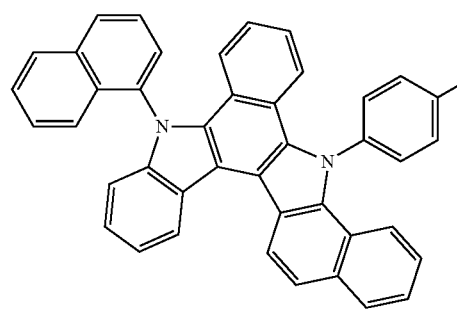
1-3
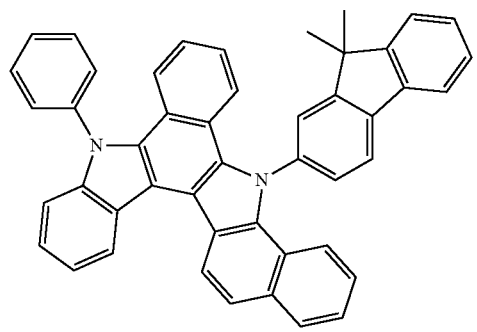
1-4
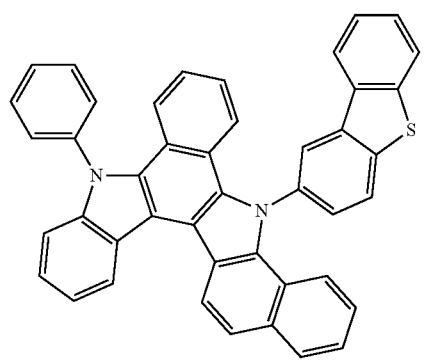
-continued
1-5
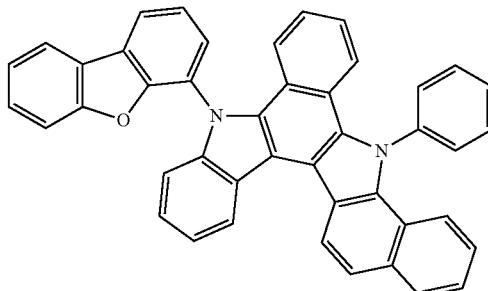
1-6
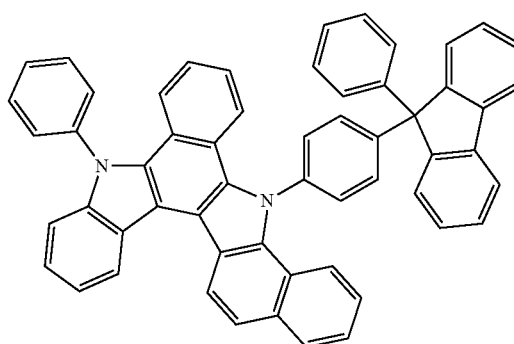
1-7
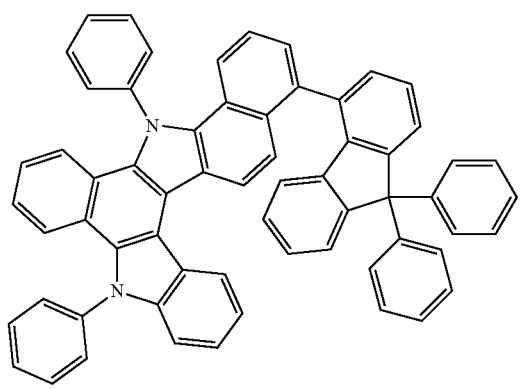
1-8
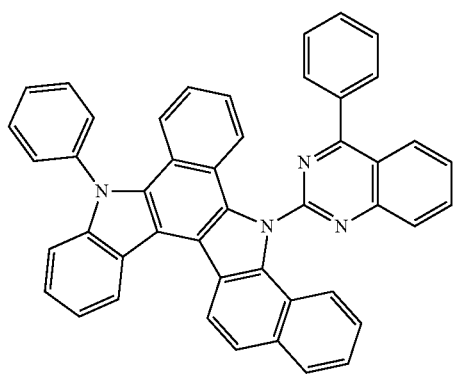

-continued
1-9
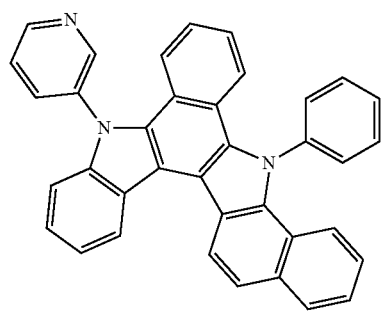
1-10
1-13
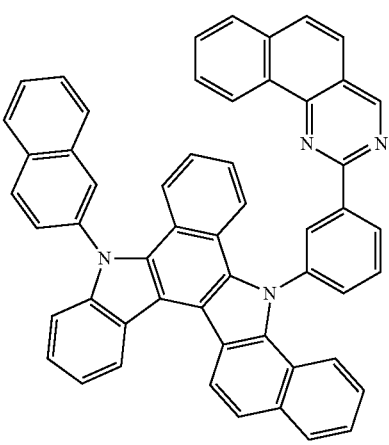
1-11
1-14
1-12
1-15
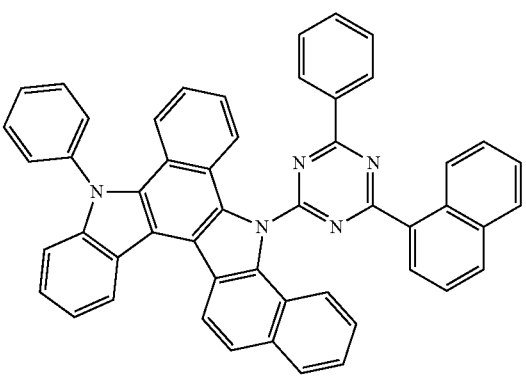

1-16
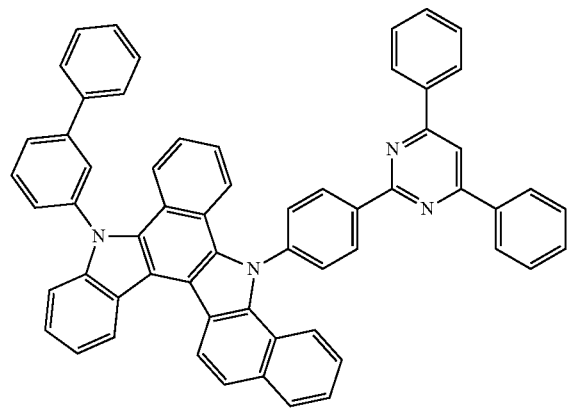
1-17
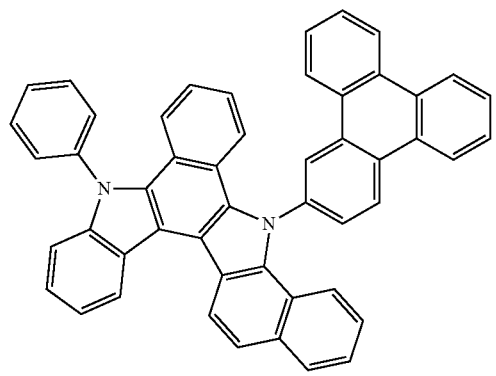
1-18
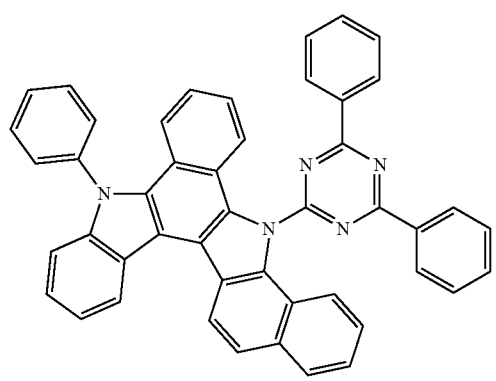
1-19
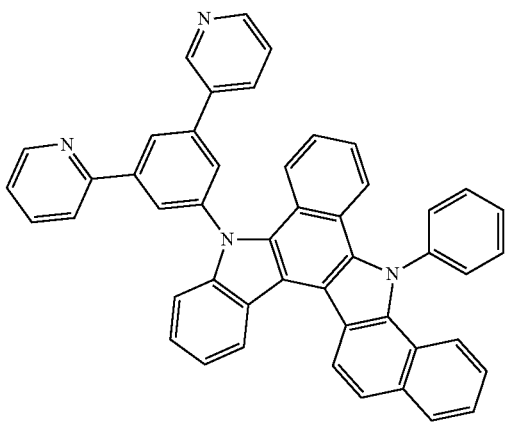
1-20
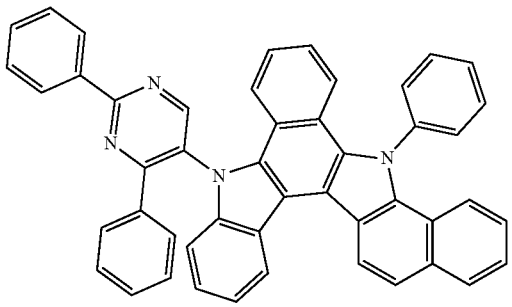
1-21
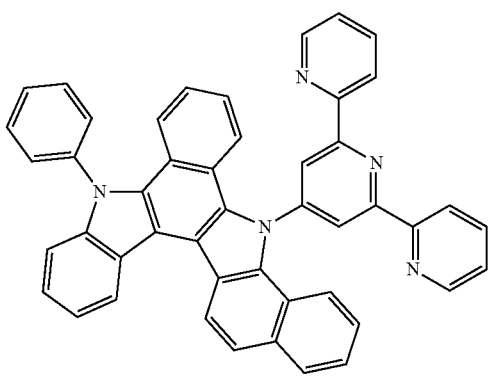
1-22
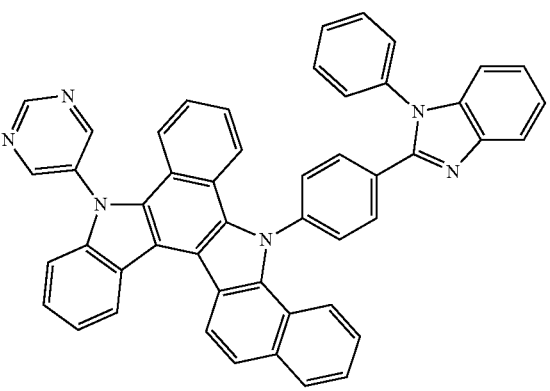

-continued
1-23
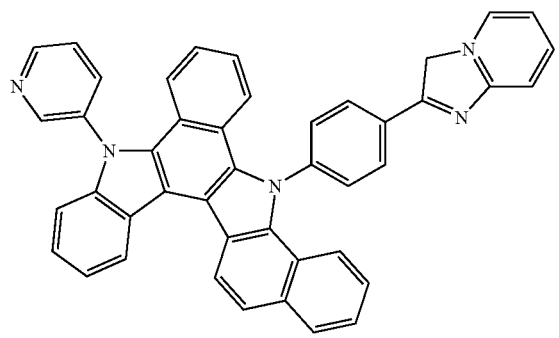
1-24
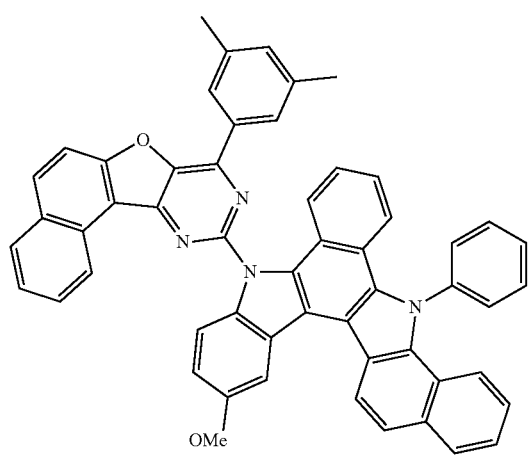
1-25
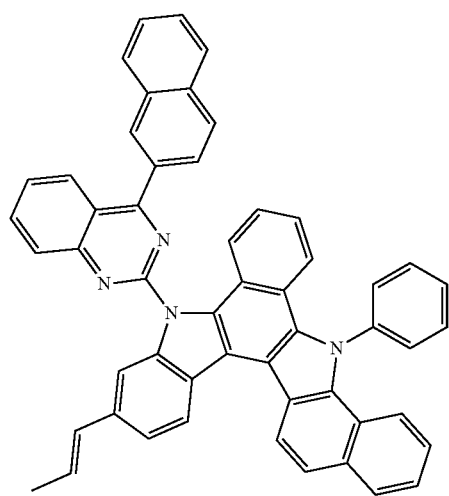
1-26
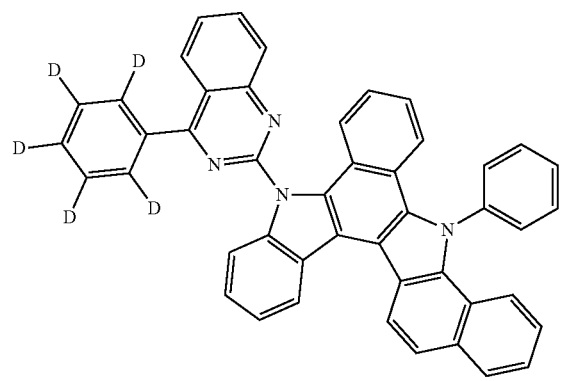
1-27
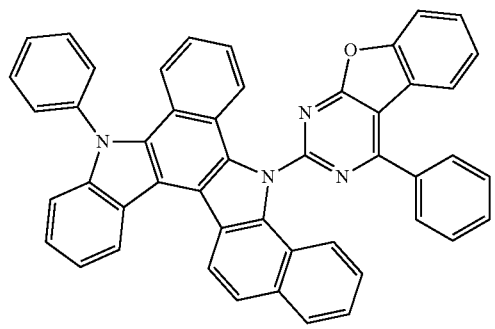
1-28
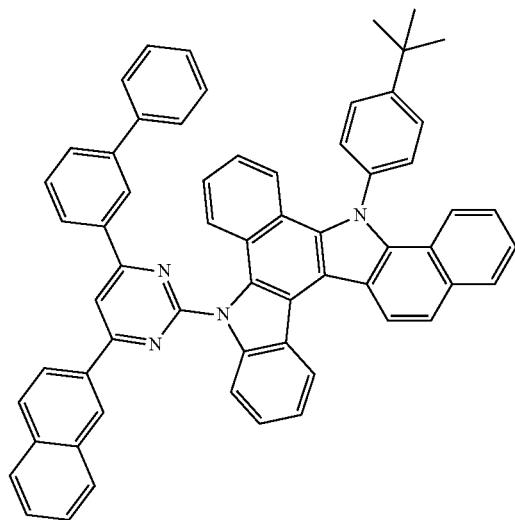

1-29
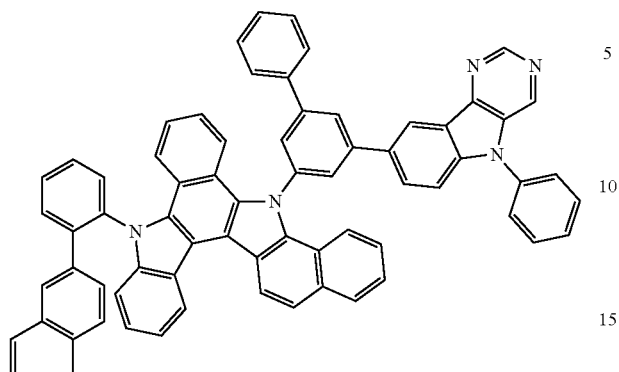
1-30
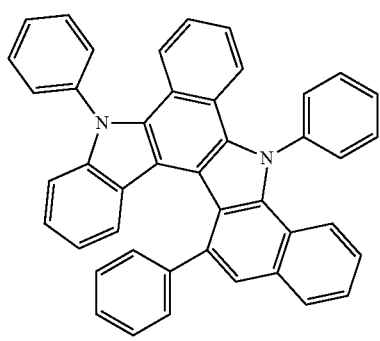
1-31
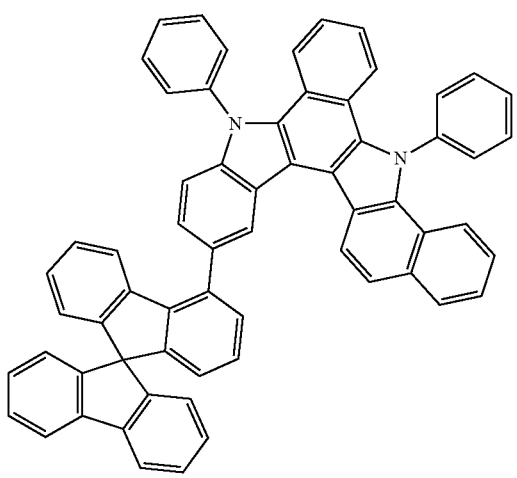
1-32
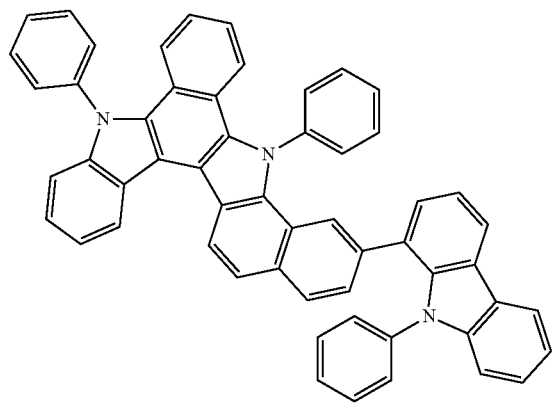
1-33
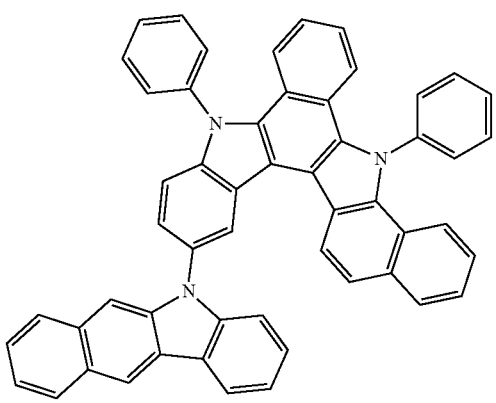
1-34
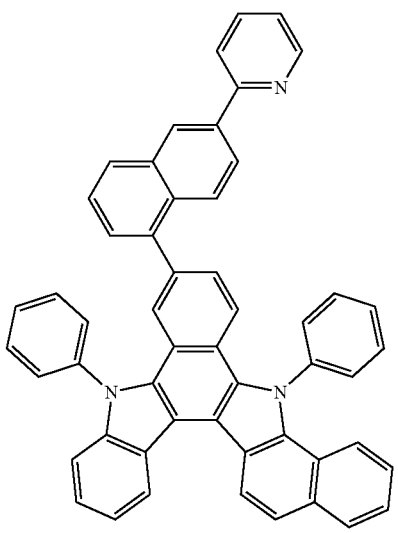

-continued
1-35
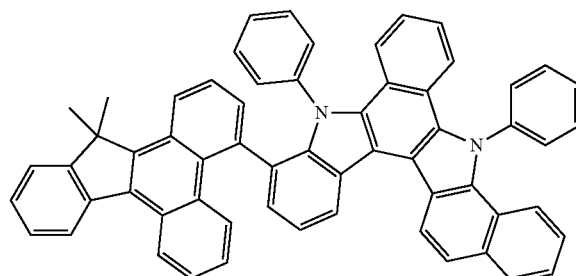
1-36
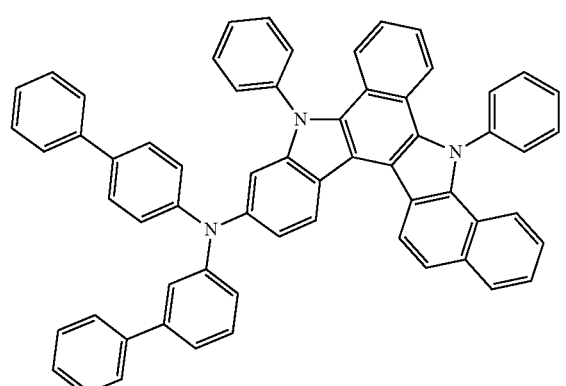
1-37
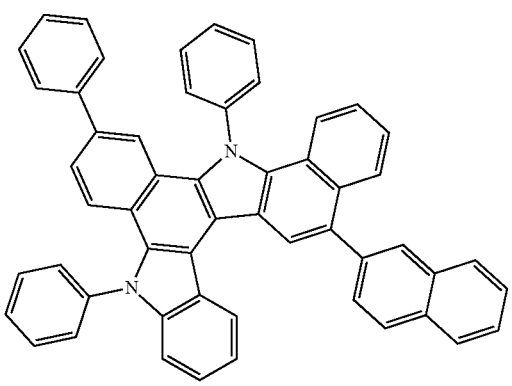
1-38
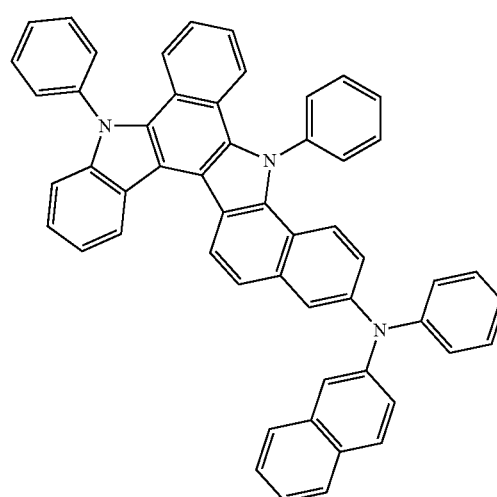
-continued
1-39
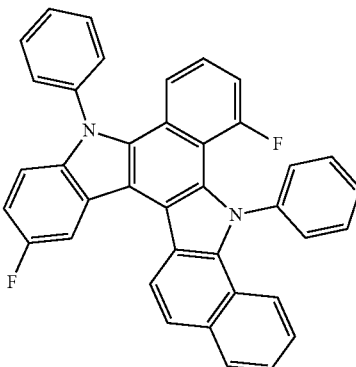
1-40
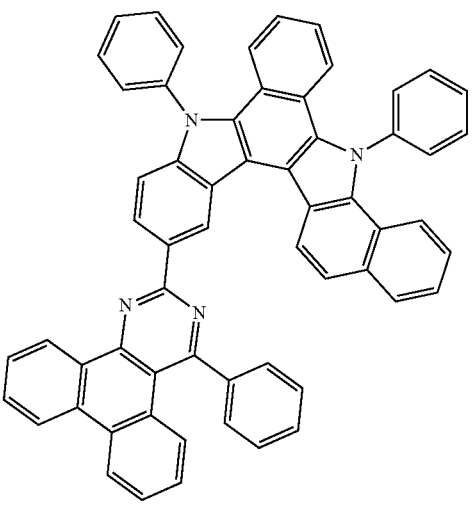
1-41
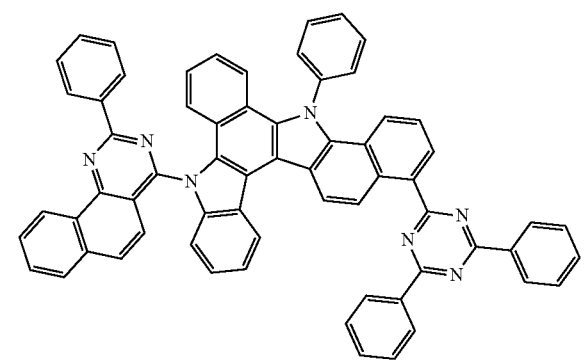
1-42
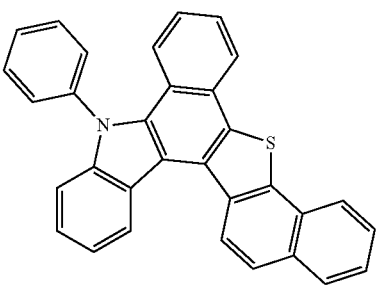

1-43
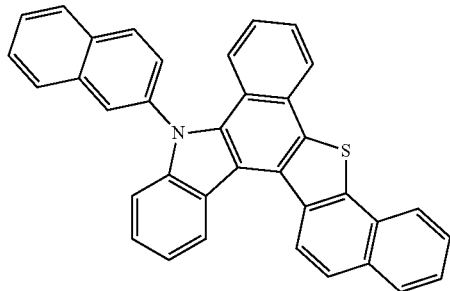
1-44
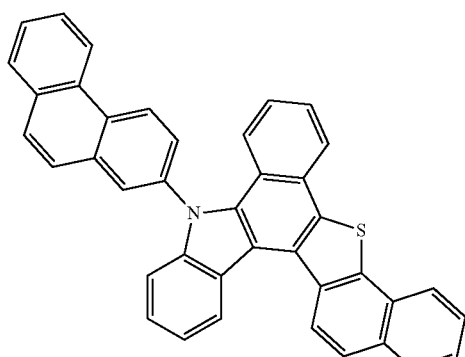
1-45
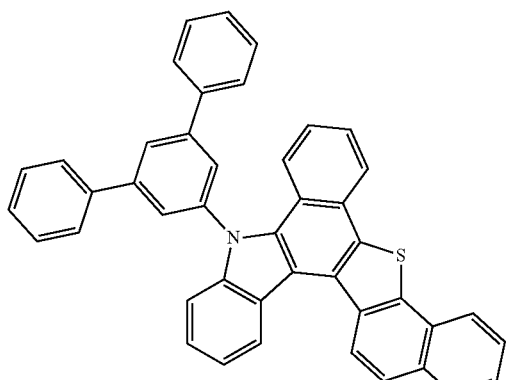
1-46
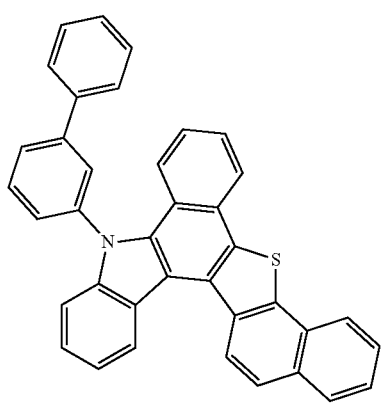
1-47
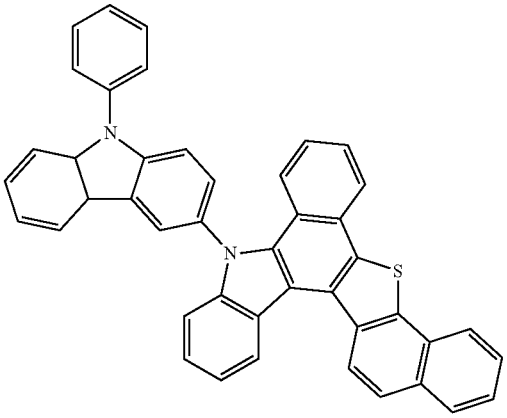
1-48
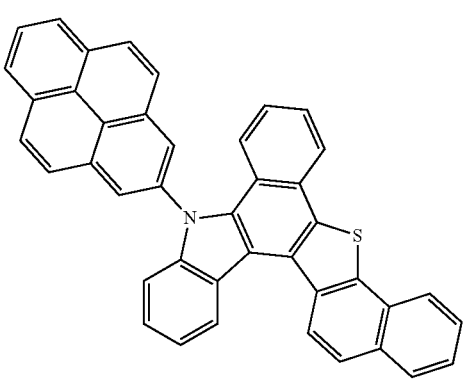
1-49
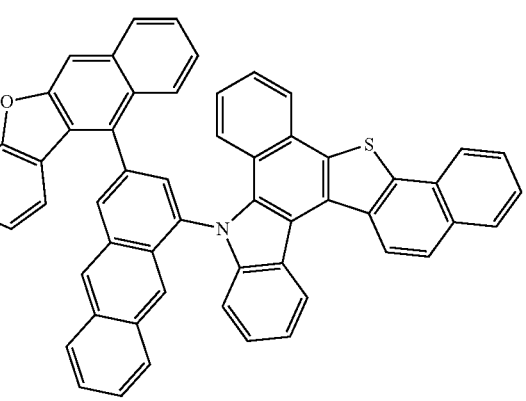
1-50
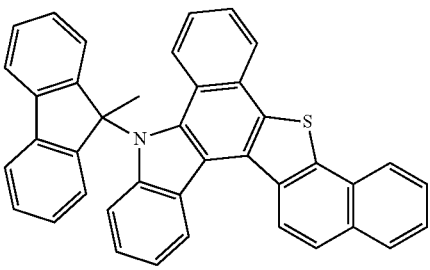

-continued
1-51
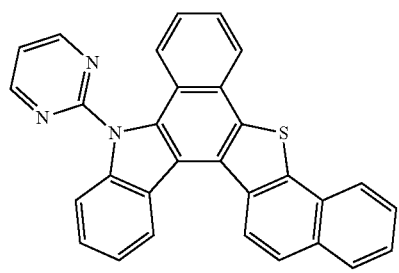
1-52
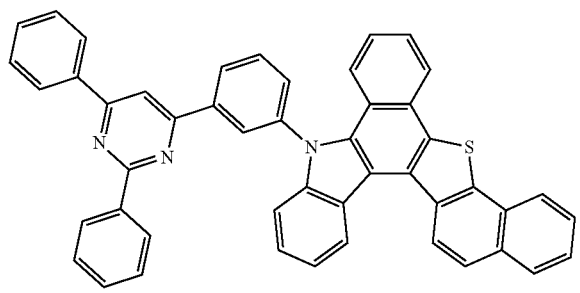
1-53
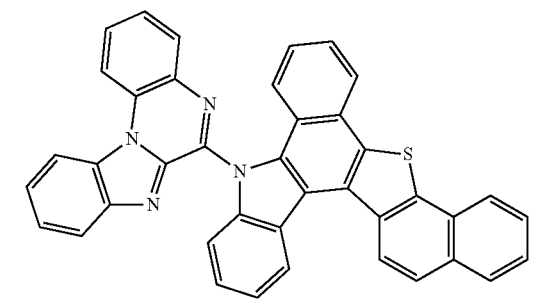
1-54
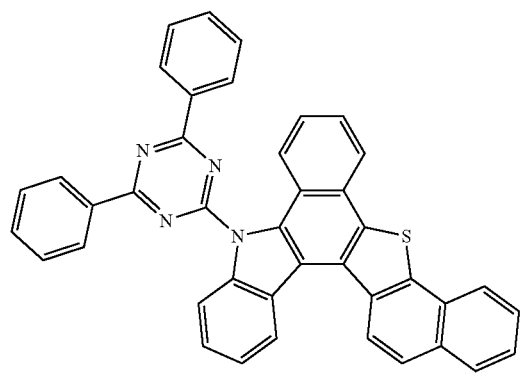
-continued
1-55
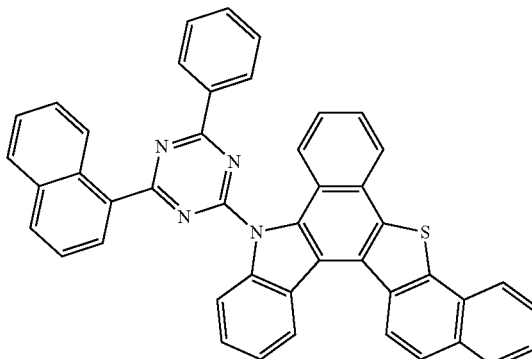
1-56
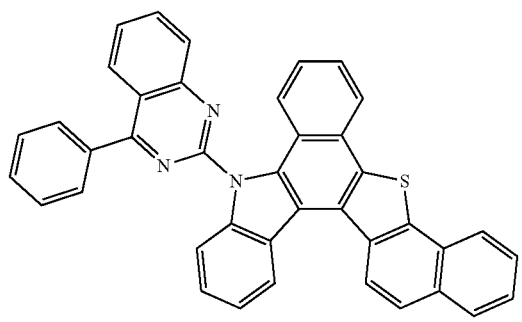
1-57
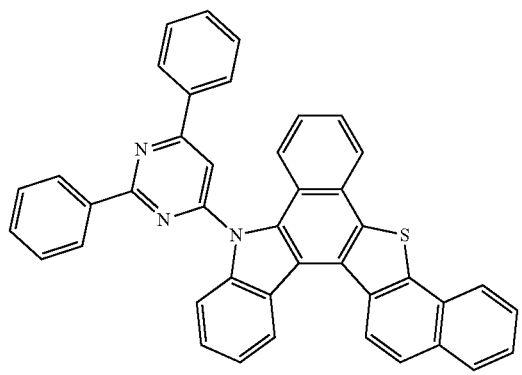
1-58
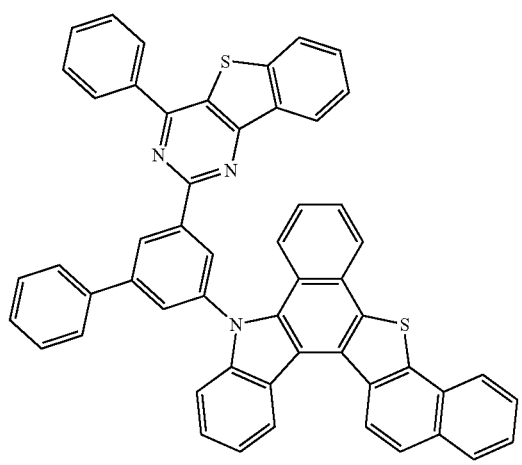

1-59
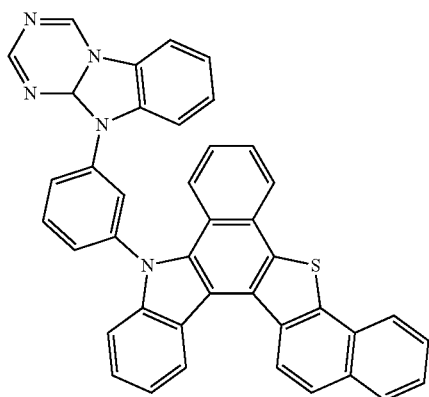
1-62
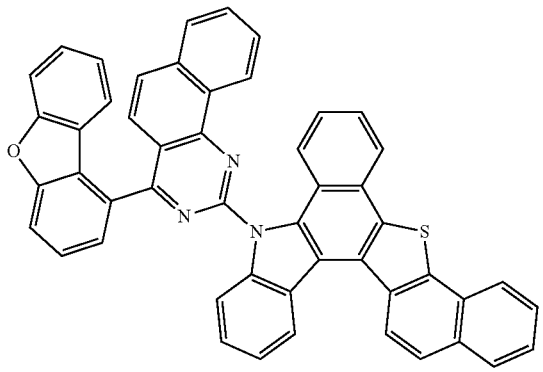
1-60
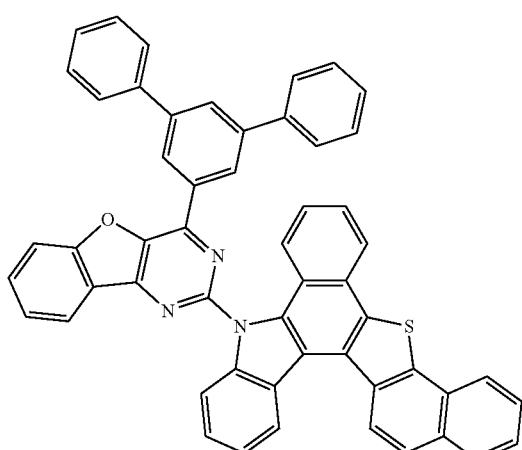
1-63
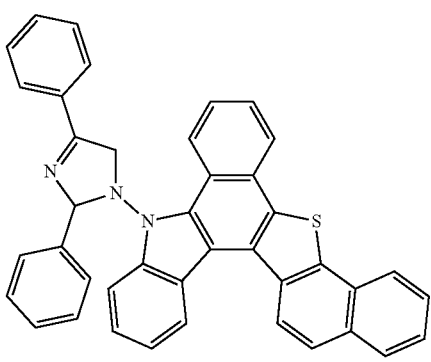
1-64
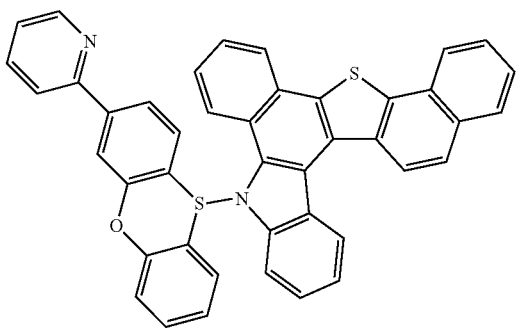
1-61
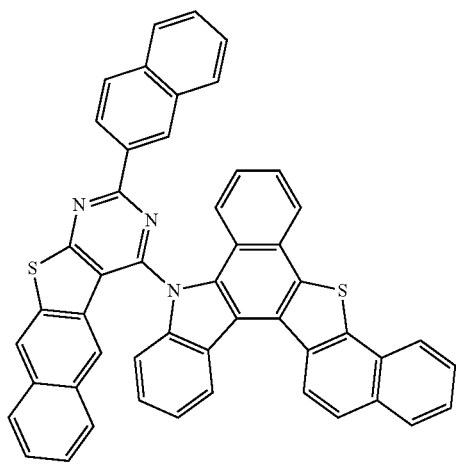
1-65
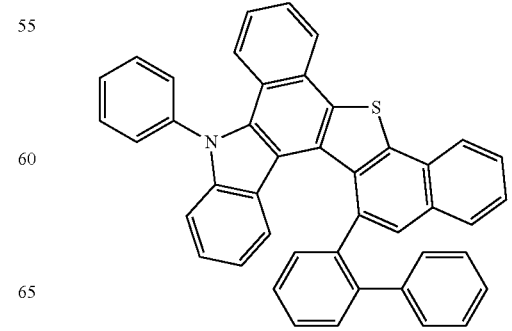

123
-continued
1-66
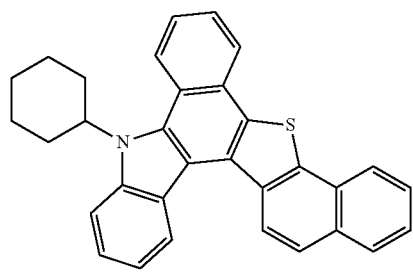
1-67
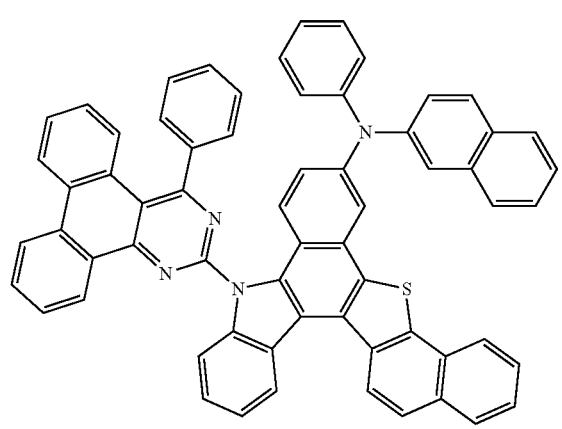
1-68
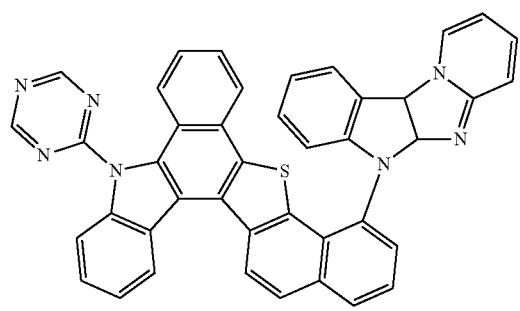
1-69
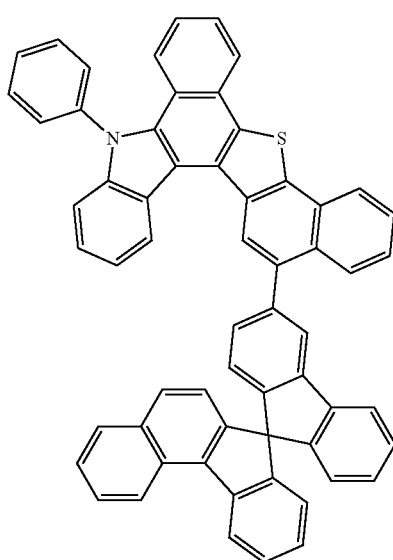
124
-continued
1-70
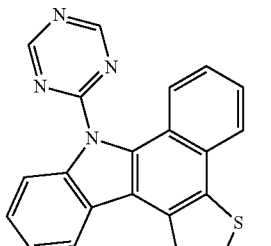
1-71
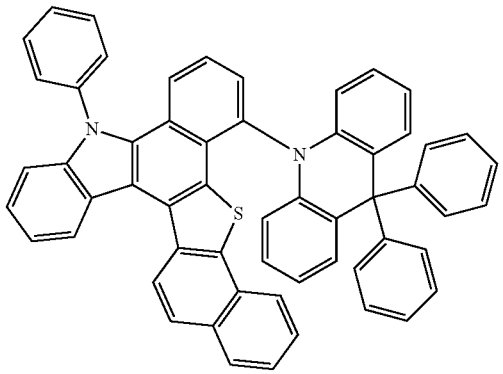
1-72
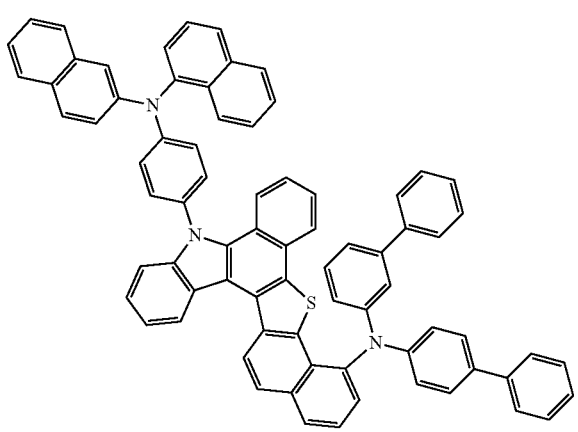

-continued
1-73
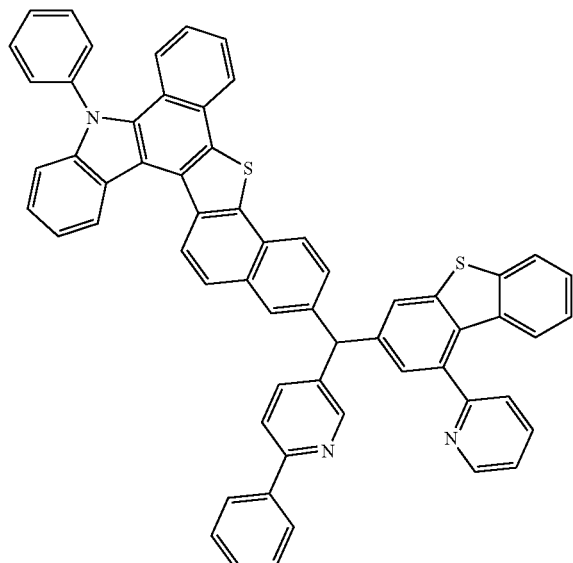
1-74
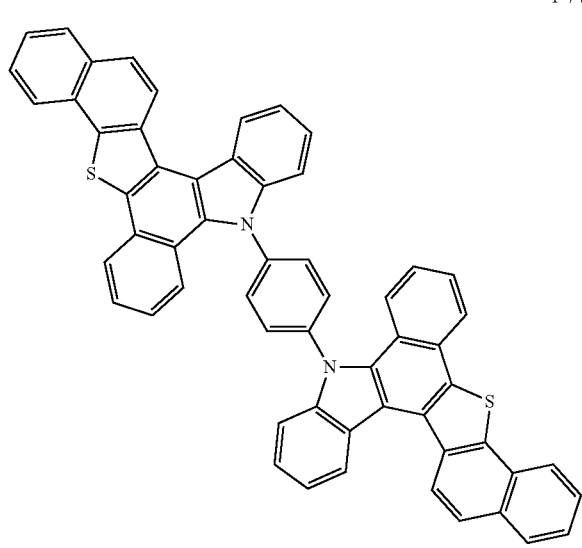
1-75
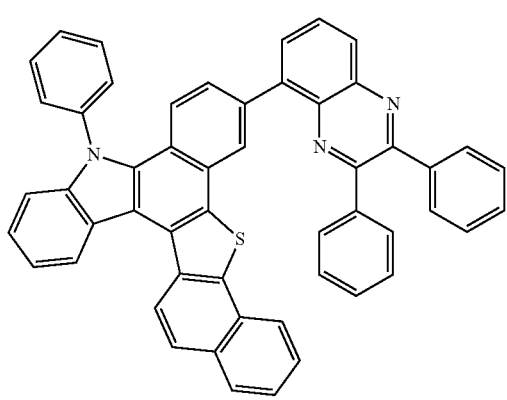
-continued
1-76
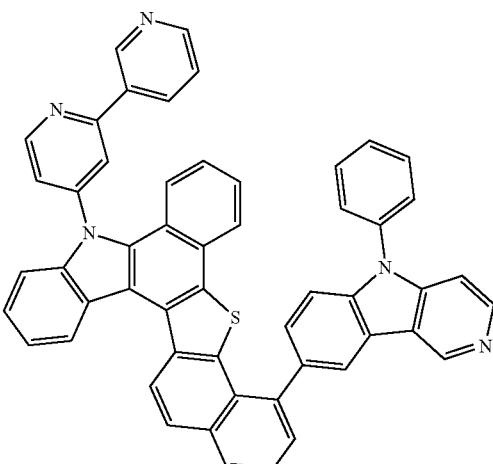
1-77
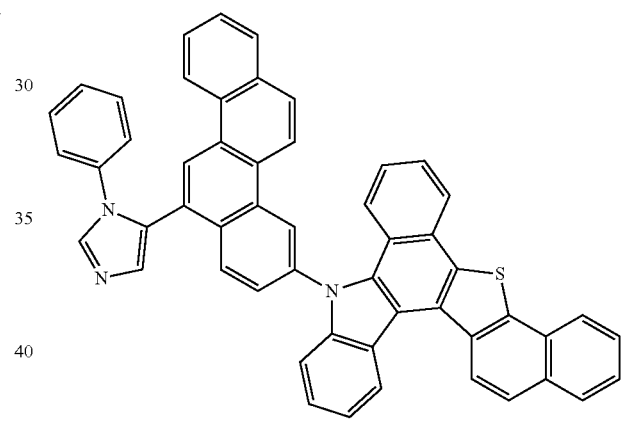
1-78
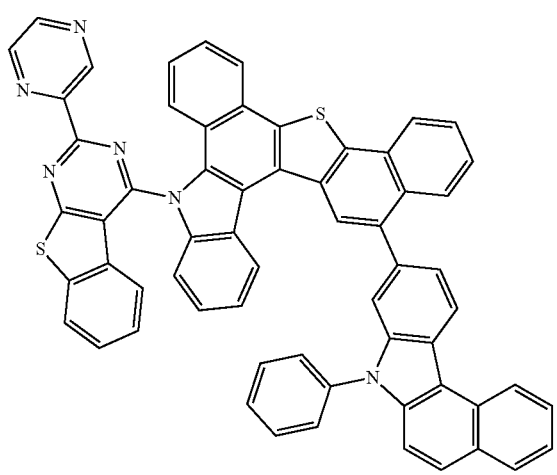

-continued
1-79
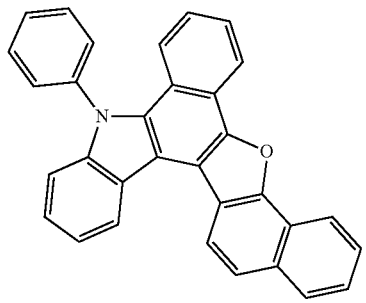
1-80
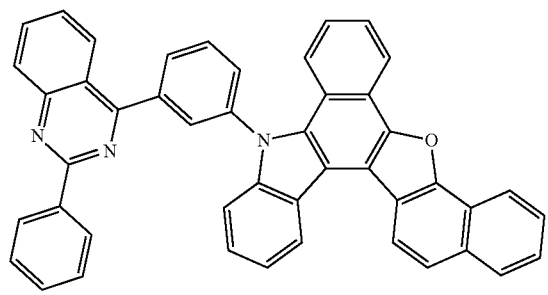
1-81
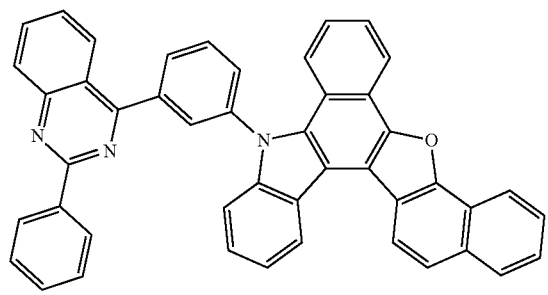
1-82
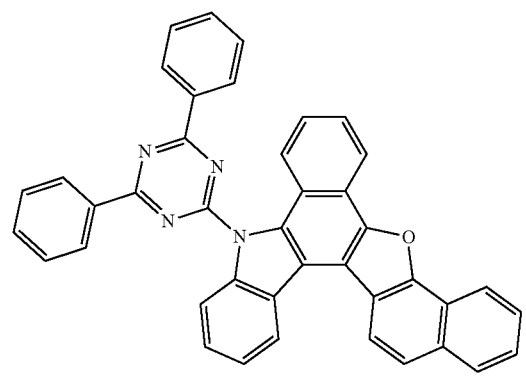
-continued
1-83
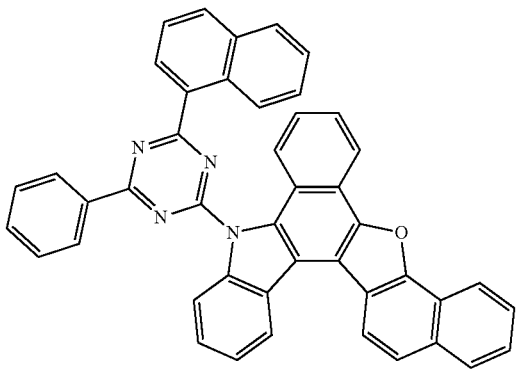
1-84
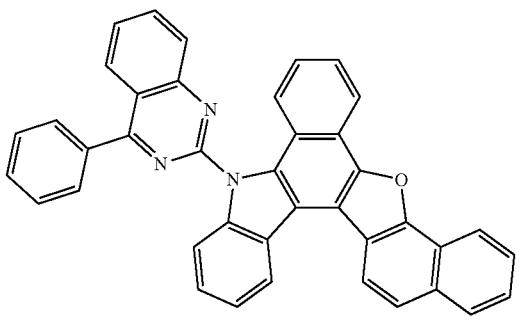
1-85
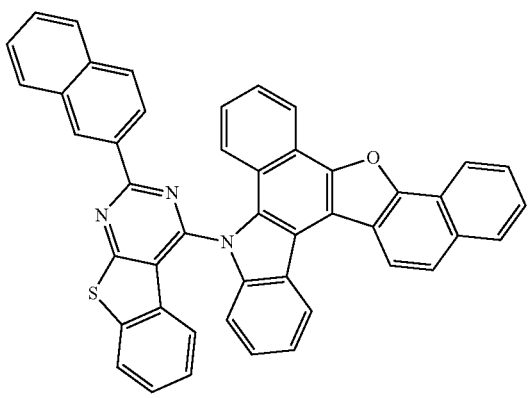
1-86
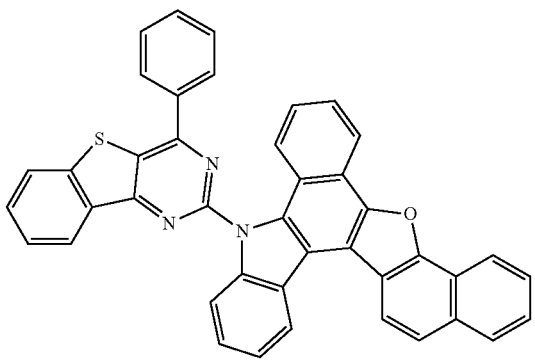

-continued
1-87
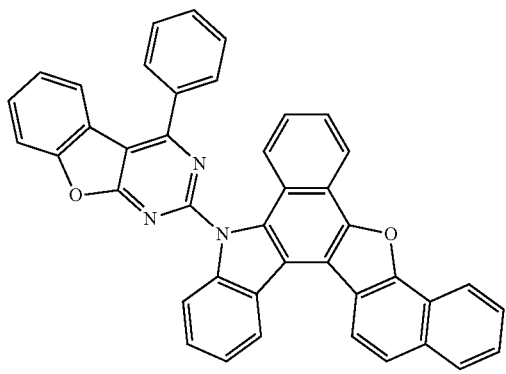
1-91
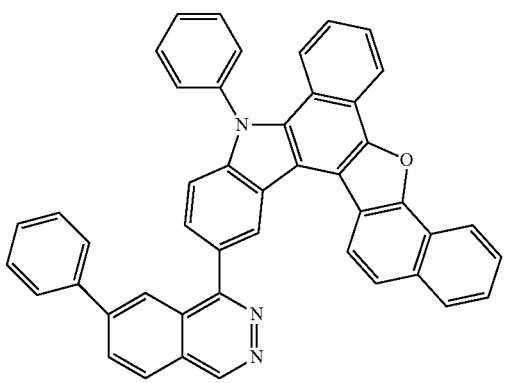
1-88
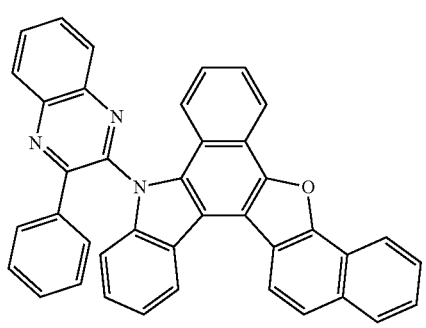
1-92
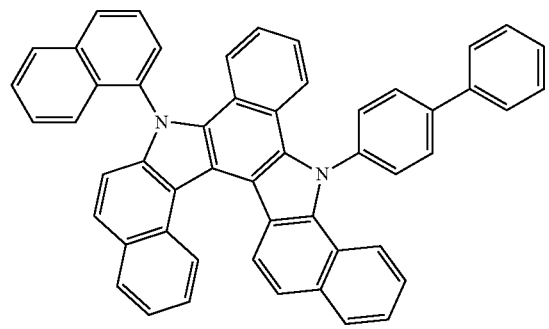
1-89
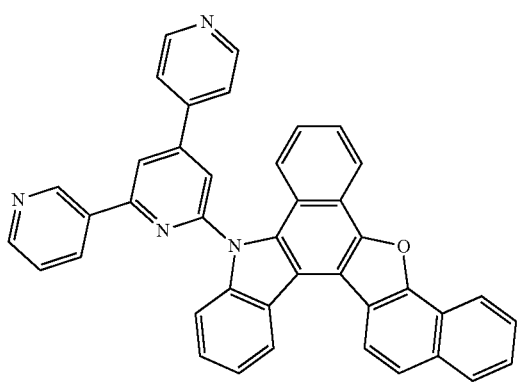
1-93
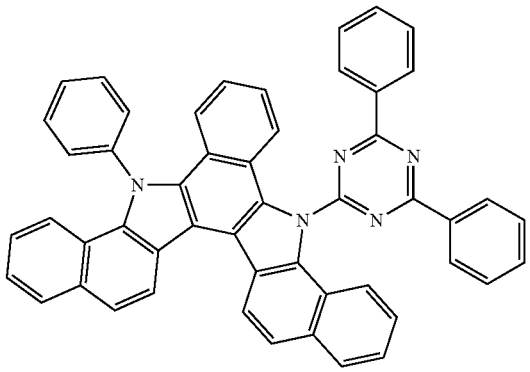
1-90
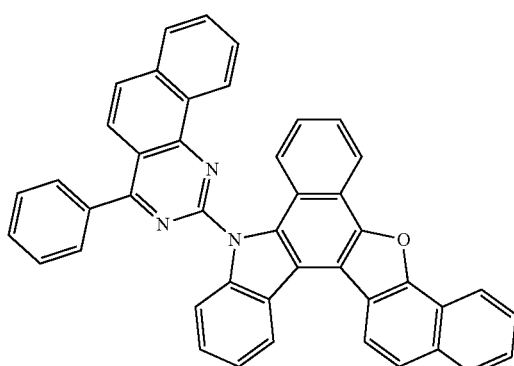
1-94
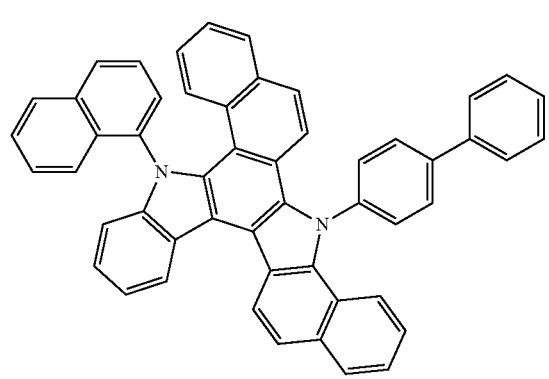

-continued
1-95
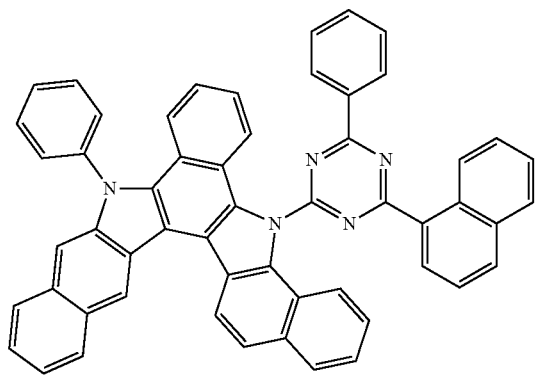
1-96
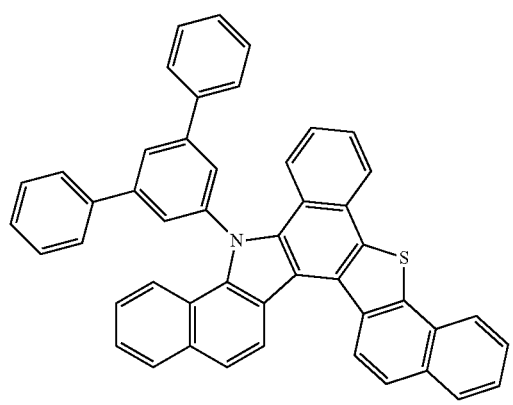
1-97
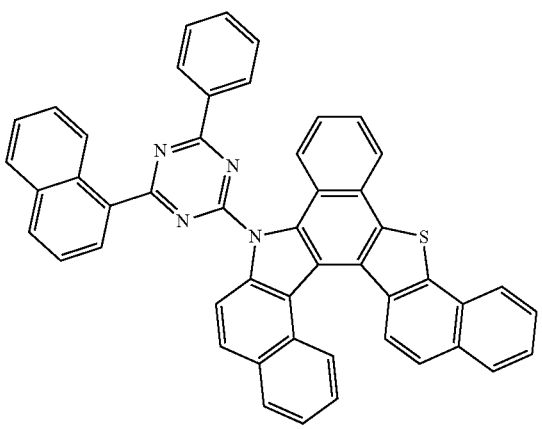
-continued
1-98
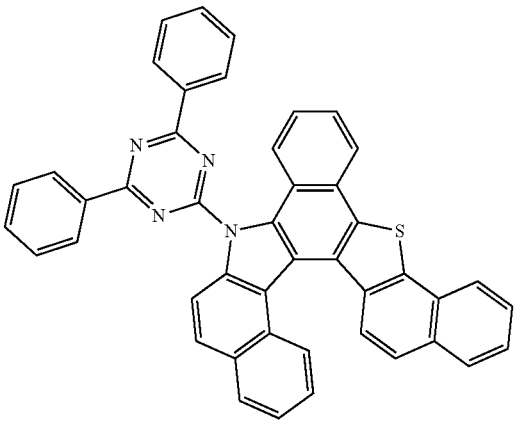
1-99
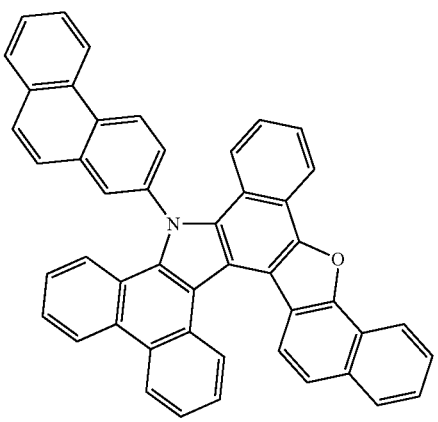
1-100
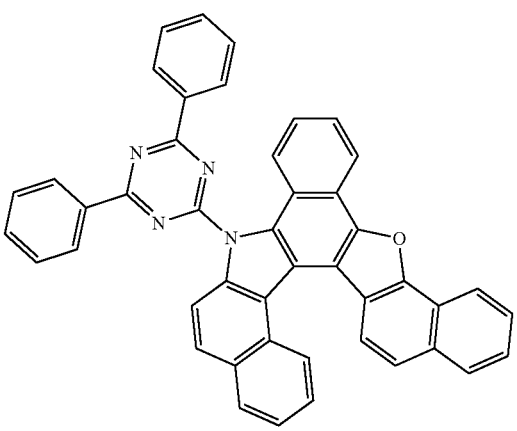

1-101

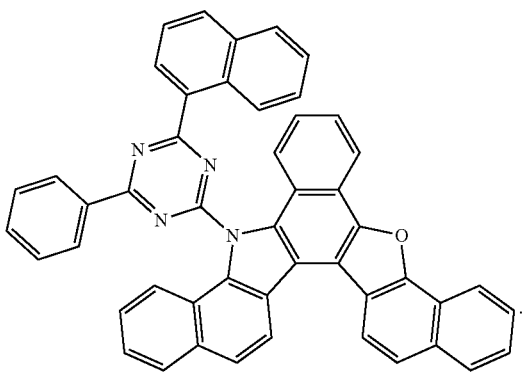

5. An organic electronic element comprising:
a first electrode; a second electrode; and an organic material layer disposed between the first electrode and the second electrode, wherein the organic material layer comprises a compound according to claim 1.

6. The organic electronic element according to claim 5, wherein the organic material layer is selected from the group consisting of a hole injection layer, a hole transport layer, an emitting auxiliary layer and emitting layer.

7. The organic electronic element according to claim 6, wherein the compound is used as a phosphorescent host material of the emitting layer.

8. The organic electronic element according to claim 5, wherein the organic material layer is formed by one of a spin coating process, a nozzle printing process, an inkjet printing process, a slot coating process, a dip coating process or a roll-to-roll process.

9. A display device comprising the organic electronic element of claim 5, and a control part driving the display device.

10. The display device according to claim 9, wherein the organic electronic element is at least one of an OLED, an organic solar cell, an organic photo conductor(OPC), organic transistor(organic TFT) and an element for monochromic or white illumination.

11. An organic electronic element comprising:
a first electrode; a second electrode; and an organic material layer disposed between the first electrode and the second electrode, wherein the organic material layer comprises a compound according to claim 4.

12. A display device comprising the organic electronic element of claim 11;
and a control part driving the display device.

* * * * *